(12) United States Patent
Kilpela et al.

(10) Patent No.: US 10,182,852 B2
(45) Date of Patent: *Jan. 22, 2019

(54) INTERVERTEBRAL IMPLANT DEVICES AND METHODS FOR INSERTION THEREOF

(71) Applicant: Pioneer Surgical Technology, Inc., Marquette, MI (US)

(72) Inventors: Thomas S. Kilpela, Marquette, MI (US); Brian P. Janowski, Marquette, MI (US); Jeffrey L. Trudeau, Marquette, MI (US); Russell M. Pietila, Hancock, MI (US); Michael R. Jackson, Hancock, MI (US); John Sullivan, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/402,903

(22) Filed: Jan. 10, 2017

(65) Prior Publication Data

US 2017/0112549 A1   Apr. 27, 2017

Related U.S. Application Data

(63) Continuation of application No. 14/216,271, filed on Mar. 17, 2014, now Pat. No. 9,545,269, which is a
(Continued)

(51) Int. Cl.
*A61B 17/70* (2006.01)
*A61F 2/44* (2006.01)
(Continued)

(52) U.S. Cl.
CPC .......... *A61B 17/7068* (2013.01); *A61B 17/70* (2013.01); *A61B 17/7065* (2013.01);
(Continued)

(58) Field of Classification Search
CPC ............ A61B 17/7065; A61B 17/7068; A61B 17/0256
See application file for complete search history.

(56) References Cited

U.S. PATENT DOCUMENTS

| 3,648,691 A | 3/1972 | Lumb |
| 4,349,921 A | 9/1982 | Kuntz |

(Continued)

FOREIGN PATENT DOCUMENTS

| AU | 2006200017 | 2/2006 |
| CA | 1146301 | 5/1983 |

(Continued)

*Primary Examiner* — Jacqueline Johanas
(74) *Attorney, Agent, or Firm* — Fitch, Even, Tabin & Flannery LLP

(57) ABSTRACT

An implant device is provided that is configured for implantation at multiple locations between adjacent vertebrae. The implant device comprises an implant body, a first portion of the implant body, and a second portion of the implant body adjustably interconnected with the first portion. The implant body has a compact orientation and an extended orientation to allow the implant body to be shifted from one orientation to the other orientation for being positioned in any one of areas between the spinous processes of the adjacent vertebrae, between laminar regions of the adjacent vertebrae, spanning an opening in the annulus between the adjacent vertebrae, and in the intervertebral space between the adjacent vertebrae.

10 Claims, 96 Drawing Sheets

Related U.S. Application Data continuation of application No. 12/026,895, filed on Feb. 6, 2008, now Pat. No. 8,672,976.

(60) Provisional application No. 60/981,824, filed on Oct. 23, 2007, provisional application No. 60/888,509, filed on Feb. 6, 2007.

(51) Int. Cl.
  *A61B 17/02* (2006.01)
  *A61F 2/30* (2006.01)
  *A61F 2/46* (2006.01)

(52) U.S. Cl.
  CPC .......... *A61B 17/7071* (2013.01); *A61F 2/442* (2013.01); *A61B 2017/0256* (2013.01); *A61F 2002/305* (2013.01); *A61F 2002/30131* (2013.01); *A61F 2002/30166* (2013.01); *A61F 2002/30471* (2013.01); *A61F 2002/30522* (2013.01); *A61F 2002/30563* (2013.01); *A61F 2002/30565* (2013.01); *A61F 2002/30579* (2013.01); *A61F 2002/30604* (2013.01); *A61F 2002/30616* (2013.01); *A61F 2002/30685* (2013.01); *A61F 2002/444* (2013.01); *A61F 2002/4435* (2013.01); *A61F 2002/4622* (2013.01); *A61F 2220/0025* (2013.01); *A61F 2220/0091* (2013.01); *A61F 2230/0013* (2013.01); *A61F 2230/0028* (2013.01)

(56) References Cited

U.S. PATENT DOCUMENTS

| | | |
|---|---|---|
| 4,401,112 A | 8/1983 | Rezaian |
| 4,657,550 A | 4/1987 | Daher |
| 4,696,290 A | 9/1987 | Steffee |
| 4,863,476 A | 9/1989 | Shepperd |
| 4,932,975 A | 6/1990 | Main |
| 5,059,193 A | 10/1991 | Kuslich |
| 5,171,278 A | 12/1992 | Pisharodi |
| 5,496,318 A | 3/1996 | Howland |
| 5,522,899 A | 6/1996 | Michelson |
| 5,614,205 A | 3/1997 | Usala |
| 5,645,599 A | 7/1997 | Samani |
| 5,824,331 A | 10/1998 | Usala |
| 5,836,948 A | 11/1998 | Zucherman |
| 5,860,977 A | 1/1999 | Zucherman |
| 5,876,404 A | 3/1999 | Zucherman |
| 5,885,284 A * | 3/1999 | Errico ............... A61B 17/7052 606/252 |
| 5,922,339 A | 7/1999 | Usala |
| 6,013,591 A | 1/2000 | Ying |
| 6,039,761 A | 3/2000 | Li |
| 6,048,342 A | 4/2000 | Zucherman |
| 6,068,630 A | 5/2000 | Zucherman |
| 6,068,974 A | 5/2000 | Klann |
| 6,074,390 A | 6/2000 | Zucherman |
| 6,090,112 A | 7/2000 | Zucherman |
| 6,149,652 A | 11/2000 | Zucherman |
| 6,152,926 A | 11/2000 | Zucherman |
| 6,156,038 A | 12/2000 | Zucherman |
| 6,183,471 B1 | 2/2001 | Zucherman |
| 6,190,387 B1 | 2/2001 | Zucherman |
| 6,190,414 B1 | 2/2001 | Young |
| 6,193,756 B1 | 2/2001 | Studer |
| 6,193,757 B1 | 2/2001 | Foley |
| 6,231,881 B1 | 5/2001 | Usala |
| 6,235,030 B1 | 5/2001 | Zucherman |
| 6,238,397 B1 | 5/2001 | Zucherman |
| 6,261,587 B1 | 7/2001 | Usala |
| 6,270,977 B1 | 8/2001 | Klann |
| 6,280,444 B1 | 8/2001 | Zucherman |
| 6,296,665 B1 | 10/2001 | Strnad |
| 6,315,994 B2 | 11/2001 | Usala |
| 6,332,882 B1 | 12/2001 | Zucherman |
| 6,332,883 B1 | 12/2001 | Zucherman |
| 6,352,707 B1 | 3/2002 | Usala |
| 6,364,883 B1 | 4/2002 | Santilli |
| 6,379,355 B1 | 4/2002 | Zucherman |
| 6,395,031 B1 | 5/2002 | Foley |
| 6,402,785 B1 | 6/2002 | Zdeblick |
| 6,419,676 B1 | 7/2002 | Zucherman |
| 6,419,677 B2 | 7/2002 | Zucherman |
| 6,451,019 B1 | 9/2002 | Zucherman |
| 6,451,020 B1 | 9/2002 | Zucherman |
| 6,454,806 B1 | 9/2002 | Cohen |
| 6,478,796 B2 | 11/2002 | Zucherman |
| 6,500,178 B2 | 12/2002 | Zucherman |
| 6,514,256 B2 | 2/2003 | Zucherman |
| 6,524,341 B2 | 2/2003 | Laeng |
| 6,533,786 B1 | 3/2003 | Needham |
| 6,626,944 B1 | 9/2003 | Taylor |
| 6,699,246 B2 | 3/2004 | Zucherman |
| 6,699,247 B2 | 3/2004 | Zucherman |
| 6,713,079 B2 | 3/2004 | Usala |
| 6,730,315 B2 | 5/2004 | Usala |
| 6,790,455 B2 | 9/2004 | Chu |
| 6,796,983 B1 | 9/2004 | Zucherman |
| 6,833,006 B2 | 12/2004 | Foley |
| 7,101,375 B2 | 9/2006 | Zucherman |
| 7,156,874 B2 | 1/2007 | Paponneau |
| 7,201,751 B2 | 4/2007 | Zucherman |
| 7,445,637 B2 | 11/2008 | Taylor |
| 7,988,708 B2 * | 8/2011 | Yeh ..................... A61B 17/7065 606/105 |
| 8,246,655 B2 * | 8/2012 | Jackson ............. A61B 17/7068 606/248 |
| 8,308,767 B2 * | 11/2012 | Hochschuler ....... A61B 17/7001 606/246 |
| 8,425,559 B2 * | 4/2013 | Tebbe ................ A61B 17/7062 606/248 |
| 8,439,950 B2 * | 5/2013 | Zentes ............... A61B 17/7065 606/248 |
| 8,603,141 B2 * | 12/2013 | Hochschuler ....... A61B 17/7068 606/246 |
| 8,672,976 B2 | 3/2014 | Kilpela |
| 9,545,269 B2 | 1/2017 | Kilpela |
| 2001/0031965 A1 | 10/2001 | Zucherman |
| 2003/0060891 A1 | 3/2003 | Shah |
| 2004/0115172 A1 | 6/2004 | Bianchi |
| 2004/0162618 A1 | 8/2004 | Mujwid |
| 2004/0167520 A1 | 8/2004 | Zucherman |
| 2004/0181282 A1 | 9/2004 | Zucherman |
| 2004/0199252 A1 | 10/2004 | Sears |
| 2004/0199255 A1 | 10/2004 | Mathieu |
| 2004/0210312 A1 | 10/2004 | Neumann |
| 2004/0220568 A1 | 11/2004 | Zucherman |
| 2005/0021144 A1 | 1/2005 | Malberg |
| 2005/0031704 A1 | 2/2005 | Ahn |
| 2005/0101955 A1 | 5/2005 | Zucherman |
| 2005/0118230 A1 | 6/2005 | Hill |
| 2005/0125062 A1 | 6/2005 | Biedermann |
| 2005/0143738 A1 | 6/2005 | Zucherman |
| 2005/0165398 A1 | 7/2005 | Reiley |
| 2005/0196420 A1 | 9/2005 | Zucherman |
| 2005/0203512 A1 | 9/2005 | Hawkins |
| 2005/0209603 A1 | 9/2005 | Zucherman |
| 2005/0228383 A1 | 10/2005 | Zucherman |
| 2005/0228384 A1 | 10/2005 | Zucherman |
| 2005/0240182 A1 | 10/2005 | Zucherman |
| 2005/0245937 A1 | 11/2005 | Winslow |
| 2005/0261768 A1 | 11/2005 | Trieu |
| 2006/0004447 A1 | 1/2006 | Mastrorio |
| 2006/0030943 A1 | 2/2006 | Peterman |
| 2006/0041314 A1 | 2/2006 | Millard |
| 2006/0089654 A1 | 4/2006 | Lins |
| 2006/0129244 A1 | 6/2006 | Ensign |
| 2006/0142858 A1 | 6/2006 | Colleran |
| 2006/0224159 A1 | 10/2006 | Anderson |
| 2006/0235521 A1 | 10/2006 | Zucherman |
| 2006/0241597 A1 | 10/2006 | Mitchell |
| 2006/0241614 A1 | 10/2006 | Bruneau |
| 2006/0241770 A1 | 10/2006 | Rhoda |

(56) References Cited

U.S. PATENT DOCUMENTS

| | | |
|---|---|---|
| 2006/0259037 A1 | 11/2006 | Hartmann |
| 2006/0271194 A1 | 11/2006 | Zucherman |
| 2006/0293662 A1 | 12/2006 | Boyer |
| 2006/0293663 A1 | 12/2006 | Walkenhorst |
| 2007/0055246 A1 | 3/2007 | Zucherman |
| 2007/0073398 A1 | 3/2007 | Fabian |
| 2007/0161992 A1* | 7/2007 | Kwak ............ A61B 17/7065 606/249 |
| 2007/0162001 A1 | 7/2007 | Chin |
| 2007/0179500 A1* | 8/2007 | Chin ............ A61B 17/7065 606/276 |
| 2007/0191837 A1 | 8/2007 | Trieu |
| 2007/0191959 A1 | 8/2007 | Hartmann |
| 2007/0233076 A1* | 10/2007 | Trieu ............ A61B 17/7065 606/249 |
| 2007/0270840 A1* | 11/2007 | Chin ............ A61B 17/7065 606/276 |
| 2008/0114456 A1 | 5/2008 | Dewey |
| 2008/0177271 A1* | 7/2008 | Yeh ............ A61B 17/7065 606/90 |
| 2010/0179595 A1* | 7/2010 | Jackson ............ A61B 17/7065 606/249 |
| 2011/0106163 A1 | 5/2011 | Hochschuler |

FOREIGN PATENT DOCUMENTS

| | | |
|---|---|---|
| EP | 0042271 | 12/1981 |
| EP | 0834295 | 4/1998 |
| FR | 2703580 | 10/1994 |
| WO | 9000037 | 1/1990 |
| WO | 0209626 | 2/2002 |
| WO | 2005086776 | 9/2005 |
| WO | 2005115261 | 12/2005 |
| WO | 2006064356 | 6/2006 |
| WO | 2006102428 | 9/2006 |
| WO | 2007015028 | 2/2007 |
| WO | 2007016801 | 2/2007 |
| ZA | 20103898 | 6/2010 |
| ZA | 201103777 | 6/2012 |

* cited by examiner

INTERVERTEBRAL IMPLANT DEVICES AND METHODS FOR INSERTION THEREOF

CROSS-REFERENCE OF RELATED APPLICATIONS

This application is a continuation of U.S. application Ser. No. 14/216,271, filed Mar. 17, 2014, which is a continuation of U.S. application Ser. No. 12/026,895, filed Feb. 6, 2008, which issued as U.S. Pat. No. 8,672,976 on Mar. 18, 2014, which claims the benefit of Provisional Application No. 60/888,509, filed Feb. 6, 2007, and Provisional Application No. 60/981,824 filed, Oct. 23, 2007, all of which are hereby incorporated by reference in their entireties.

FIELD OF THE INVENTION

The invention relates to implant devices for implantation between adjacent vertebrae and, in particular, to implant devices positionable between spinous processes of adjacent vertebrae, between laminar regions of adjacent vertebrae, spanning an opening in the annulus between adjacent vertebral bodies, and/or in the intervertebral space between adjacent vertebral bodies, and to methods for the implantation of such devices.

BACKGROUND OF THE INVENTION

A variety of spinal conditions including, for example, trauma, deformity, disease, or other degenerative conditions, may result in a person experiencing pain or limited physical mobility. This pain and reduced mobility is often attributed to the rupture or degeneration of the intervertebral discs resulting in compression of spinal nerve roots. Existing methods of treating these conditions include surgical decompression of the affected area of the spine, vertebral fusion, and nucleus replacements, with each technique generally requiring different implant devices and instrumentation.

One such technique employs the use of an interspinous implant device which is inserted between the spinous processes to distract or maintain the desired spatial relationship of the adjacent vertebrae. There are a number of limitations of existing interspinous implant devices, including the inability to accommodate the distinct anatomical structures of the spine, to minimize the subsidence and fracture potential, and to be inserted through minimally invasive surgical procedures.

Further, the success of existing methods often depends on the health of the annulus, which may be compromised during the surgical procedure or through the degenerative disc disease process. The annulus may have surgical incisions, tears or be poorly nourished and weak such that it cannot adequately serve, by itself, to restrain an implant device, such as a nucleus replacement device, within the confines of the annulus.

Accordingly, there is a need for improved implant devices positionable at multiple locations between adjacent vertebrae via minimally invasive surgical procedures that alleviate pain and other conditions caused by damage to or degeneration of the spine. Further, there is a need for interspinous and/or interlaminar implant devices able to accommodate the distinct anatomical structures of the spine, to minimize the subsidence and fracture potential, and to be inserted through minimally invasive surgical procedures and, in particular, procedures requiring only a single incision on one side of the spine. Further, there is a need for implant devices which may be utilized to assist in restraining an implant, particularly those that do not have other restraining features, in the intervertebral space.

The present invention may be used to fulfill these, as well as other needs and objectives, as will be apparent from the following description of embodiments of the present invention.

SUMMARY OF THE INVENTION

Thus, according to one aspect of the invention, an implant device is provided that is configured for implantation at multiple locations between adjacent vertebrae. In this manner, the implant device configuration provides several options with respect to implantation sites. The implant device comprises an implant body, a first portion of the implant body, and a second portion of the implant body. The second portion adjustably interconnected with the first portion such that the implant body has a compact orientation and an extended orientation. The adjustable interconnection also permits the implant body to be shifted from one orientation to the other orientation, enabling the implant body to be positioned in any one of areas between the spinous processes of the adjacent vertebrae, between laminar regions of the adjacent vertebrae, spanning an opening in the annulus between the adjacent vertebrae, or in the intervertebral space between the adjacent vertebrae.

According to another aspect of the invention, an implant device is provided for implantation between adjacent vertebrae. The implant device comprises an implant body, a first member of the implant body configured for engaging an adjacent vertebra, a second member of the implant body configured for engaging a vertebra, and an adjustable connection between the first and second members. The implant body is configured to pivot between a compact orientation, with the first and second members engaged with each other along predetermined portions thereof, and an extended orientation, with the predetermined portions of the first and second members pivoted away from each other. The implant body may be configured for being positioned in any one of areas between the spinous processes of the adjacent vertebrae, between laminar regions of the adjacent vertebrae, spanning an opening in the annulus between the adjacent vertebrae, and in the intervertebral space between the adjacent vertebrae.

In accordance with another aspect, a method is provided for implanting at least two implant devices at different locations between adjacent vertebrae. The method comprises implanting a first implant body having a first member, a second member, and an adjustable connection between the first and second members in any one of areas between the spinous processes of the adjacent vertebrae, between laminar regions of the adjacent vertebrae, spanning an opening in the annulus between the adjacent vertebrae, and in the intervertebral space between the adjacent vertebrae, and implanting a second implant body substantially similar to the first implant body in another one of the areas.

DETAIL DESCRIPTION OF THE PREFERRED EMBODIMENTS

Figure 1:
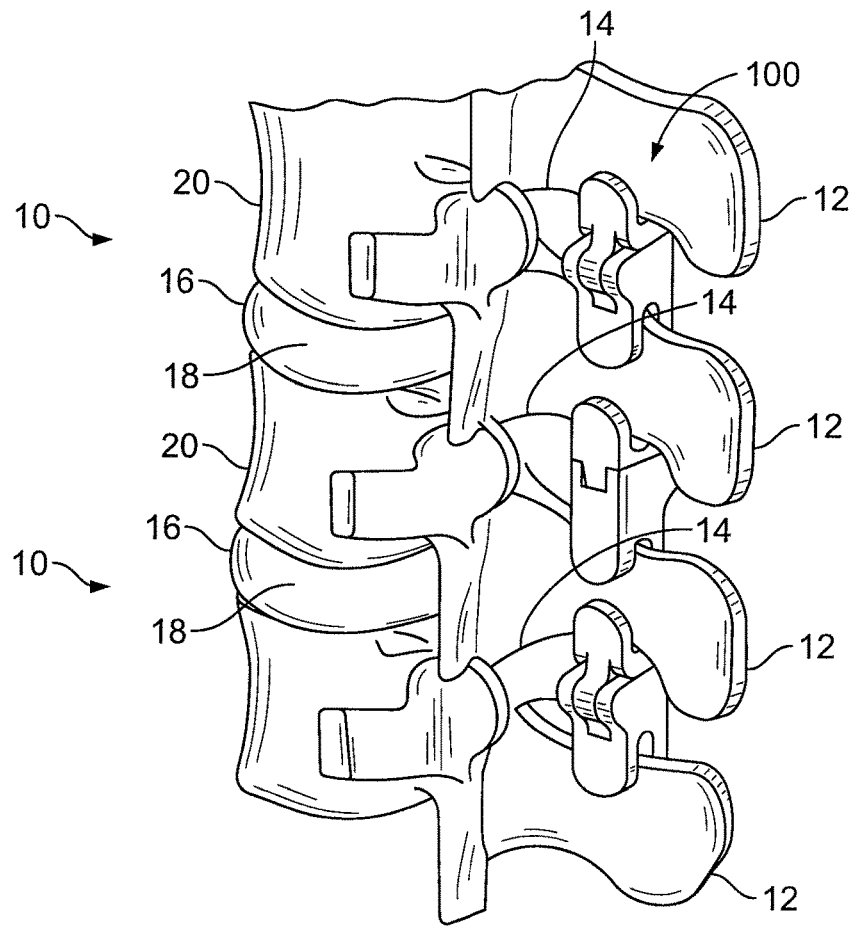
FIG. 1 is a perspective view of a portion of a human spine showing a series of an implant device in accordance with one aspect of the invention positioned between spinous processes of adjacent vertebrae.

With reference to FIGS. 1-26, an implant device is shown configured in accordance with various aspects of the invention for being implanted at multiple different locations between adjacent vertebrae 10, including, for example, between the spinous processes 12, between laminar regions 14, in an opening in the annulus 16, and/or in the intervertebral space 18 between adjacent vertebral bodies 20.

Figure 4:
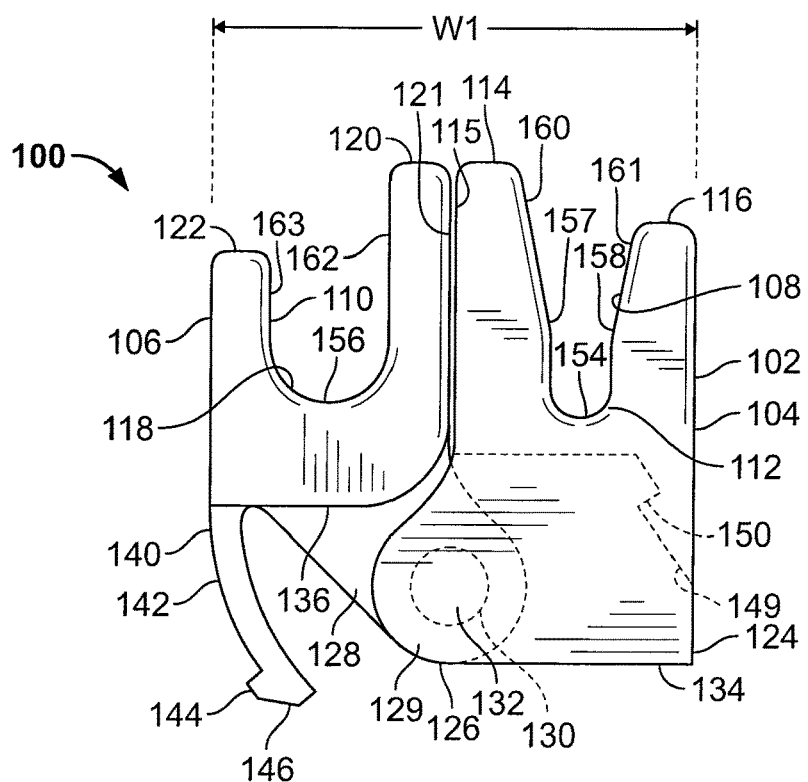
FIG. 4 is top plan view of the implant device of FIG. 1 shown in a compact orientation.
Figure 5:
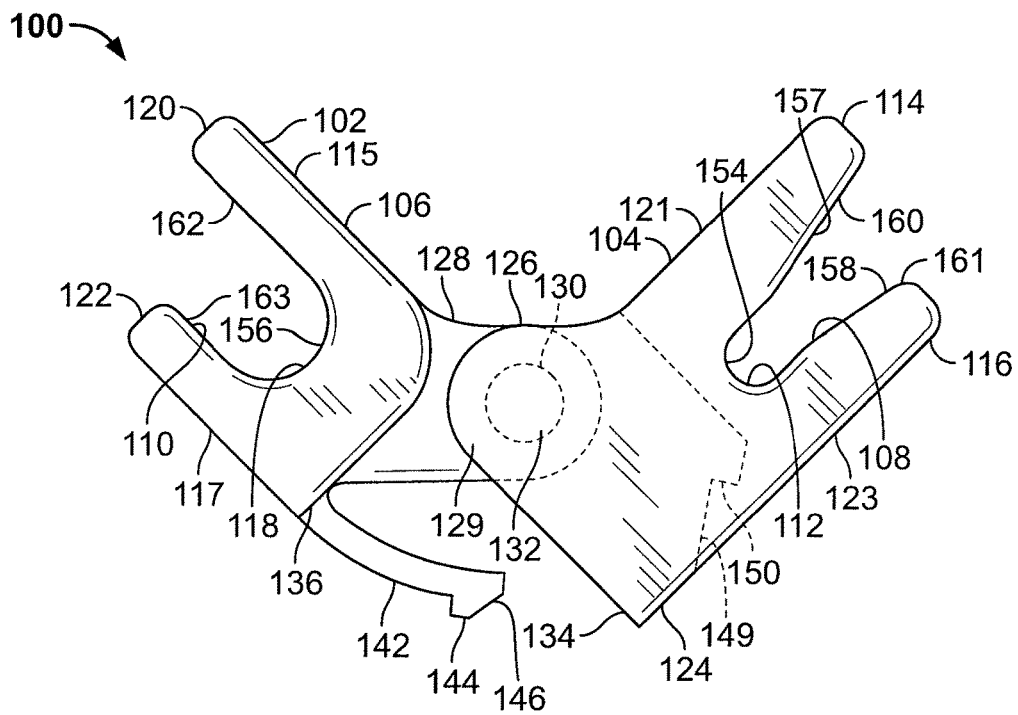
FIG. 5 is a top plan view of the implant device of FIG. 1 shown in an intermediate orientation.
Figure 6:
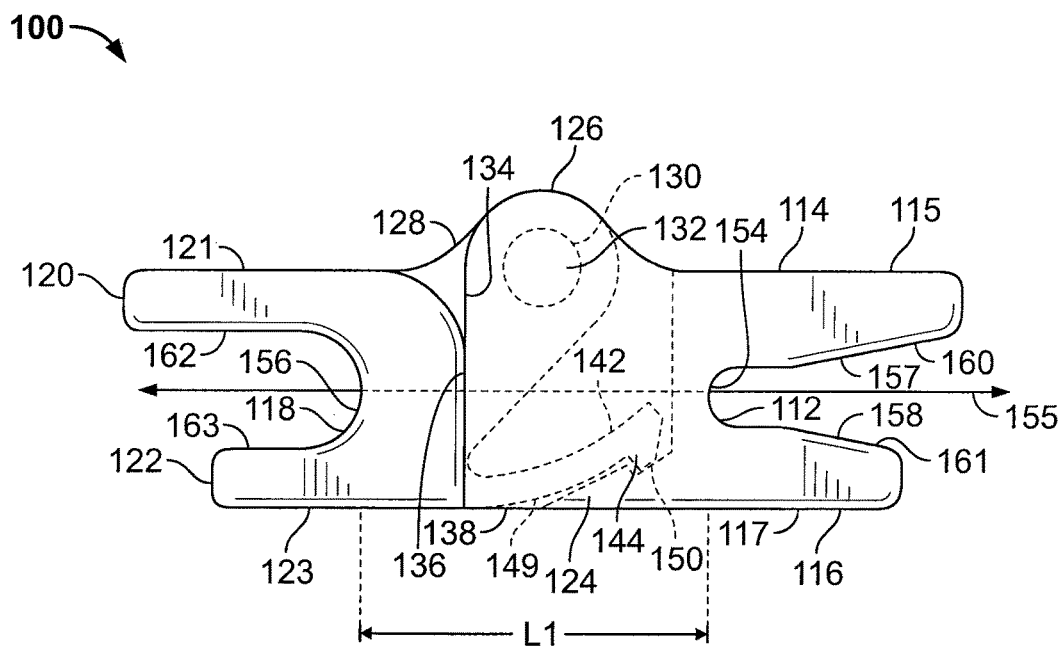
FIG. 6 is a top plan view of the implant device of FIG. 1 shown in an extended orientation.

With reference to FIGS. 1-6, implant device 100 is shown in accordance with one aspect of the invention. Implant device 100 comprises an implant body 102 configured for being positioned between spinous processes 12 of adjacent vertebrae 10. The implant body 102 includes a first portion or member 104 and a second portion or member 106 adjustably interconnected such that the implant body 102 can be arranged in a compact orientation (as shown in FIG. 4, for example), an extended orientation (as shown in FIG. 6, for example), or an intermediate orientation (as shown in FIG. 5, for example).

The first member 104 includes a first vertebral engaging portion 108, and the second member 106 includes a second vertebral engaging portion 110. As shown in FIG. 1, the first and second vertebral engaging portions 108, 110 are configured to receive a portion of the spinous processes 12 of the adjacent vertebrae 10. In one form, the vertebral engaging portions 108, 110 each have a unitary, one-piece construction with a generally U-shaped configuration, with the first vertebral engaging portion 108 including a first seat portion 112 extending between proximal ends of a first arm 114 and a second arm 116 and the second vertebral engaging portion 110 including a second seat portion 118 extending between proximal ends of a third arm 120 and a fourth arm 122.

The first member 104 additionally includes a spacer portion 124 generally extending from the first vertebral engaging portion 108. As shown in FIG. 6, for example, the spacer portion 124 is configured to provide a space between the first vertebral engaging portion 108 and the second vertebral engaging portion 110 when the implant body 102 is in the extended orientation.

Figure 2:
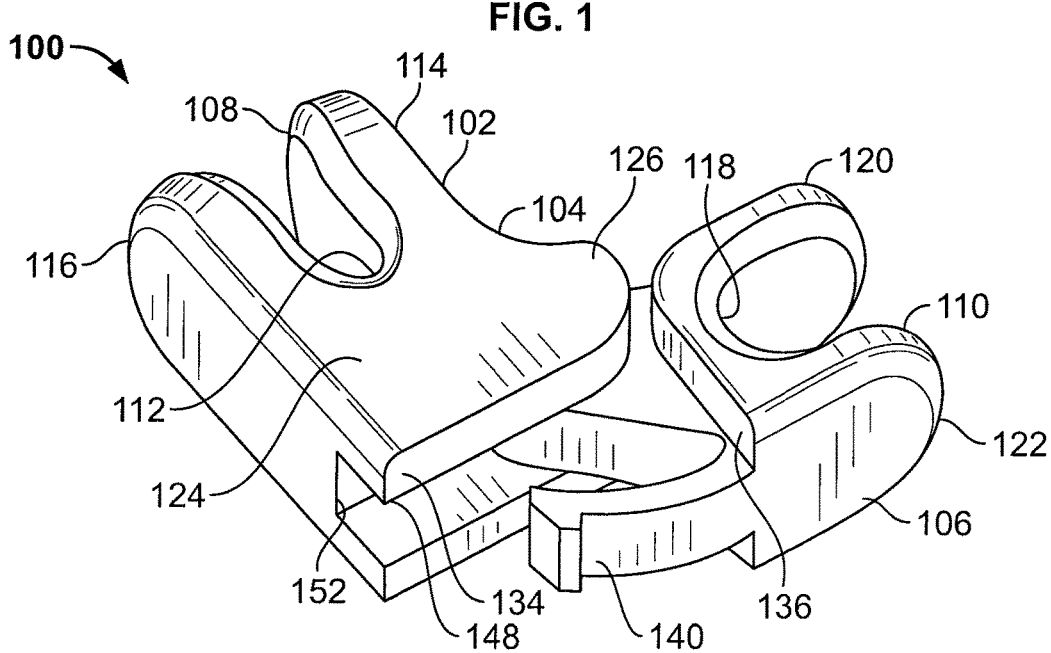
FIG. 2 is a perspective view of the implant device of FIG. 1.
Figure 3:
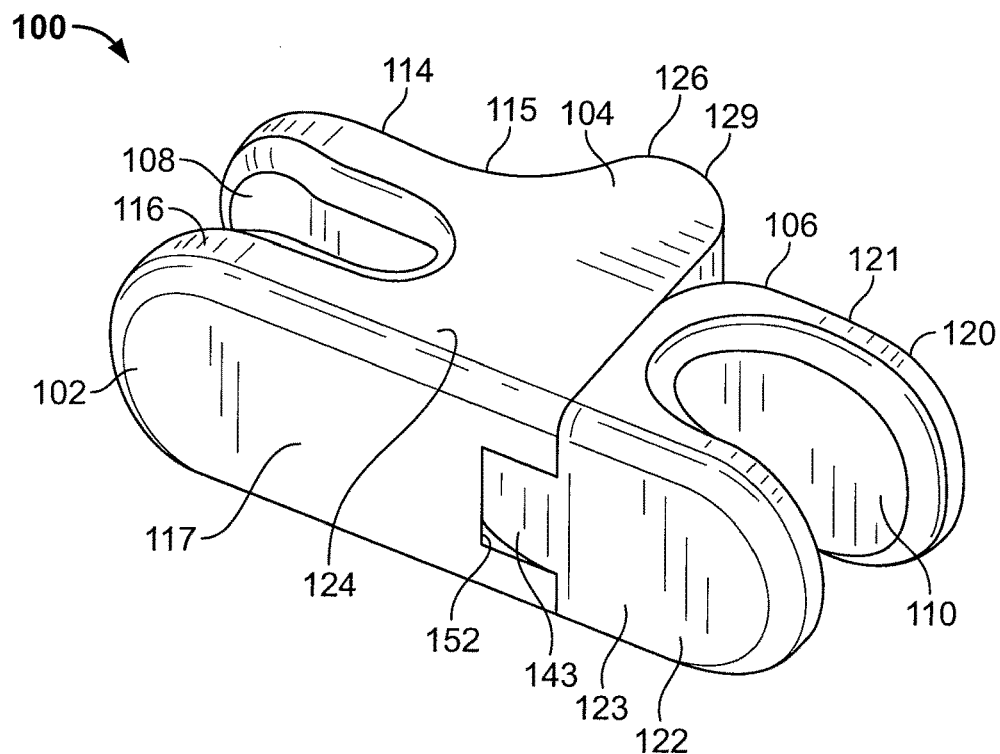
FIG. 3 is a perspective view of the implant device of FIG. 1 shown in another orientation.

As shown, for example, in FIGS. 4-6, the first member 104 and the second member 106 are pivotably coupled at an adjustable connection 126 such that the first and second members 104, 106 can freely shift between a predetermined compact orientation (FIG. 4) and a predetermined extended orientation (FIG. 6), with various intermediate orientations therebetween (such as shown in FIGS. 2 and 5). The adjustable connection contemplates a communication between two members and a pivot-type connection at a point of communication. Hereinafter, the terms pivot, rotate, and shift are interchangeably used and contemplate any reorientation or repositioning of an implant device, such as from a compact orientation to an extended orientation. The second member 106 has a boss portion 128 including an opening 130 therethrough for receiving a pin 132 coupled to a projecting portion 129 of the first member 104. Preferably, as illustrated in FIG. 6, the adjustable connection 126 is offset from surfaces 115, 121 of the first and third arms 114, 120 that are aligned when the implant body 102 is in the extended orientation. As described further hereinafter, the offset adjustable connection 126 optimizes the range of motion of the first and second members 104, 106 toward the compact orientation (FIG. 4).

As illustrated in FIG. 4, the compact orientation and the extended orientation are defined by the interfering engagement between the first member 104 and the second member 106. More specifically, in the compact orientation, a stop arrangement is formed by the first and third arms 114, 120 via substantially flat surfaces 115, 121 that can be pivoted into substantially flush engagement with each other so that the surface 115 of the first arm 114 of the first member 104 abuttingly engages the surface 121 of the third arm 120 of the second member 106. Similarly, in the extended orientation, a stop arrangement is provided via a stop surface 134 of the first member 104 extending generally perpendicular to the surface 115 and a stop surface 136 of the second member 106 extending generally perpendicular to the surface 121 such that when the first and second members 104, 106 are pivoted into the extended orientation the stop surface 134 abuttingly engages the stop surface 136.

As shown in FIG. 6, with the implant body 102 in the extended orientation, surfaces 117, 123 of the second and fourth arms 116, 122 are in-line with each other. The alignment of the second arm 116 and the fourth arm 122, along with the engagement of surfaces 134, 136 forms a load bearing wall 138 which extends the length of the implant body 102. Such a configuration promotes stability of the implant body 102 by directing the majority of a compressive load applied to the implant body 102 to the load bearing wall 138, thereby shielding the adjustable connection 126 from such load and directing the compressive load to a portion of the impact body 102 which resists reconfiguration of the implant body 102 to the compact orientation.

According to another form, the pin 132 is made from a radio-opaque material visible by radiographic imaging. Any number of radio-opaque markers may be incorporated and/or embedded in the implant body 102. The pin 132 and/or optional radio-opaque markers may be formed of any suitable radio-opaque material, including tantalum, for example.

As shown, for example, in FIGS. 2-6 the implant body 102 includes a securing mechanism 140 configured to secure the implant body 102 in the extended orientation. As illustrated, the second member 106 includes an arm 142 with a locking projection 144 at a distal end 146 of the arm 142. As the first and second members 104, 106 are pivoted toward the extended orientation, the arm 142 is received in the first member 104. More specifically, the arm 142 is received in an opening 148 formed in the spacer portion 124, generally facing the second member 106 (FIG. 2), and cams against an interior ramp surface 149 (FIGS. 4-6) towards an internal lock recess 150. As shown, in FIG. 6, in the extended orientation, the locking projection 144 fits into the internal lock recess 150 to secure the implant body 102 in the orientation.

Preferably, the arm 142 is resiliently deflectable, such that the locking projection 144 can be released from the internal lock recess 150 to allow the first and second members 104, 106 to be pivoted from the extended orientation to the compact orientation if desired. In one form, the first member 104 includes a notch 152 (FIG. 3) formed in the surface 117 so that a force (with an instrument, for example) may be applied to a portion 143 of the arm 142 exposed within the notch 152 to release the projection 144 from internal lock recess 150 thereby permitting the first and second members 104, 106 to pivot toward the compact orientation. The securing mechanism 140 may alternatively include a ratchet mechanism (not shown) that allows the implant body 102 to be incrementally pivoted between the compact orientation and the extended orientation. In this regard, cooperating teeth can be formed on the interior ramp surface 149 for this purpose.

With reference to FIGS. 1 and 4, the implant body 102 (as well as the other implant bodies described hereinafter configured for being positioned between spinous processes 12 or laminar regions 14) is configured to be inserted between the spinous processes 12 of adjacent vertebrae 10 in the compact orientation and, once it is in the interspinous space 18, pivoted to the extended orientation. So configured, the implant body 102 (as well as the others) can advantageously be inserted via minimally invasive procedures requiring only a single incision on one side of the spinous process 12.

In one form, an aperture is formed in the interspinous ligament (or the interlaminar ligament, in the case of the interlaminar devices discussed below) with the aperture sized to accommodate insertion of the implant body 102 therethrough in the compact orientation. Providing such an aperture in the ligament advantageously allows the remainder of the ligament to remain intact. In another form, the size and/or shape of the aperture formed in the ligament may be selected to correspond to the size and/or shape of the implant body 102. The length of the aperture is preferably less than the length L1 (shown in FIG. 6) of the portion of the implant body 102 between the first and second seat portions 112, 118 in the extended orientation. For example, the length of the aperture may be less than approximately 90% of the length L1. A specialized cutting instrument (not shown) may be utilized to provide such an aperture having a predetermined shape and/or size generally corresponding to the implant body 102.

According to another form, the implant body 102 is inserted between the spinous processes 12 with the arms 114, 116, 120, 122 leading the implant body 120 into the interspinous space. The arms 114, 116, 120, 122 are configured to penetrate the interspinous ligament between adjacent spinous processes 12 (or an aperture formed therein) and to distract the ligament as the first member 104 and second member 106 are pivoted to the extended orientation.

The arms 114, 116 and 120, 122 may have any suitable length to accommodate a portion of the spinous process 12 therebetween. As shown in FIG. 4, the first arm 114 may be longer than the second arm 116 and the third arm 120 longer than the fourth arm 122. So configured, the first and third arms 114, 120 act as leading arms which are inserted through an opening in the ligament between adjacent spinous processes 12. Upon insertion of the first and third arms 114, 120 the first and second members 104, 106 are pivoted to the extended orientation. Providing longer leading arms 114, 120 and shorter trailing arms 116, 122 advantageously promotes ease of insertion of the implant body 102 and minimizes the distance that the interspinous ligament must be distracted to pivot the first and second members 104, 106 to the extended orientation. In this form, the size of the opening can be smaller that that of the width W1 (FIG. 4) of the compactly oriented implant body 102 since the leading arms distract the opening during pivoting of the implant body 102.

Figure 7:
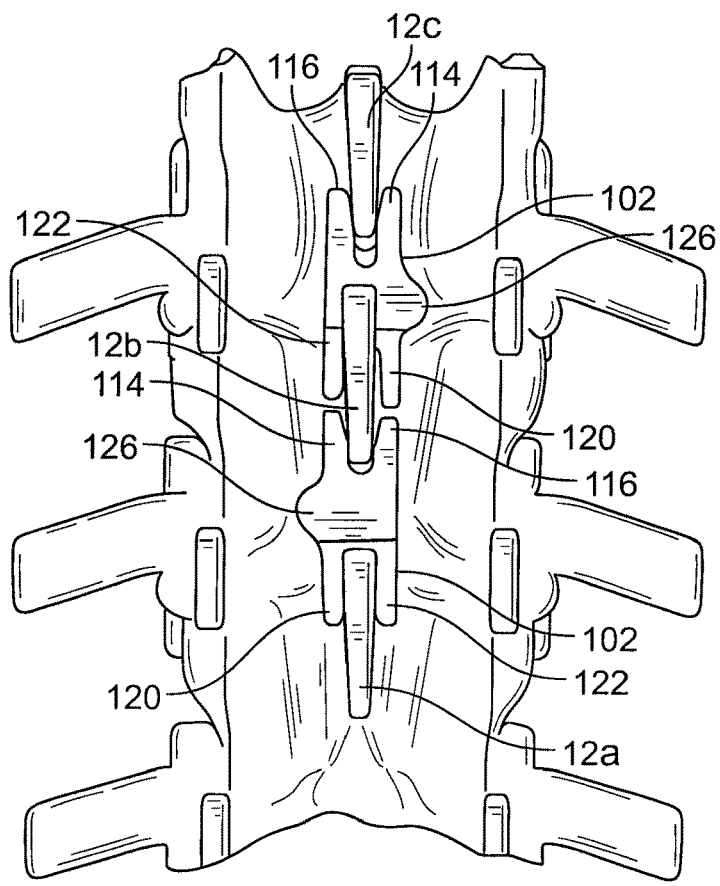
FIG. 7 is an elevation view of a posterior portion of a human spine showing two of the implant devices of FIG. 2 positioned between adjacent spinous processes in a mirror-image orientation.
Figure 8:
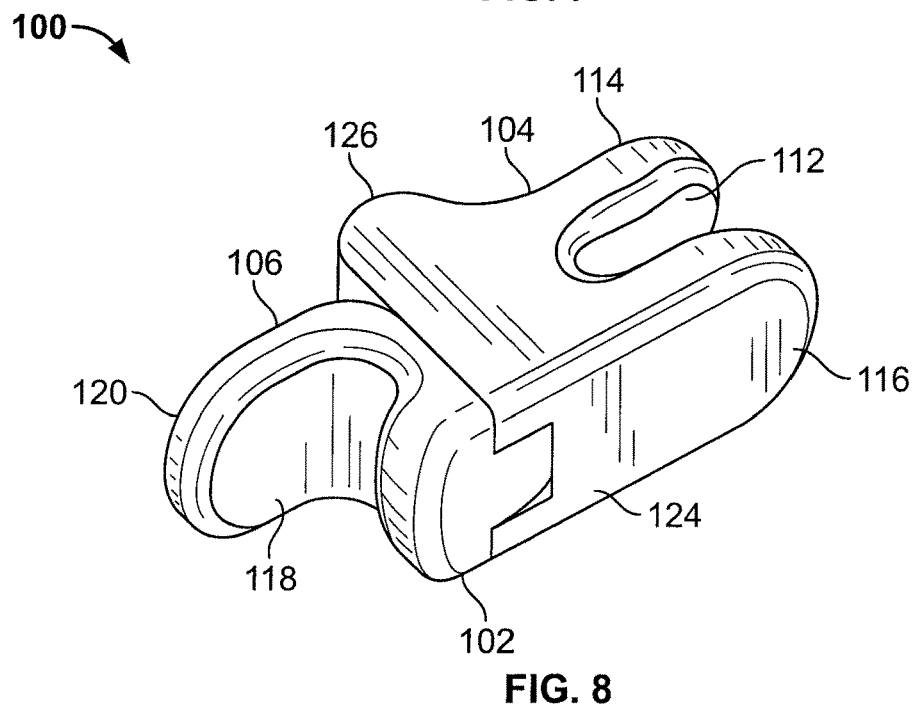
FIG. 8 is a perspective view of an implant device in accordance with another aspect of the invention.
Figure 9:
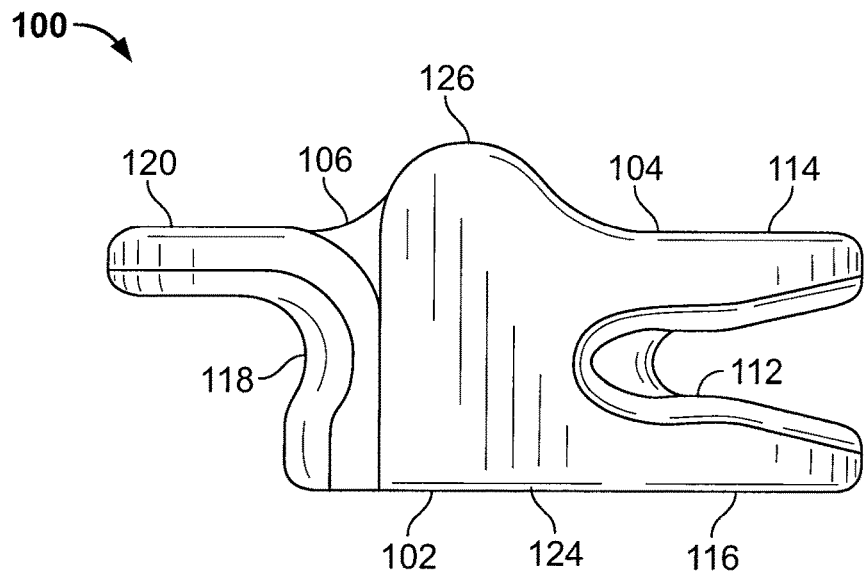
FIG. 9 is a top plan view of the implant device of FIG. 8.
Figure 25:
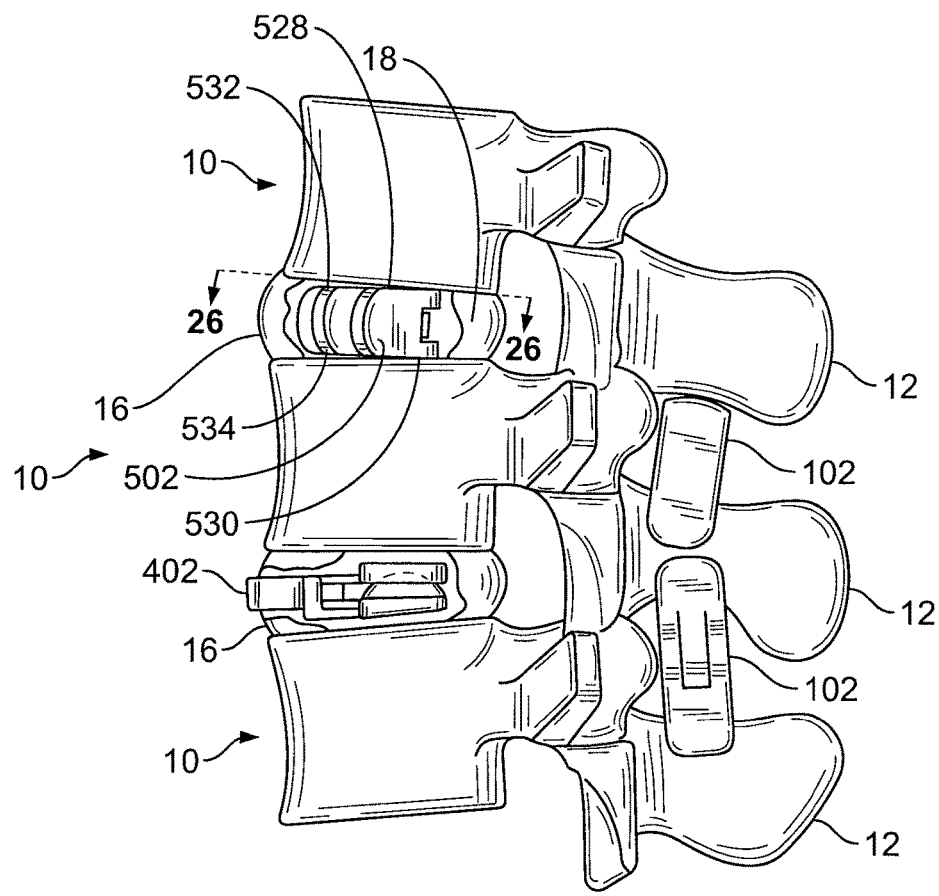
FIG. 25 is a partial cut-away view of a portion of a human spine showing the implant device of FIG. 1, the implant device of FIG. 8, the implant device of FIG. 18, and an implant device in accordance with another aspect of the invention positioned at different locations of the spine.

As shown in FIG. 7, another advantage to providing longer leading arms 114, 120 and shorter trailing arms 116, 122 is that multiple implant bodies 120 may be stacked in series between three or more spinous processes 12a-c, with the adjacent implant bodies 102 arranged in a mirror image, or flipped, orientation. In other words, the first implant body 102 is positioned between the adjacent spinous processes 12a and 12b with the longer leading arms 114, 120 on the left side of the spinous processes 12, and the second implant body 102 is positioned between the adjacent spinous processes 12b and 12c with the longer leading arms 114, 120 on the right side of the spinous processes 12, thereby preventing undesirable contact between the implant bodies 102. In still another form, as shown in FIGS. 8-9, one or more of the leading arms 114, 120 and/or trailing arms 116, 122 may be eliminated (as shown in FIGS. 8, 9, and 25) to enhance the ability to stack the implant bodies 102 as described above.

With the implant body 102 positioned between the spinous processes 12 in the extended orientation, the first vertebral engaging portion 108 receives a portion of one of the spinous processes 12, the second vertebral engaging portion 110 receives a portion of the other spinous process 12, and the spacer portion 124 extends therebetween. As illustrated in FIGS. 1 and 7, in one form, the first seat portion 112 of the first vertebral engaging portion 108 includes a first concave portion 154 which receives the superior portion of the inferior spinous process 12 with the first arm 114 and the second arm 116 located on opposite sides of the spinous process 12. Similarly, the second seat portion 118 of the second vertebral engaging portion 110 includes a second concave portion 156 which receives the inferior portion of the superior spinous process 12 with the third arm 120 and the fourth arm 122 located on opposite sides of the spinous process 12.

Thus, the implant body 102 is preferably configured to space adjacent spinous processes 12 apart from one another to the desired spatial relationship with the first vertebral engaging portion 108 engaging one of the spinous processes 12 and the second vertebral engaging portion 110 engaging an adjacent spinous process 12. In one form, the implant body 102 is sized to distract the spinous processes 12.

A number of differently sized implant bodies 102 can be provided to accommodate the distinct anatomies of individual patients. In addition, a number of differently sized first members 104 and second members 106 may be interchangeably coupled to provide a variety of differently sized and configured implant bodies 102.

Preferably, at least one of the seat portions 112, 118 is configured to allow for substantially flush engagement with a portion of the spinous process 12. More specifically, the first and second arms 114, 116 and/or the third and fourth arms 120, 122 are configured to substantially engage the spinous process 12, which advantageously reduces the potential for undesirable bone subsidence and fracture.

As shown in FIG. 6, in one form, the concave portion 154 of the first seat portion 112 is smaller than the concave portion 156 of the second seat portion 118. More specifically, the distance between the opposing interior surfaces 157, 158 of the first and second arms 114, 116 is less than the distance between the opposing interior surfaces 162, 163 of the third and fourth arms 120, 122. Additionally, the interior surfaces 157, 158 include first and second slanted surfaces 160, 161 that are angled outward from a central axis 155 extending through the concave portions 154, 156. The distance between the opposing interior surfaces 157, 158 and the angles of the first and second outwardly slanted surfaces 160, 161 from the central axis 155 are preferably selected to permit the seat portion 112 to accommodate the distinct anatomical geometry of a portion of the spinous process 12 and thereby provide a substantially flush engagement between the seat portion 112 and a portion of one of the spinous processes 12, preferably, the superior portion of the inferior spinous processes 12.

Figure 12:
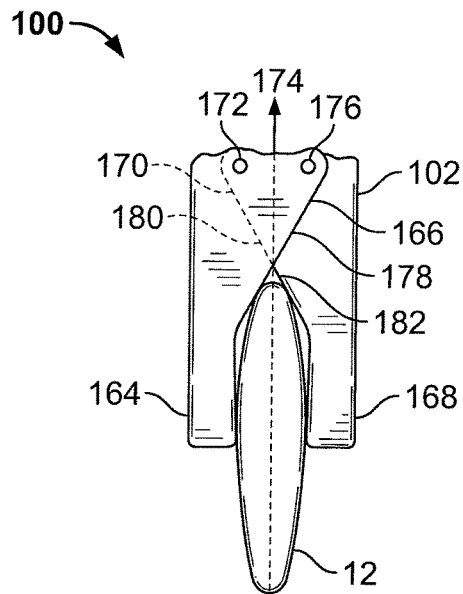
FIG. 12 is a fragmentary view of an implant device in accordance with another aspect of the invention.

In another form, one of the first and second seat portions 112, 118 includes a left arm 164 having a first wing portion 166 and a right arm 168 having a second wing portion 170. As illustrated in FIG. 12, a central axis 174 extends through the implant body 102 between the left and right arms 164, 168. The left and right wing portions 166, 170 comprise angled surfaces 178,180 which extend towards the arms 164, 168 across the central axis 174 to form a triangle-shaped seat portion 182. The left wing portion 166 is pivotably coupled to the implant body 102 at a first pivot 172, the first pivot 172 being located on the same side of the central axis 174 as the left arm 164. The right wing portion 170 is pivotably coupled to the implant body 102 at a second pivot 176, the second pivot 176 being located on the same side of the central axis 174 as the right arm 168. The first pivot 172 is configured such that when a spinous process 12 engages the seat portion 182, and more specifically engages the angled surface 178 of the left wing portion 166, the point at which the force is exerted by the spinous process 12 on the angled surface 178 is closer than the first pivot 172 to the central axis 174. Therefore, the force exerted by the spinous process 12 on the angled surface 178 of the left wing portion 166 will cause the left arm 164 to pivot around the first pivot 172 such that the distal end of the left arm 164 travels toward the central axis 174 and engages the spinous process 12. Similarly, the second pivot 176 is configured such that when a spinous process 12 engages the seat portion 182, and more specifically engages the angled surface 180 of the right wing portion 170, the point at which the force is exerted by the spinous process 12 on the angled surface 180 is closer than the second pivot 176 to the central axis 174. Therefore, the force exerted by the spinous process 12 on the angled surface 180 of the right wing portion 170 will cause the right arm 168 to pivot around the second pivot 176 such that the distal end of the right arm 168 travels toward the central axis 174 and engages the spinous process 12. Therefore, the insertion of the spinous process 12 will result in the left and right arms 164, 168 pinching the spinous process 12 therebetween.

Figure 13:
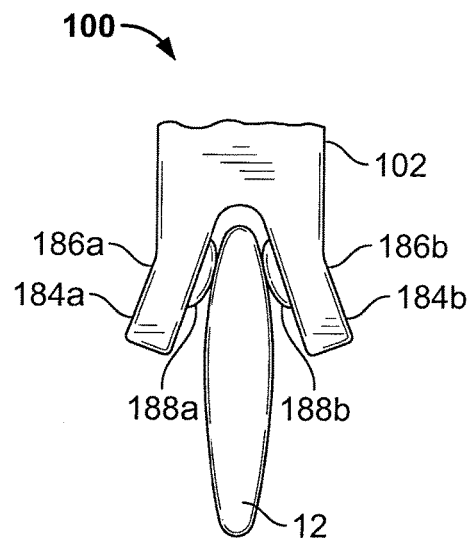
FIG. 13 is a fragmentary view of an implant device in accordance with another aspect of the invention.

In yet another form, illustrated in FIG. 13, for example, one of the first and second seat portions 112, 118 includes arms 184a,b having outwardly angled portions 186a,b with wedging pads 188a,b that can wedge against the sides of the spinous process 12 as it is received in the seat portion 112,118.

Figure 10:
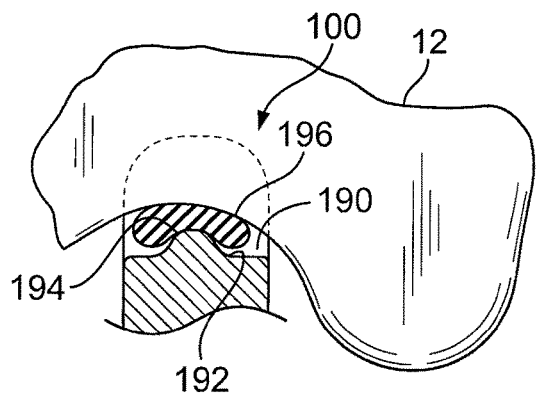
FIG. 10 is a partial cut-away view of an implant device in accordance with another aspect of the invention.
Figure 11:
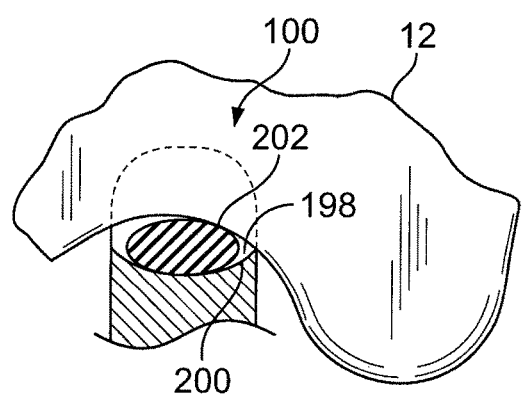
FIG. 11 is a partial cut-away view of an implant device in accordance with another aspect of the invention.

In yet another form, the implant body 102 and/or the interface between the implant body 102 and the vertebrae 10 is configured to provide compliance to accommodate natural motion that may take place at the site. For example, in one form, at least one of the seat portions 112, 118 include an interface portion configured to provide compliance to the seat portion. In one form, as shown in FIG. 10, an interface portion 190 includes a ball portion 192 and a socket portion 194 defined in a pad 196 that is moveable with respect to the ball portion 192. Thus, when the edge of the spinous process 12 is received in the interface portion 190, it contacts the movable pad 196 instead of a rigid surface. In another form, as shown in FIG. 11, an interface portion 198 includes a dish portion 200 and pad portion 202 that is moveable within the dish portion 200. When the edge of the spinous process 12 is received in the interface portion 198, it contacts the movable pad portion 202 instead of a rigid surface.

Figure 14:
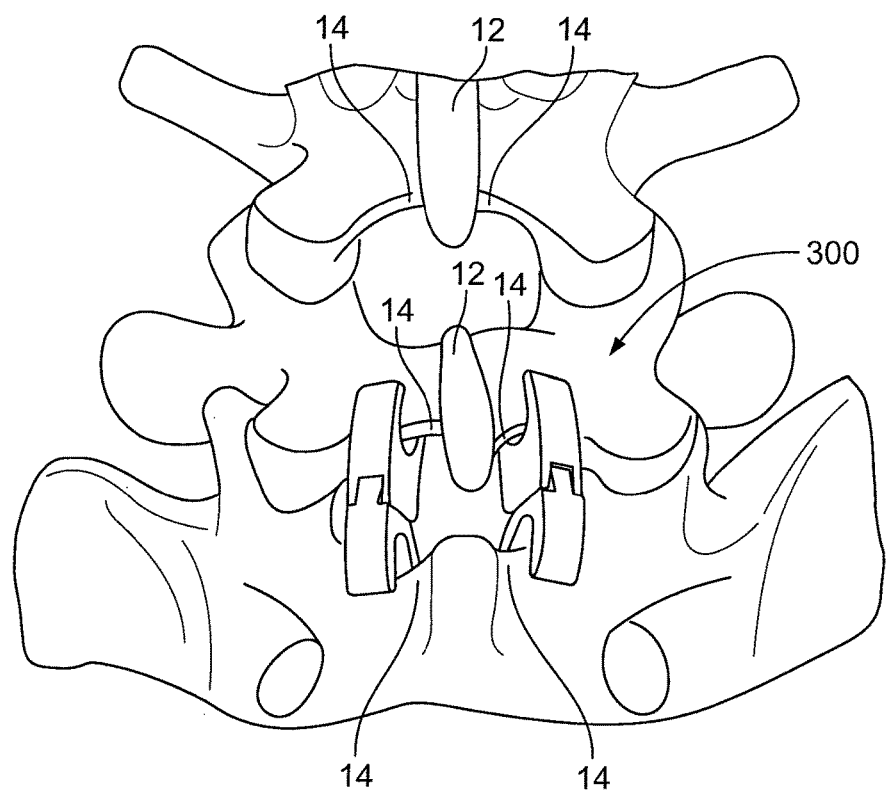
FIG. 14 is an elevation view of a portion of a human spine showing two implant devices in accordance with another aspect of the invention positioned between laminar regions of adjacent vertebrae.
Figure 15:
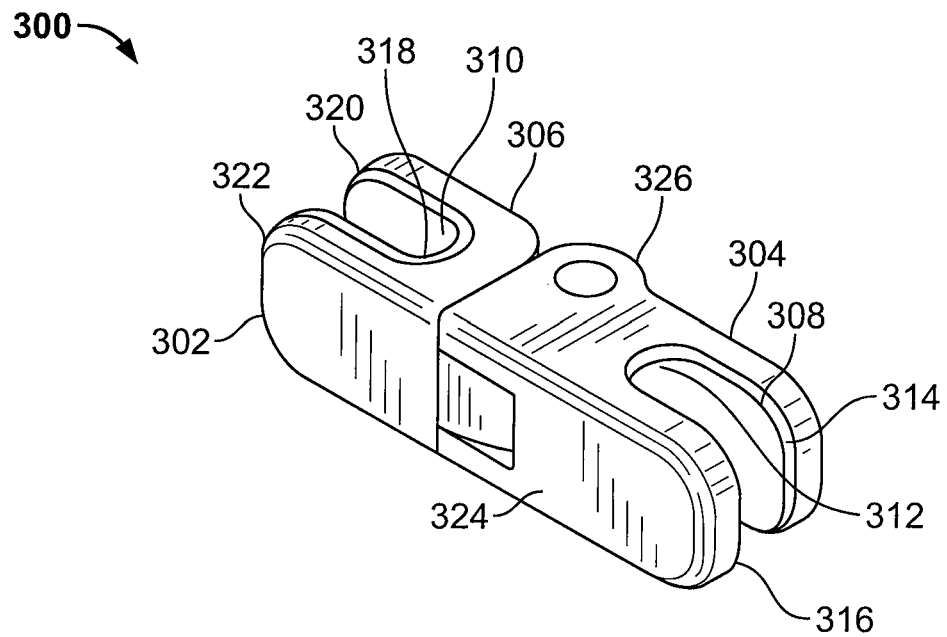
FIG. 15 is a perspective view of the implant device of FIG. 14.

With reference to FIGS. 14-17, an implant device 300 is shown in accordance with another aspect of the invention. Implant device 300 includes an implant body 302 that is substantially similar to implant body 102. Accordingly, only the differences will be set forth in detail herein. As illustrated in FIG. 14, implant body 302 is configured for positioning between laminar regions 14 of the adjacent vertebrae 10. Implant body 302 includes a first member 304 and a second member 306 including a first vertebral engaging portion 308 and a second vertebral engaging portion 310, respectively.

Figure 17:
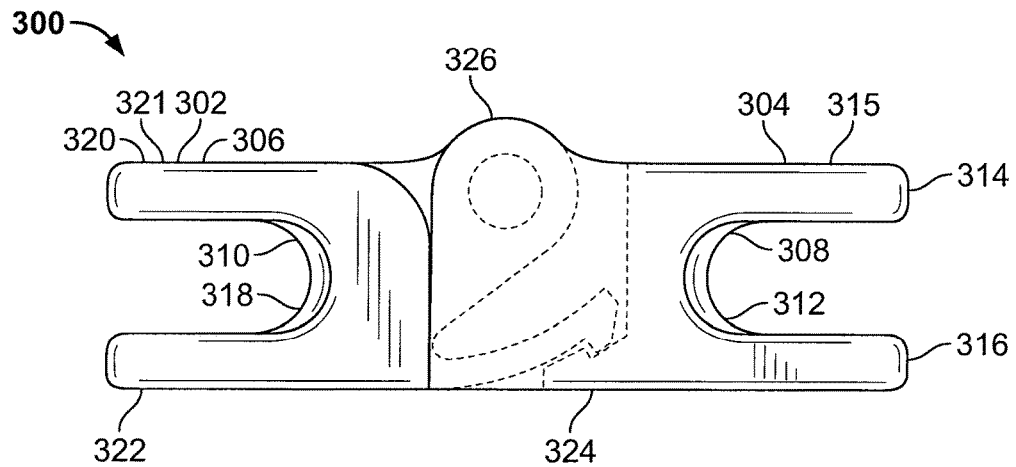
FIG. 17 is a top plan view of the implant device of FIG. 14 shown in an extended orientation.

The first and second vertebral engaging portions 308, 310 have a generally U-shape configuration to receive a portion of the laminar regions 14 of the adjacent vertebrae 10. More specifically, as shown in FIG. 17, the first vertebral engaging portion 308 includes a first seat portion 312 extending between proximal ends of a first arm 314 and a second arm 316. Similarly, the second vertebral engaging portion 310 includes a second seat portion 318 extending between proximal ends of a third arm 320 and a fourth arm 322.

In a preferred form, at least one of the seat portions 312, 318 is configured to allow for substantially flush engagement with a portion of the laminar region 14. More specifically, the first and second arms 314, 316 and/or third and fourth arms 320, 322 are configured to substantially engage the laminar region 14, which advantageously reduces the potential for undesirable bone subsidence and fracture. In another form, at least one of the seat portions 314, 316 may include an interface portion (See FIGS. 63-67; 111-127) configured to provide compliance to the seat portion 314, 316 to accommodate natural motion that may take place at the site.

Figure 16:
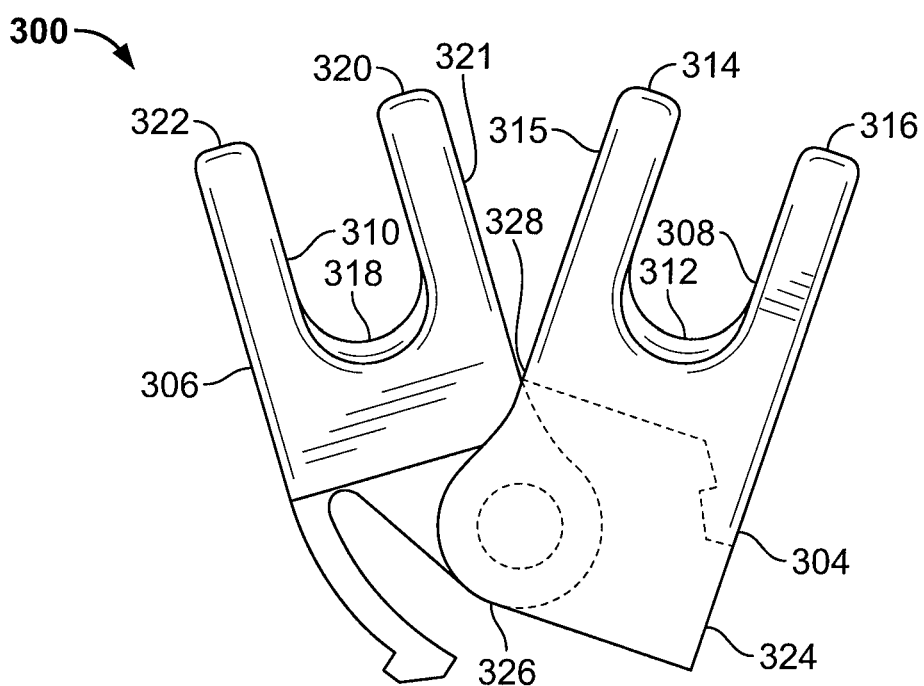
FIG. 16 is a top plan view of the implant device of FIG. 14 shown in a compact orientation.

As with the implant body 102, the first member 304 and the second member 306 are pivotably coupled at an adjustable connection 326 such that the first and second members 304, 306 can freely pivot between a compact orientation (FIG. 16) and an extended orientation (FIG. 17). The implant body 302 is configured to be inserted between adjacent laminar regions 14 in the compact orientation and then pivoted to the extended orientation. Also like implant body 302, the compact orientation and the extended orientation of implant body 102 are defined by the interfering engagement between the first member 304 and the second member 306. As can be seen in FIGS. 16 and 17, the adjustable connection 326 is offset a shorter distance from surfaces 315, 321 of the implant body 302 than the adjustable connection 126 is offset from the surfaces 115, 121 of the implant body 102. Accordingly, as illustrated in FIG. 16, in the compact orientation of implant body 302, a stop arrangement is provided by the first arm 314 of the first member 304 meeting the third arm 320 of the second member 306 at a stop point 328 rather than an abutting engagement of the arms as with implant body 102. So configured, in the compact orientation, implant body 302 advantageously promotes ease of insertion through the tissue between the adjacent laminar regions 14 and minimizes the distance that the tissue must be distracted to pivot the first and second members 304, 306 to the extended orientation.

With reference to FIGS. 14 and 17, for example, the first member 304 includes a spacer portion 324 extending from the first vertebral engaging portion 308. The spacer portion 324 is configured to provide a space between the first vertebral engaging portion 308 and the second vertebral engaging portion 310 when the implant body 302 is in the extended orientation. Accordingly, the spacer portion 324 is preferably sized so that the implant body 302 spaces the laminar regions 14 apart to the desired spatial relationship with the implant body 302 positioned therebetween in the extended orientation. In one form, the implant body 302 is sized to distract the laminar regions 14 of the adjacent vertebrae 10. As with implant body 102, in another form, a number of differently sized implant bodies 302 are provided. In yet another form, a number of differently sized first members 304 and second members 306 may be interchangeably coupled to provide a variety of differently sized and configured implant bodies 302.

Figure 18:
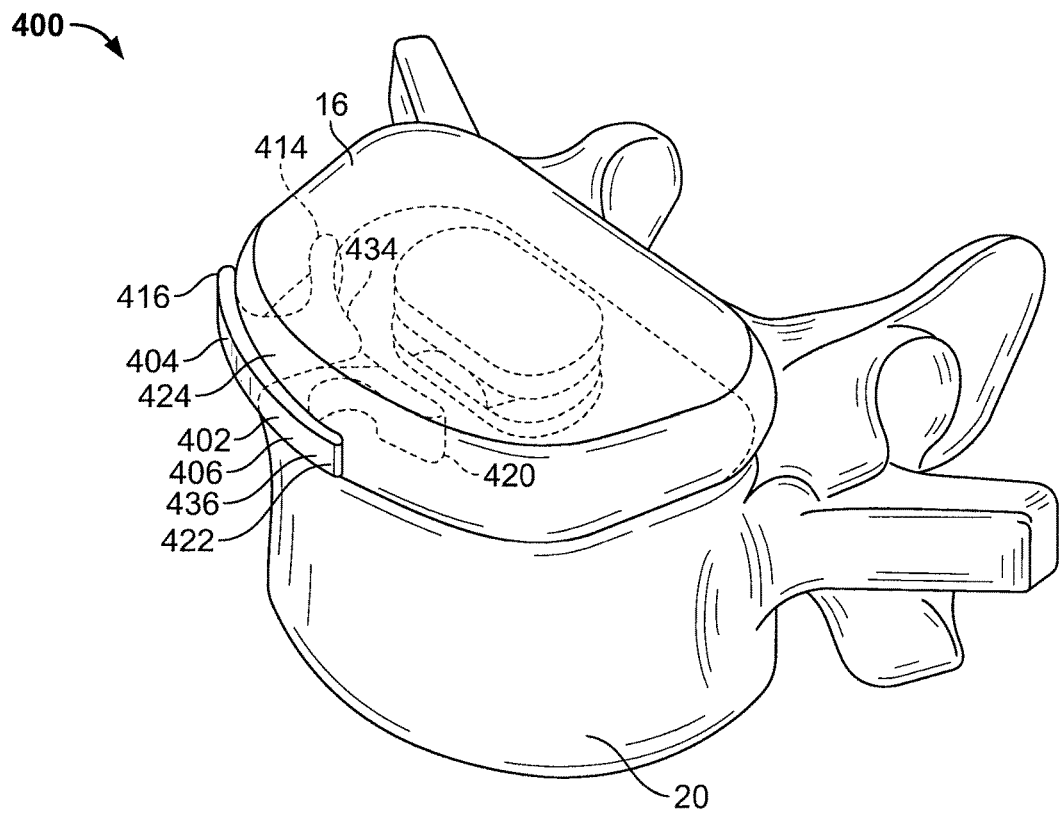
FIG. 18 is an elevation view of a portion of a human spine showing an implant device in accordance with another aspect of the invention positioned in an opening in the annulus above a vertebral body.
Figure 22:
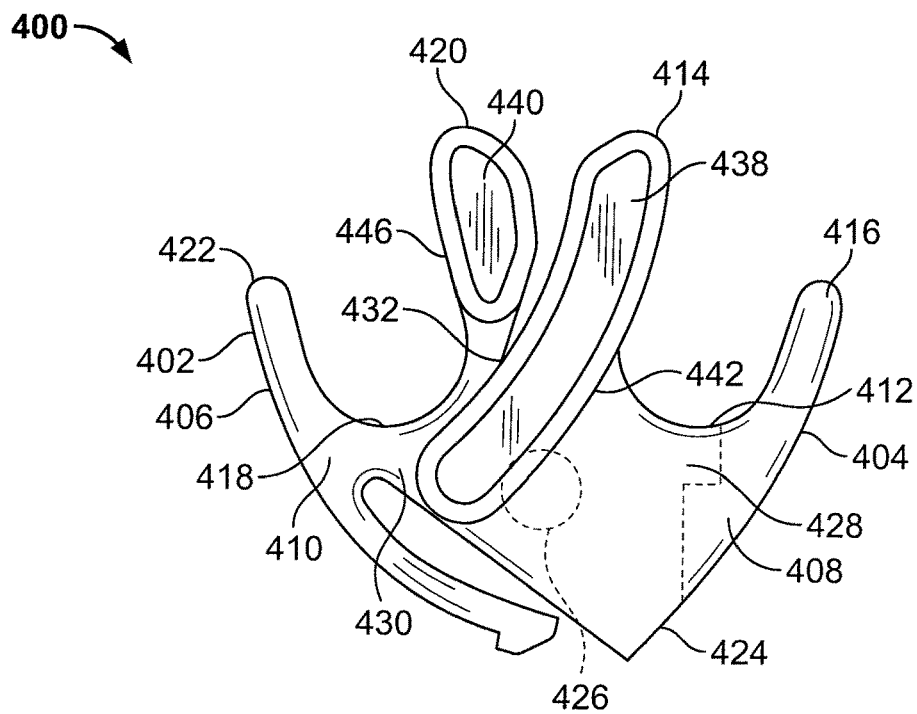
FIG. 22 is a bottom plan view of the implant device of FIG. 18 shown in a compact orientation.
Figure 23:
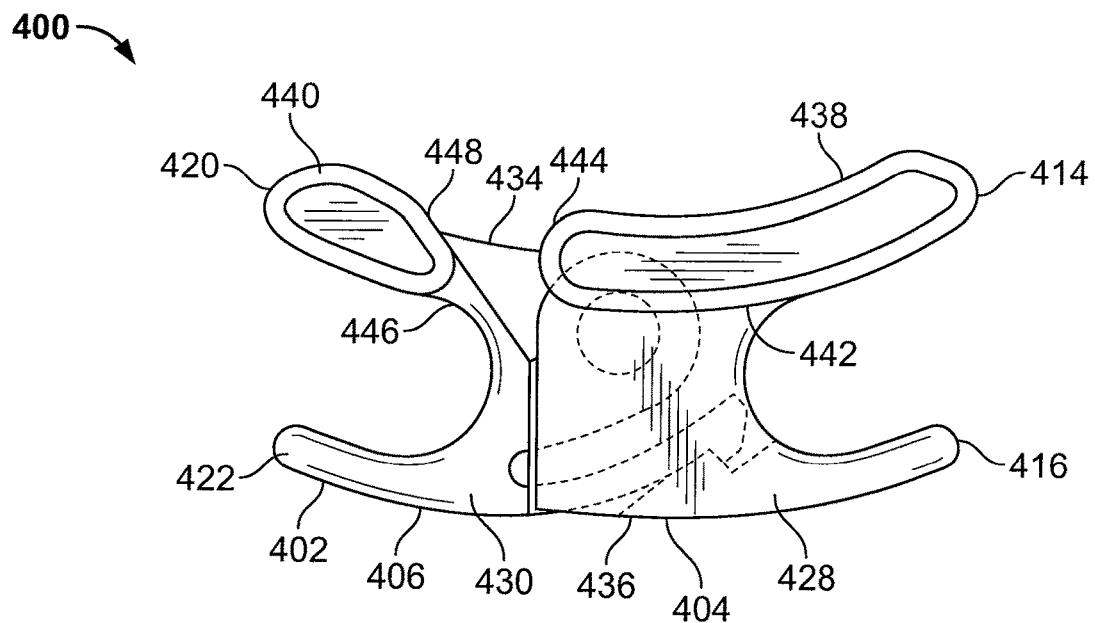
FIG. 23 is a bottom plan view of the implant device of FIG. 18 shown in an extended orientation.
Figure 24:
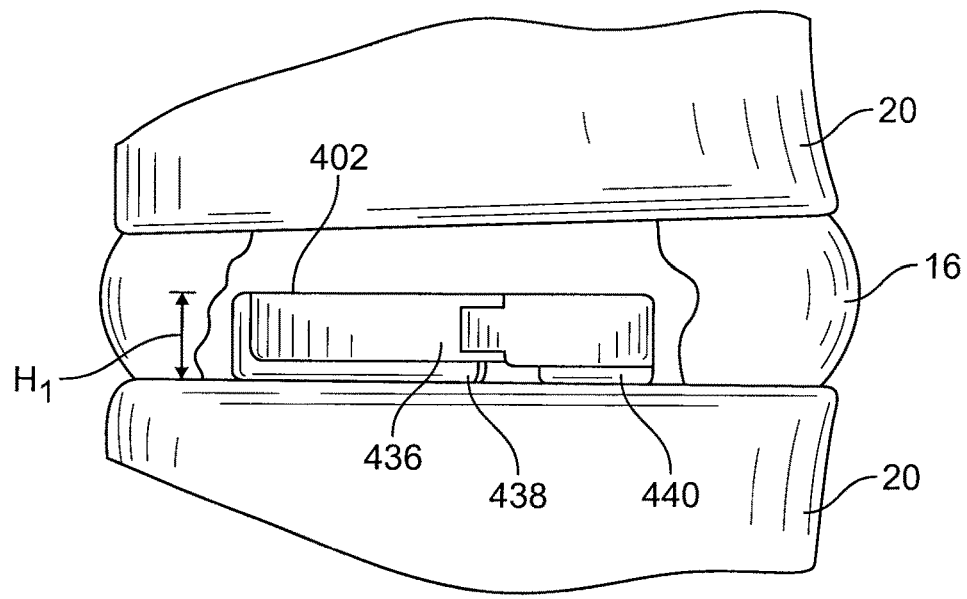
FIG. 24 is partial cut-away view of a portion of a human spine showing the implant device of FIG. 18 in an annulus between adjacent vertebral bodies.

With reference to FIGS. 18-24, an implant device 400 is shown in accordance with yet another aspect of the invention. Again, implant device 400 includes an implant body 402 that is substantially similar to implant body 102. Accordingly, only the differences will be set forth in detail herein. As illustrated in FIGS. 18 and 24, implant body 402 is configured to be positioned spanning an opening in the annulus 16 between the adjacent vertebrae 10.

Implant body 402 includes a first member 404 with a first vertebral engaging portion 408 and a second member 406 with a second vertebral engaging portion 410. The first vertebral engaging portion 408 includes a first lower portion 428 for engaging the inferior vertebral body 20, and a first seat portion 412 extending between proximal ends of a first arm 414 and a second arm 416. The second vertebral engaging portion 410 includes a second lower portion 430 for engaging the inferior vertebral body 20, and a second seat portion 418 extending between proximal ends of a third arm 420 and a fourth arm 422. A spacer portion 424 extends from the first seat portion 412 away from arms 414, 416.

Implant body 402 is configured to be inserted in an opening in the annulus 16 in a compact orientation (shown in FIG. 22) and pivoted about an adjustable connection 426 (shown in FIGS. 21 and 23) to an extended orientation (shown in FIG. 23), in which the spacer portion 424 spaces apart the first and second seat portions 412, 418. In one form, the implant body 402 is positioned in an opening in the annulus 16 with the spacer portion 424 spanning the opening, the first arm 414 and the third arm 420 positioned within the annulus 16, and the second arm 416 and the fourth arm 422 outside of the annulus 16. So positioned, the implant body 402 can advantageously restrain an implant device, such as an artificial nucleus device (as illustrated in FIG. 18), positioned in the intervertebral space 18.

Accordingly, the spacer portion 424 is preferably sized to plug an opening in the annulus 16. Additionally, as shown in FIG. 24, the implant body 402 preferably has a height H1 that is less than the distance between the adjacent vertebral bodies 20 such that the implant body 402 engages only the inferior vertebral body 20 when positioned in an opening in the annulus 16. In another form, a number of differently sized implant bodies 402 are provided. In yet another form, a number of differently sized first members 404 and second members 406 may be interchangeably coupled to provide a variety of differently sized and configured implant bodies 402.

As shown in FIG. 23, for example, the adjustable connection 426 is not offset from the implant body 402 like the adjustable connection 126 is offset from the implant body 102 as shown in FIG. 2. Accordingly, as illustrated in FIG. 22, the compact orientation of implant body 402 is defined by the first arm 414 of the first member 404 meeting the third arm 420 of the second member 406 at a stop point 432, rather than an abutting engagement of the arms as in implant body 102. So configured, in the compact orientation implant body 402 advantageously promotes ease of insertion of the arms 414, 420 through the opening in the annulus 16 and minimizes any further distraction of the opening to pivot the first and second members 404, 406 to the extended orientation.

Figure 19:
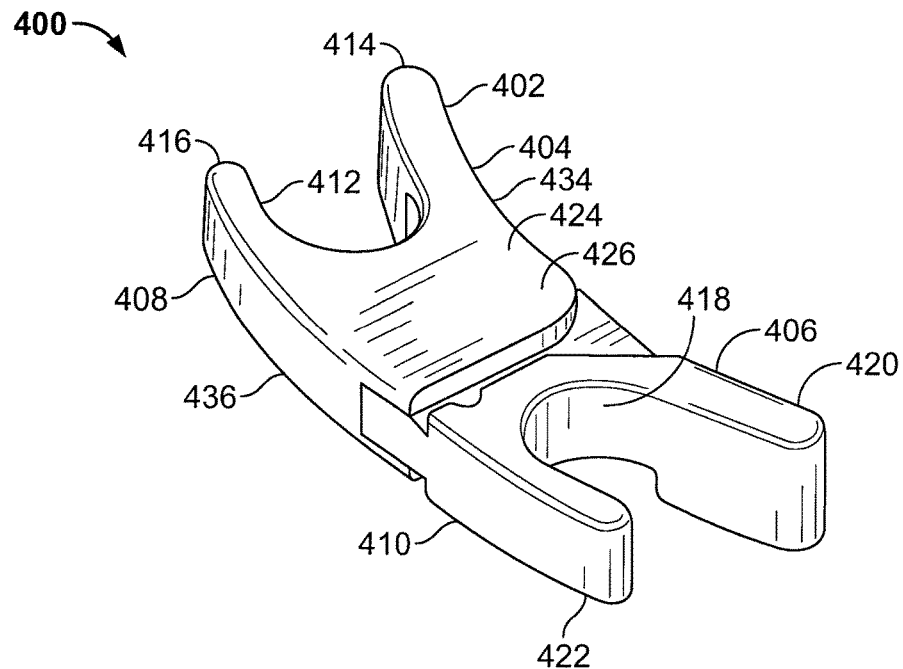
FIG. 19 is a perspective view of the implant device of FIG. 18.
Figure 20:
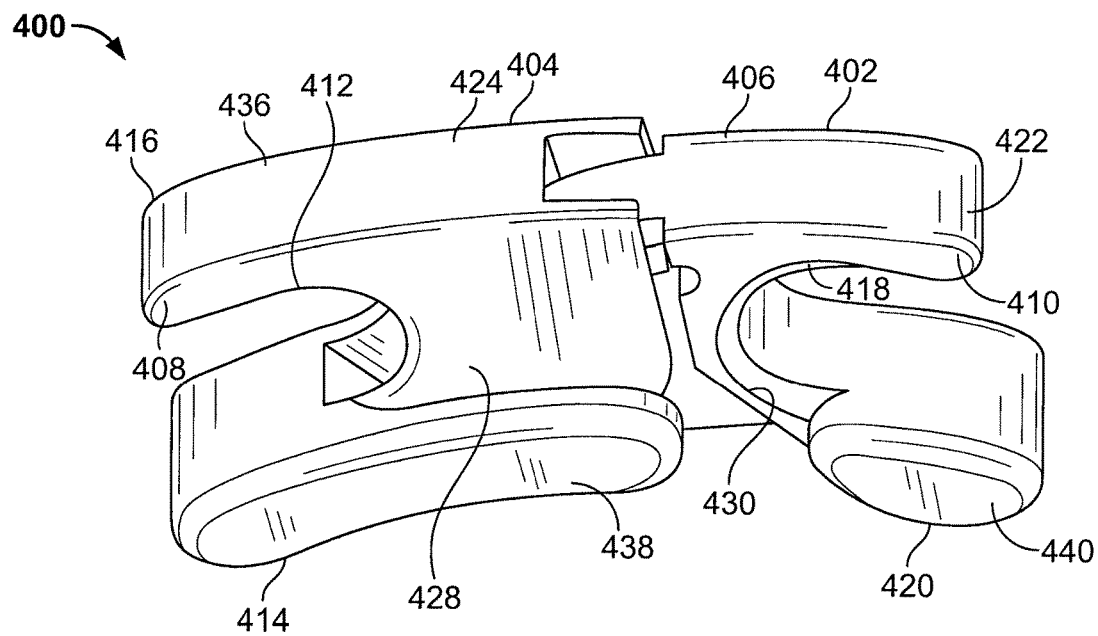
FIG. 20 is an elevation view of the implant device of FIG. 18.
Figure 21:
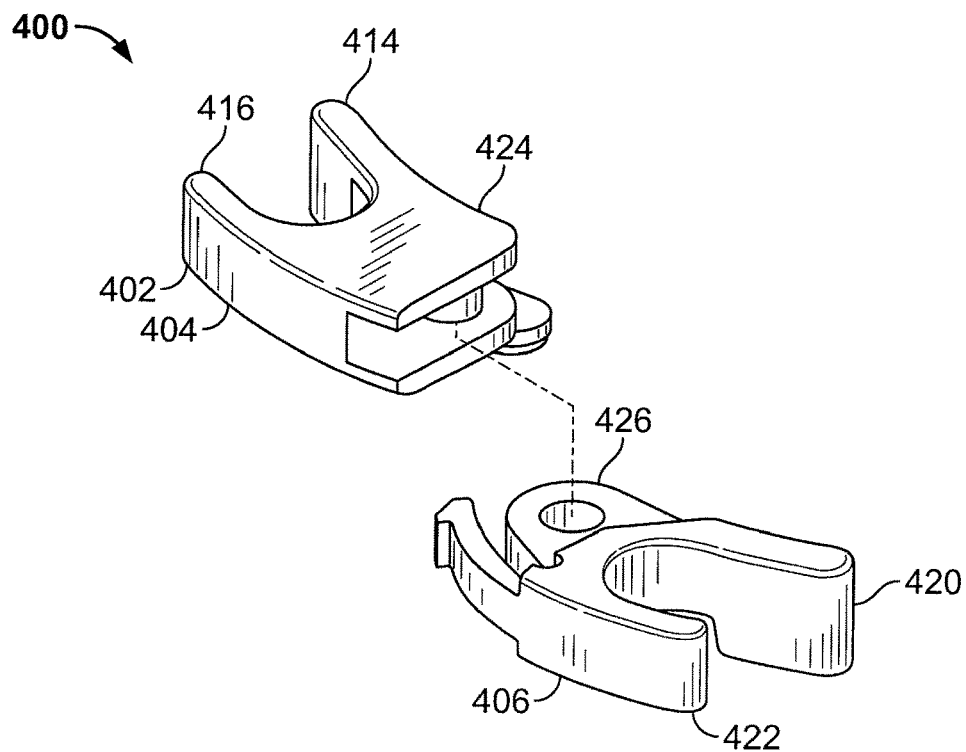
FIG. 21 is an exploded view of the implant device of FIG. 18.

In another form, as shown in FIG. 19, for example, the arms 414, 416, 420, 422 are generally curved. Accordingly, in the extended orientation, the implant body 402 has a generally arcuate shape, with the first arm 414 and the third arm 420 forming a generally concave surface 434 and the second arm 416 and the fourth arm 422 forming a generally convex surface 436. In one form, the concave surface 434 and convex surface 436 are configured to generally match the natural contour of the annulus 16 (as shown in FIG. 18, for example).

In another form, shown most clearly in FIGS. 22 and 23, the first and second lower portions 428, 430 have first and second bumper portions 438, 440 extending therefrom. More specifically, the first bumper portion 438 extends along an inside portion 442 of the first lower portion 428 and comprises a first rim portion 444 projecting therefrom. Likewise, the second bumper portion 440 extends along an inside portion 446 of the second lower portion 430 and comprises a second rim portion 448 projecting therefrom. When the implant body 402 is positioned in an opening in the annulus 16 to restrain an implant device, such as an artificial nucleus device (as illustrated in FIG. 18), the rim portions 444, 448 will advantageously engage only the lower portion of such device thereby reducing undesirable wear and debris by reducing the surface area of the implant device which the implant body 402 may engage.

With reference to FIGS. 25, 26, and 46-52, an implant device 500 is shown in accordance with another aspect of the invention. Again, implant device 500 includes an implant body 502 that is substantially similar to implant body 102. Accordingly, only the differences will be set forth in detail herein. As illustrated, implant body 502 is configured to be positioned in the intervertebral space 18 between adjacent vertebral bodies 20.

Implant body 502 includes a first member 504 comprising a first vertebral engaging portion 508 and a second member 506 comprising a second vertebral engaging portion 510. The first vertebral engaging portion 508 includes a first upper portion 528 and a first lower portion 530 for engaging the adjacent vertebral bodies 20 (as illustrated in FIG. 25). Likewise, the second vertebral engaging portion 510 includes a second upper portion 532 and a second lower portion 534 for engaging the adjacent vertebral bodies 20.

Figure 46:
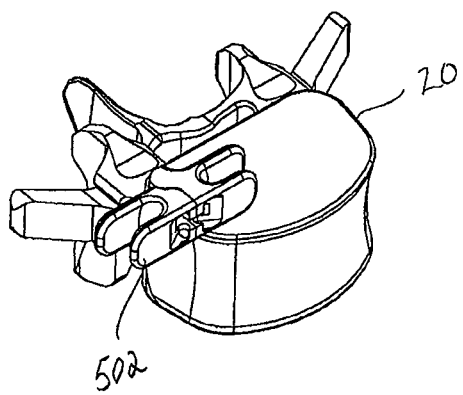
FIGS. 46-48 are perspective views of a portion of a human spine showing the implant device of FIG. 26 being into the intervertebral space in an extended orientation and then pivoted toward a compact orientation for implantation.
Figure 47:
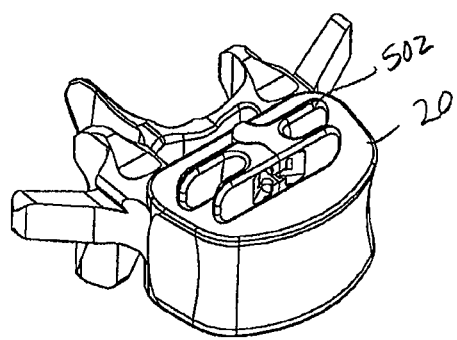
Figure 48:
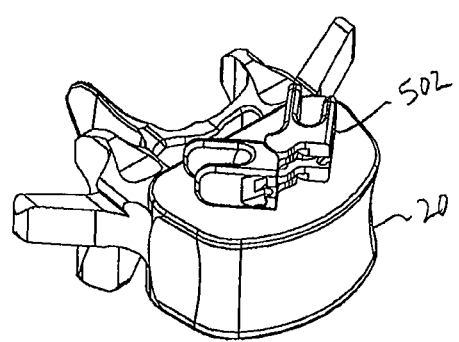
Figure 49:
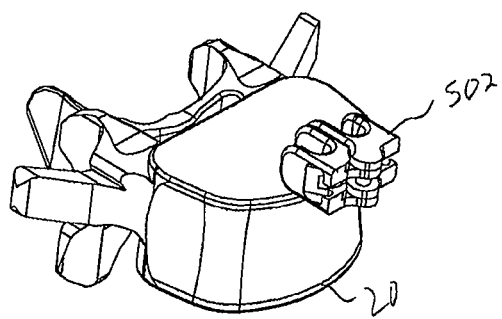
FIGS. 49-51 are perspective views of a portion of a human spine showing the implant device of FIG. 26 being into the intervertebral space in a compact orientation and then pivoted toward an extend orientation for implantation.
Figure 50:
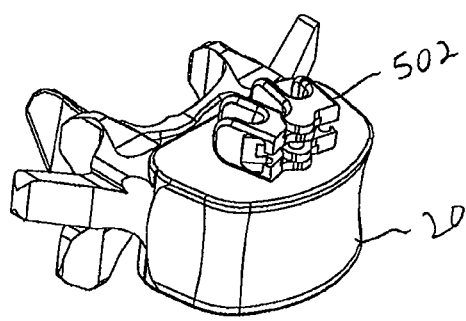
Figure 51:
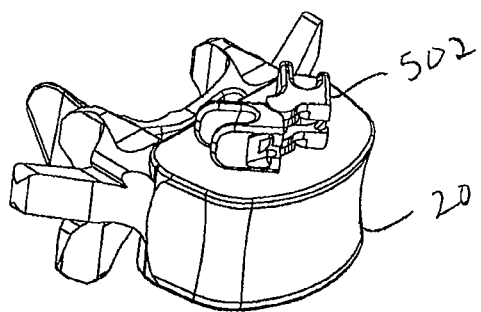

In one form, illustrated in FIGS. 46-48, the implant body 502 is configured to be inserted in the intervertebral space 18 in an extended orientation and, once in the intervertebral space 18, pivoted about an adjustable connection 526 toward a compact orientation. So configured, the implant body 502 can be advantageously inserted through a small opening in the annulus 16 (not shown) to the intervertebral space 18 and much of the annulus 16 can be retained. In another form, illustrated in FIGS. 49-51, the implant body 502 may be inserted in the intervertebral space 18 in a compact orientation and, once within the intervertebral space, pivoted about the adjustable connection 526 toward the extended orientation. Accordingly, the implant body 502 may advantageously be inserted through a small opening in the annulus 16 (not shown) to the intervertebral space 18.

Figure 26:
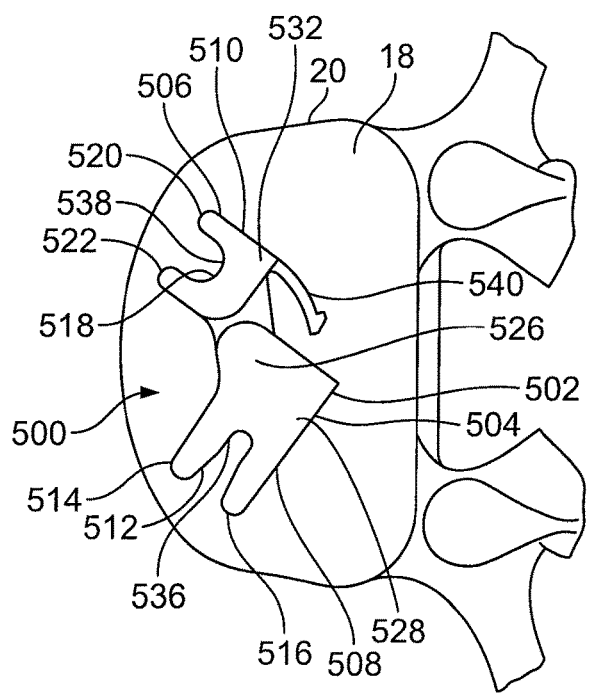
FIG. 26 is a top plan view of a portion of a human spine showing an implant device in accordance with another aspect of the invention positioned in an intervertebral space between adjacent vertebrae.

The implant body 502 may be arranged in any suitable orientation in the intervertebral space. For example, as illustrated in FIG. 26, the implant body 502 can be oriented with the adjustable connection 526 generally aligned with the anterior-posterior axis of the patient's spine and the arms 514, 516 and 520, 522 situated generally anterolaterally from the adjustable connection 526. In another form, the implant body 502 can be arranged in the intervertebral space 18 flipped approximately 180° from the orientation illustrated in FIG. 26, with the adjustable connection 526 generally aligned with the anterior-posterior axis of the patient's spine and the arms 514, 516 and 520, 522 situated generally posterolaterally from the adjustable connection 526.

In another form, the implant body 502 includes a securing mechanism 540 (similar to securing mechanism 140 described above, for example) for securing the implant body 502 in the extended configuration for insertion into the intervertebral space 18. In yet another form, the implant body 502 includes a ratchet mechanism (not shown) configured to allow the implant body 502 to be incrementally pivoted toward the compact orientation once inside the intervertebral space 18.

Preferably, a number of differently sized implant bodies 502 are provided so as to permit selection of an implant body 502 having a size that best suits the size of the intervertebral space 18. In yet another form, a number of differently sized first members 504 and second members 506 may be interchangeably coupled to provide a variety of differently sized and configured implant bodies 502.

Figure 52:
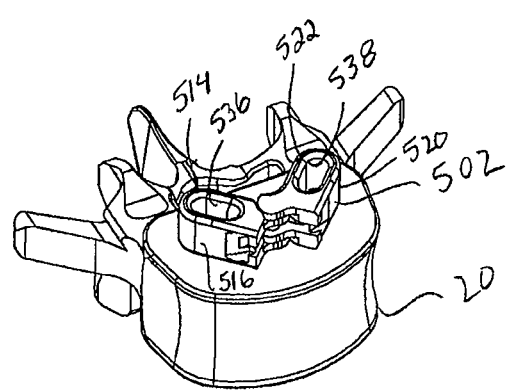
FIG. 52 is a perspective view of a portion of a human spine showing an alternative configuration of the implant device of FIG. 26.

As shown in FIG. 26, in one form, the first vertebral engaging portion 508 and the second vertebral engaging portion 510 are substantially solid. In another form, as shown in FIG. 52, the first vertebral engaging portion 508 and second vertebral engaging portion 510 include first and second openings 536, 538 configured to promote bone growth therethrough. As shown in FIG. 26, in one form, the first vertebral engaging portion 508 includes a first seat portion 512 extending between proximal ends of a first arm 514 and a second arm 516, with the first seat portion 512, the first arm 514, and the second arm 516 defining the first opening 536. Similarly, the second vertebral engaging portion 510 includes a second seat portion 518 extending between proximal ends of a third arm 520 and a fourth arm 522, with the second seat portion 518, the third arm 520, and the fourth arm 522 defining the second opening 538. In yet another form, shown in FIG. 52 for example, the first and second arms 514, 516 and/or the third and fourth arms 520, 522 may be curved toward one another to form an enclosed or substantially enclosed opening 536, 538.

As described above, the upper portions 528, 532 and the lower portions 530, 534 are configured to engage the adjacent vertebral bodies 20. Thus, in one form, the upper portions 528, 532 and the lower portions 530, 534 are configured to optimize engagement with the adjacent vertebral bodies 20 and stability of the implant body 502 within the intervertebral space 18 (through the use of a contour, texture, and/or coating, for example).

Figure 27A:
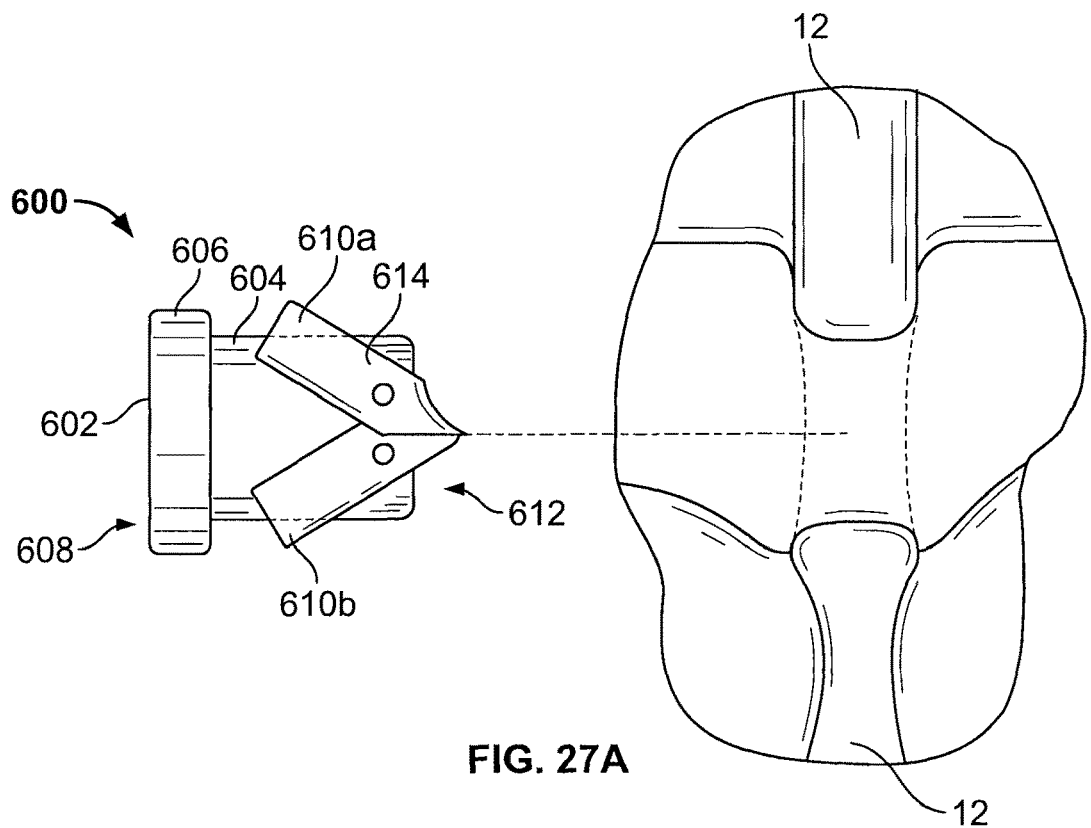
FIG. 27A is an elevation view of an implant device in accordance with another aspect of the invention.
Figure 27B:
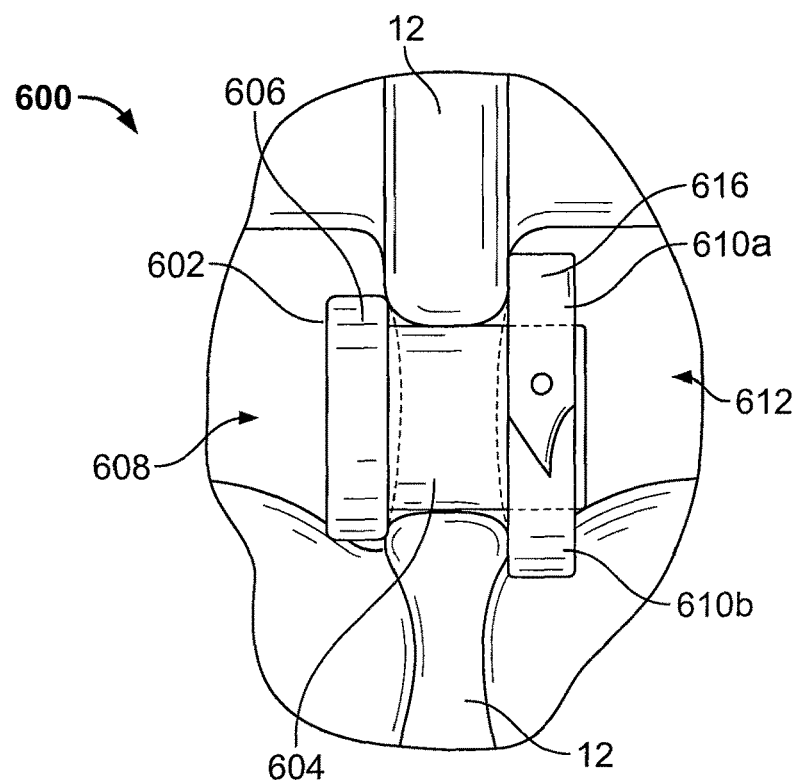
FIG. 27B is an elevation view of the implant device of FIG. 27A shown positioned between adjacent spinous processes.

With reference to FIGS. 27A-B, an implant device 600 is shown in accordance with yet another aspect of the invention. Implant device 600 includes an implant body 602 configured to be positioned between spinous processes 12 of adjacent vertebrae 10. Implant body 602 includes a spacer portion 604, a first flange 606 at a first end 608 of the spacer portion 604, and a pair of pivotable arms 610a,b at a second end 612 of the spacer portion 604. As illustrated, each of the pair of arms 610a,b is pivotably coupled to the spacer portion 604 such that the arms 610a,b may be arranged in a compact orientation (as shown in FIG. 27A) and pivoted to an extended orientation (as shown in FIG. 27B). In the compact orientation, the arms 610a,b define a distraction portion 614 configured to penetrate the tissue between the spinous processes 12 and to distract the tissue as the implant body 602 is inserted between the spinous processes 12. In the extended orientation, the arms 610a,b align to form a second flange 616. Thus, the implant body 602 is configured to be inserted between the spinous processes 12 with the arms 610a,b in the compact orientation. Once the spacer portion 604 is positioned between the spinous processes 12, the arms 610a,b are pivoted to the extended orientation.

In one form, the arms 610a,b are biased in the extended orientation (for example, by a spring mechanism or the like). So configured, as the implant body 602 is urged against the interspinous tissue, the arms 610a,b will be urged into the compact orientation for insertion of the implant body 602 between the spinous processes 12. The arms 610a,b are configured to snap back to the extended orientation after the arms 610a,b are clear of the interspinous tissue. In another form, the arms 610a,b are biased in the compact orientation. In such a case, once the arms 610a,b are clear of the interspinous tissue, the implant body 602 is retracted from the interspinous tissue in the direction opposite the direction of insertion. As the implant body 602 is retracted, the arms 610a,b will be urged against the interspinous tissue causing them to pivot into the extended orientation. Once positioned between the spinous processes 12, the first flange 606 limits further movement of the implant body 602 in the direction of insertion, while the second flange 616 limits movement of the implant body 602 in the direction opposite the direction of insertion.

Figure 28A:
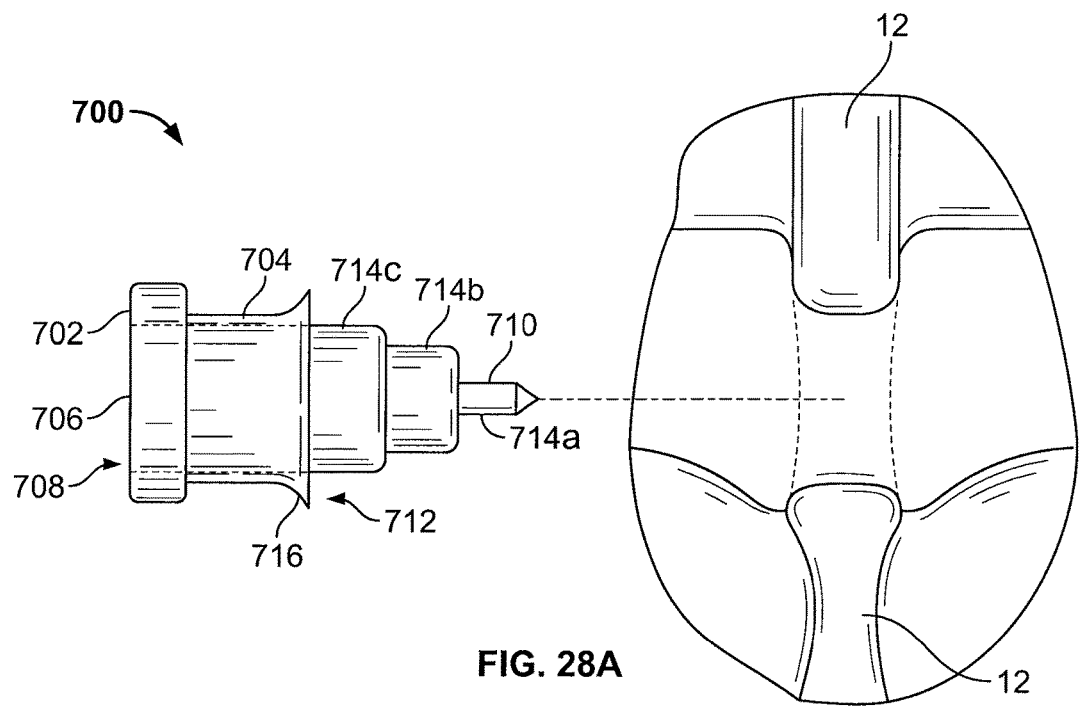
FIG. 28A is an elevation view of an implant device in accordance with another aspect of the invention.
Figure 28B:
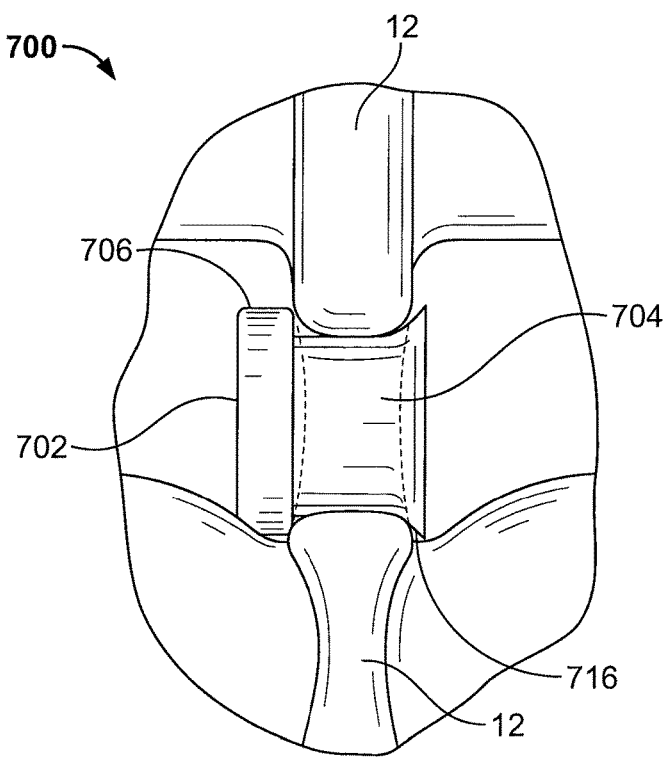
FIG. 28B is an elevation view of the implant device of FIG. 28A shown positioned between adjacent spinous processes.

With reference to FIGS. 28A-B, an implant device 700 is shown in accordance with yet another aspect of the invention. Implant device 700 includes an implant body 702 configured to be positioned between spinous processes 12 of adjacent vertebrae 10. Implant body 702 includes a spacer portion 704 having a first flange 706 at a first end 708 and a distraction portion 710 at a second end 712. The first flange 706 includes a tool engagement portion (not shown) for adjusting the implant body 702 to the compact orientation. As illustrated, the distraction portion 710 includes a series of collapsible cylinder portions 714a-c. The cylinder portions 714a-c are spaced apart from each other in a distraction orientation (as shown in FIG. 28A) and collapsed one within the next and received within in the spacer portion 704 in a collapsed orientation (as shown in FIG. 28B). In the distraction orientation, the cylinder portions 714a-c are configured to penetrate the tissue between the spinous processes 12 and to distract the tissue as the implant body 702 is inserted between the spinous processes 12.

Thus, the implant body 702 is configured to be inserted between the spinous processes 12 with the cylinder portions 714a-c in the distraction orientation. In one form, once the spacer portion 704 is positioned between the spinous processes 12, the cylinder portions 714a-c are collapsed into the implant body 702 to the collapsed orientation. In another form, each cylinder portion 714a-c is biased away from the next cylinder portion 714 (for example, with a series of springs). The first cylinder portion 714a is inserted in the interspinous tissue, and then the remaining cylinder portions 714b-c and the spacer portion 704 are urged one over the other to progressively dilate the interspinous tissue and position the spacer portion 704 between the spinous processes 12.

Once positioned between the spinous processes 12, the first flange 706 limits further movement of the implant body 702 in the direction of insertion. As illustrated, in one form the second end 712 of the spacer portion 704 includes a rim portion 716 that is smaller in diameter than the first flange 706. Such a configuration advantageously permits a series of implant bodies 702 to be positioned between three or more spinous processes 12, with adjacent implant bodies 702 arranged in a mirror image orientation, thereby preventing undesirable contact between the adjacent implant bodies 702.

Figure 29A:
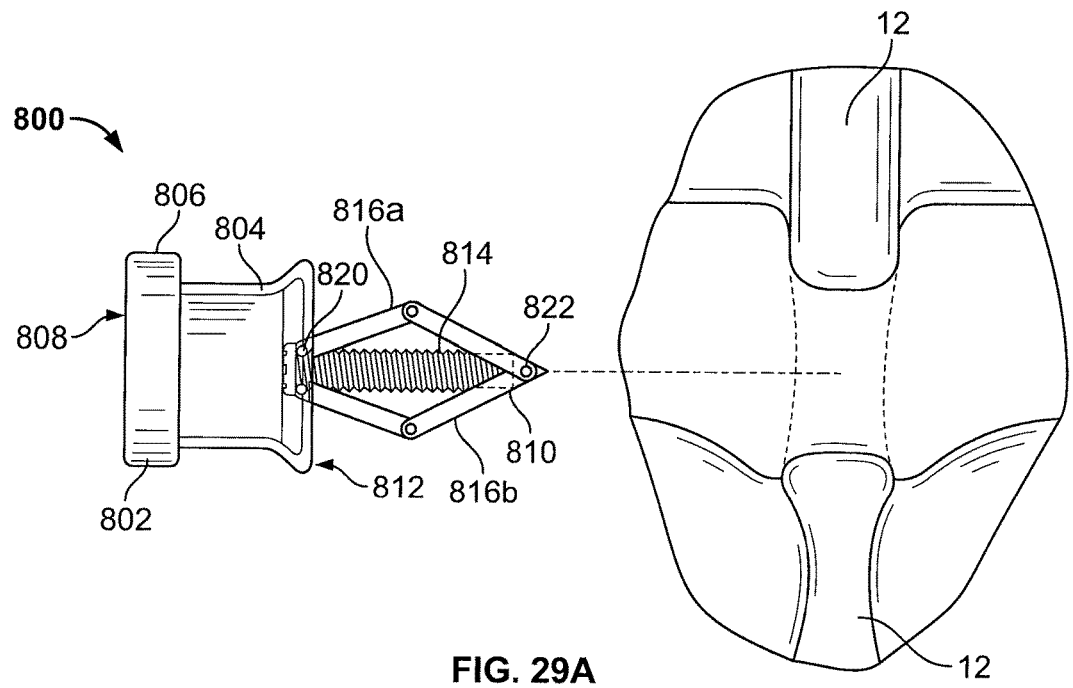
FIG. 29A is an elevation view of an implant device in accordance with another aspect of the invention.
Figure 29B:
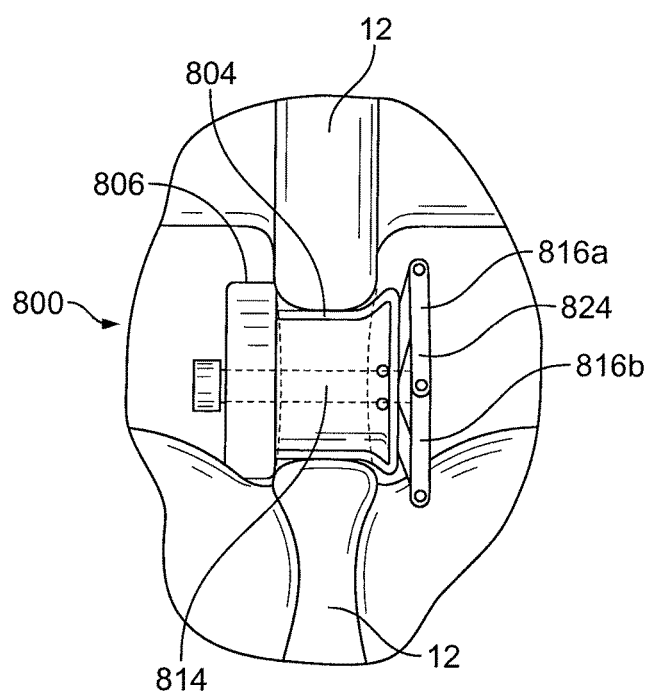
FIG. 29B is an elevation view of the implant device of FIG. 29A shown positioned between adjacent spinous processes.

Referring to FIG. 29A-B, an implant device 800 is shown in accordance with another aspect of the invention. Implant device 800 includes an implant body 802 configured to be positioned between spinous processes 12 of adjacent vertebrae 10. Implant body 802 includes a spacer portion 804, a first flange 806 at a first end 808 of the spacer portion 804 and a distraction portion 810 at a second end 812. The distraction portion 810 includes a threaded shaft 814 and a pair of hinged arms 816a,b pivotably coupled to the threaded shaft 814 at a first end 820 and a second end 822 of the threaded shaft 814. As illustrated, the threaded shaft 814 may extend from the second end 808 of the spacer portion 804 or may be threadably received within the spacer portion 804. As shown in FIG. 29A, when the threaded shaft 814, extends from the spacer portion 804, the hinged arms 816a,b are arranged in a compact orientation configured to penetrate the interspinous tissue and distract the tissue as the implant body 802 is inserted between the spinous processes 12. The first flange 806 includes a tool engagement portion (not shown) to reposition the implant device 800 from a distraction orientation to a compact orientation. As shown in FIG. 29B, as the threaded shaft 814 is received within the spacer portion 804, the hinged arms 816a,b collapse into an extended orientation in which the arms 816a,b form a second flange 824.

Thus, the implant body 802 is configured to be inserted between the spinous processes 12 with the arms 816a,b in the compact orientation. Once the spacer portion 804 is positioned between the spinous processes 12, the threaded shaft 814 is threadably received within the spacer portion 804 and the arms 816a,b are collapsed into the extended orientation to form the second flange 824. Once positioned between the spinous processes, the first flange 806 limits further movement of the implant body 802 in the direction of insertion, while the second flange 824 limits movement of the implant body 802 in the direction opposite the direction of insertion.

Figure 30:
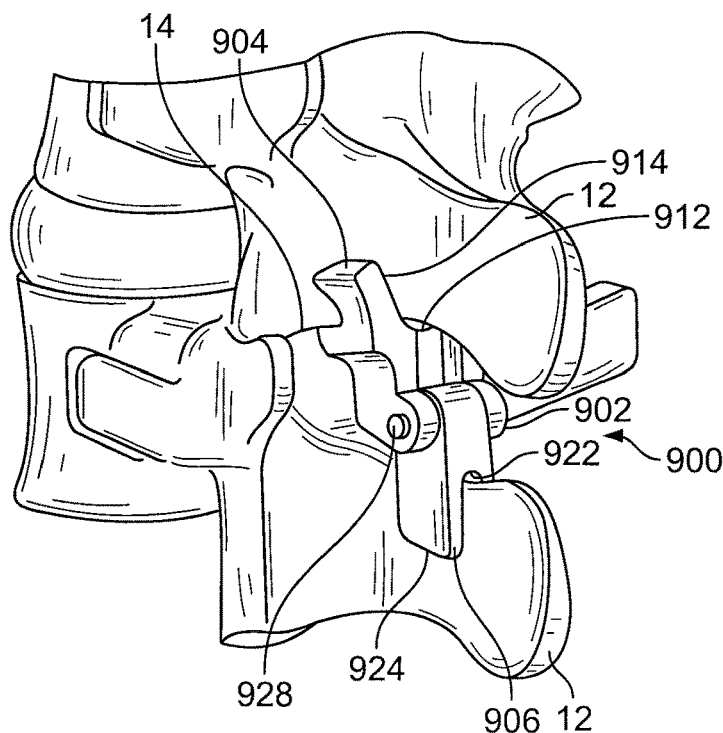
FIG. 30 is a perspective view of a portion of a human spine showing an implant device in accordance with another aspect of the invention positioned between laminar regions and the spinous process of adjacent vertebrae.
Figure 31:
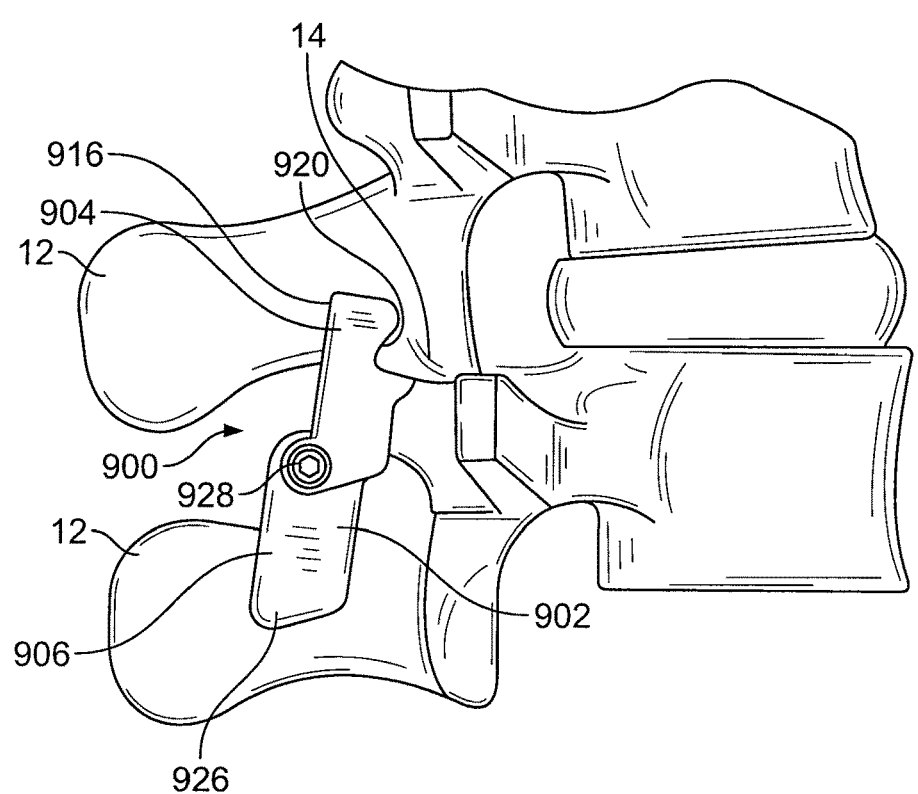
FIG. 31 is an elevation view of a portion of a human spine showing the implant device of FIG. 30.
Figure 32:
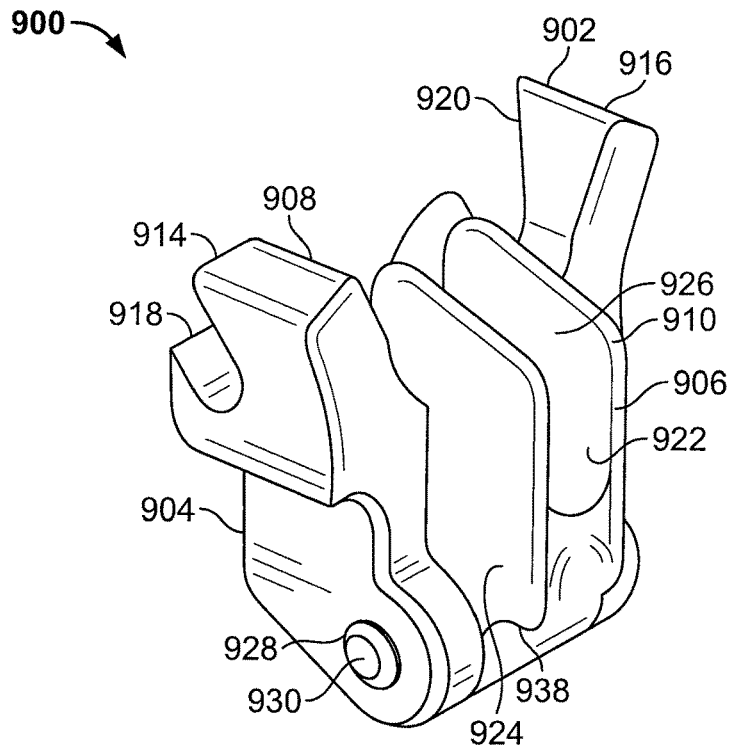
FIG. 32 is a perspective view of the implant device of FIG. 30 shown in a compact orientation.
Figure 33:
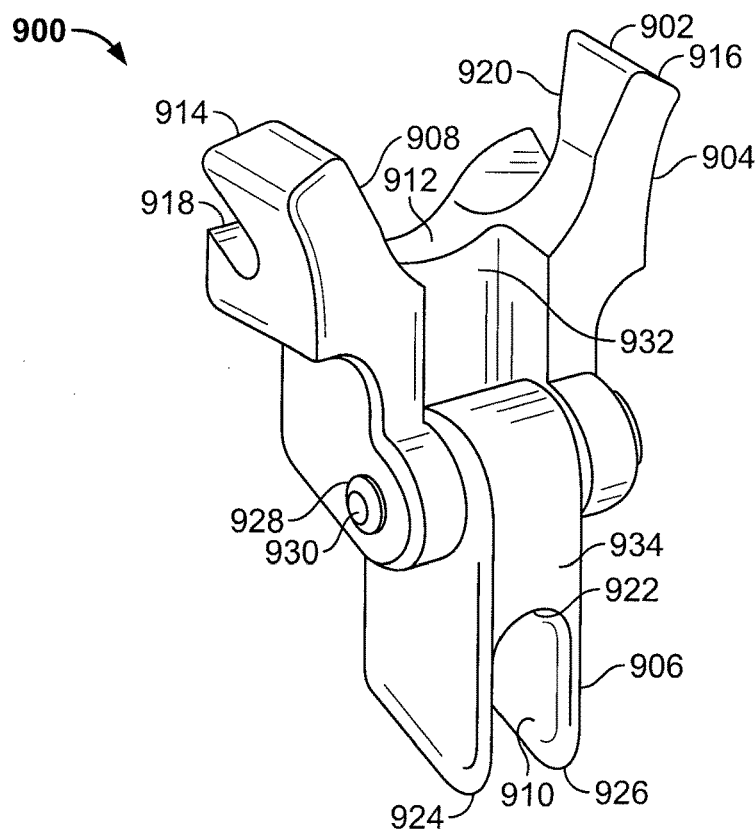
FIG. 33 is a perspective view of the implant device of FIG. 30 shown in an extended orientation.
Figure 34:
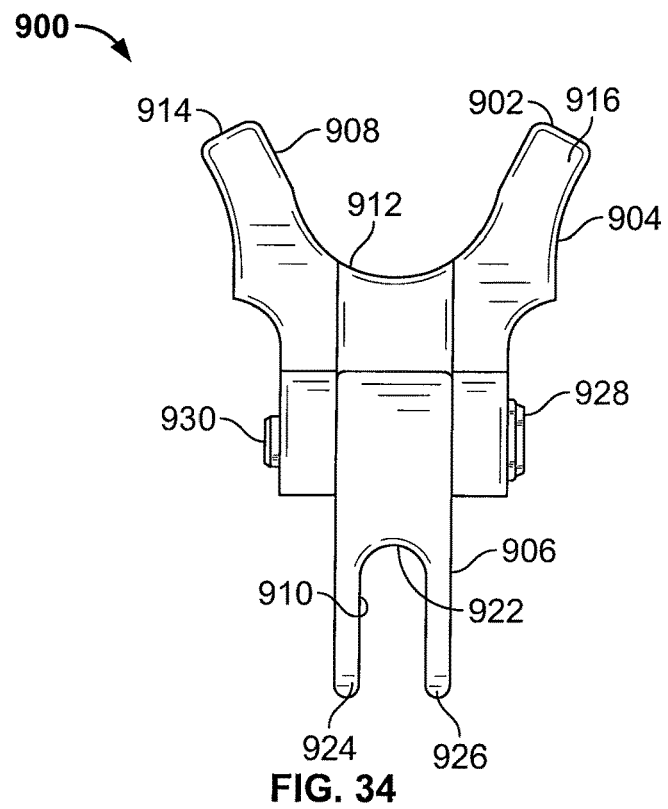
FIG. 34 is a top plan view of the implant device of FIG. 30.
Figure 35:
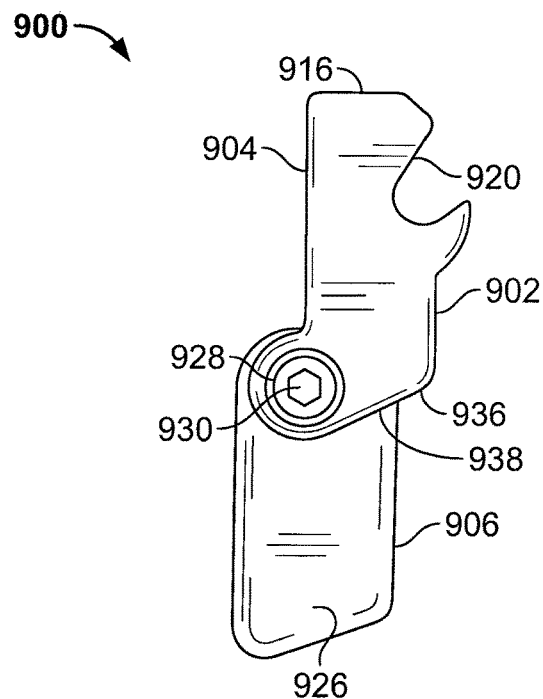
FIG. 35 is an elevation view of the implant device of FIG. 30.

With reference to FIGS. 30-35, an implant device 900 is shown in accordance with yet another aspect of the invention. Implant device 900 includes an implant body 902 configured for being positioned between the laminar regions 14 and the spinous process 12 of adjacent vertebrae 10. The implant body 902 includes a first member 904 and a second member 906 adjustably interconnected such that the implant body 902 can be arranged in a compact orientation (as shown in FIG. 32), and an extended orientation (as shown in FIGS. 33-35).

The first member 904 includes a first vertebral engaging portion 908 and the second member 906 includes a second vertebral engaging portion 910. As shown in FIGS. 33 and 34, the first vertebral engaging portion 908 includes a first seat portion 912 extending between proximal ends of a first arm 914 and a second arm 916. Distal ends of first and second arms 914, 916 include first and second hook portions 918, 920. As illustrated in FIG. 30, the first seat portion 912 is configured to provide a clearance for the superior spinous process 12 to pass therethrough with the first arm 914 and the second arm 916 on opposite sides of the spinous process 12. As can be seen, the superior spinous process 12 need not contact the first seat portion 912. Rather, the first and second hook portions 918, 920 are configured to hook around the laminar regions 14 on either side of the spinous process 12.

The second vertebral engaging portion 910 includes a second seat portion 922 extending between proximal ends of a third arm 924 and a fourth arm 926. The second seat portion 922 is configured to receive a portion of the inferior spinous process 12 with the third arm 924 and the fourth arm 926 on opposite sides of the spinous process 12.

As shown, for example, in FIGS. 32-35, in one form, the first member 904 and the second member 906 are pivotably coupled at adjustable connection 928 such that the first and second members 904, 906 can freely pivot between the compact orientation (FIG. 32) and the extended orientation (FIG. 33). In one form, adjustable connection 928 includes a pin 930 splined to the second member 906. So configured, the pin 930 can be rotated (for example, with an instrument) to pivot the second member 906 between the compact orientation and the extended orientation.

Referring to FIGS. 32-35, the compact orientation and the extended orientation are defined by the interfering engagement between the first member 904 and the second member 906. More specifically, in the compact orientation, a first stop surface 932 extending from the first seat portion 912 away from arms 914, 916 abuttingly engages a second stop surface 934 extending from second seat portion 922 away from arms 924, 926. In the extended orientation, a third stop surface 936 of the first member 904 abuttingly engages a fourth stop surface 938 of the second member 906.

As shown in FIGS. 30 and 31, the implant body 902 is preferably configured to engage the superior laminar regions 14 and the inferior spinous process 12 when the implant body 902 is in the extended orientation to space apart the adjacent vertebrae 10 to the desired spatial relationship. In one form, the implant body 902 is sized to distract the adjacent vertebrae 10. In another form, the second member 906 is configured to cam against the inferior spinous process 12 to distract the adjacent vertebrae 10 as the implant body 902 is pivoted to the extended orientation. This distraction advantageously promotes stability of the implant body 902 in the extended orientation between the inferior spinous process 12 and the superior laminar regions 14.

In another form, a number of differently sized implant bodies 902 are provided. In yet another form, a number of differently sized first members 904 and second members 906 may be interchangeably coupled to provide a variety of differently sized and configured implant bodies 902.

With reference to FIGS. 36-40, an implant device 1000 is shown in accordance with yet another aspect of the invention. Implant device 1000 includes an implant body 1002 configured for being positioned between laminar regions 14 of adjacent vertebrae 10. The implant body 1002 includes a first member 1004 and a second member 1006 adjustably interconnected such that the implant body 1002 can be arranged in a compact orientation (as shown in FIG. 37A, for example), and extended orientation (as shown in FIG. 37B, for example).

Figure 37B:
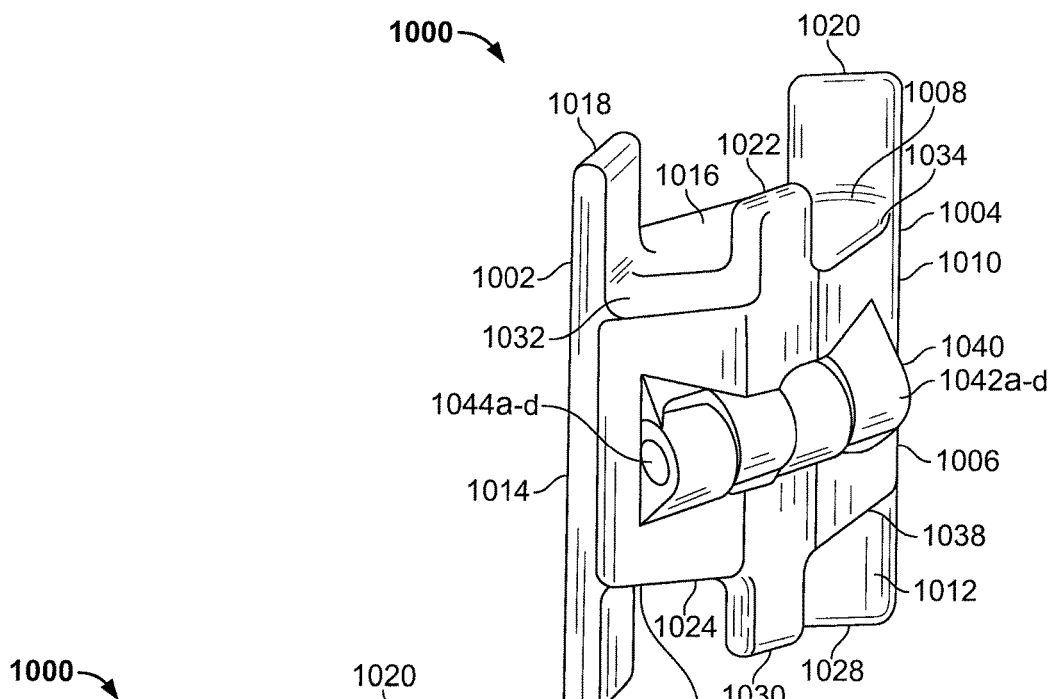
FIG. 37B is a perspective view of the implant device of FIG. 36 shown in an extended orientation.
Figure 38:
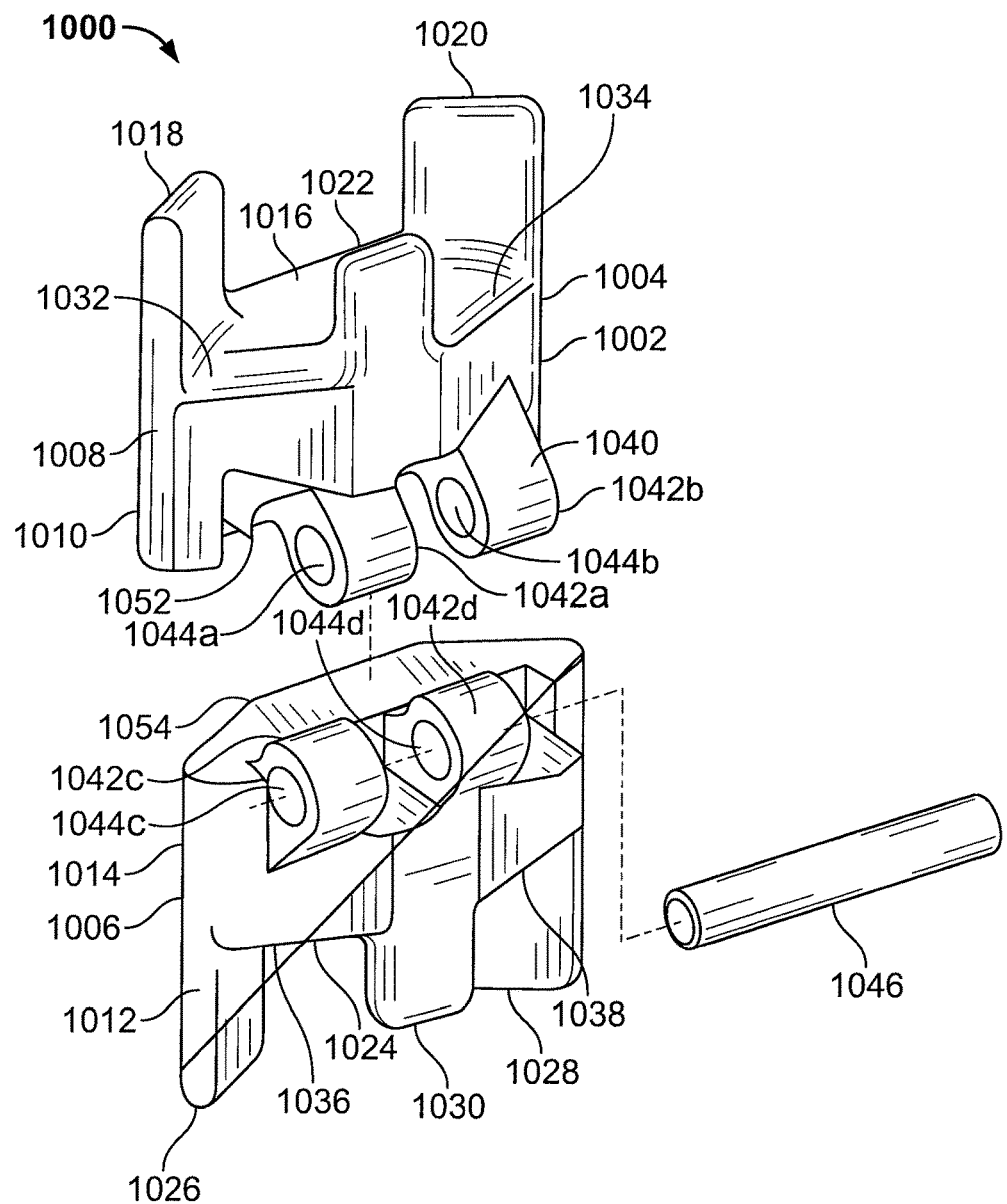
FIG. 38 is an exploded view of the implant device of FIG. 36.

The first member 1004 includes a first vertebral engaging portion 1008 and a first spacer portion 1010 extending from the first vertebral engaging portion 1008. The second member 1006 includes a second vertebral engaging portion 1012 and a second spacer portion 1014 extending from the second vertebral engaging portion 1012. As shown in FIGS. 37B and 38, the first and second vertebral engaging portions 1008, 1012 include first and second seat portions 1016, 1024 configured to provide a clearance for the spinous process 12 to pass therethrough.

The first seat portion 1016 includes first, second, and third arms 1018, 1020, 1022 extending therefrom away from the spacer portion 1010 configured to engage separate laminar regions 14 proximate one of the adjacent spinous processes 12. Likewise, the second seat portion 1024 includes fourth, fifth and sixth arms 1026, 1028, 1030 extending therefrom away from the spacer portion 1014 configured to engage separate laminar regions 14 proximate the other spinous process 12.

Figure 37A:
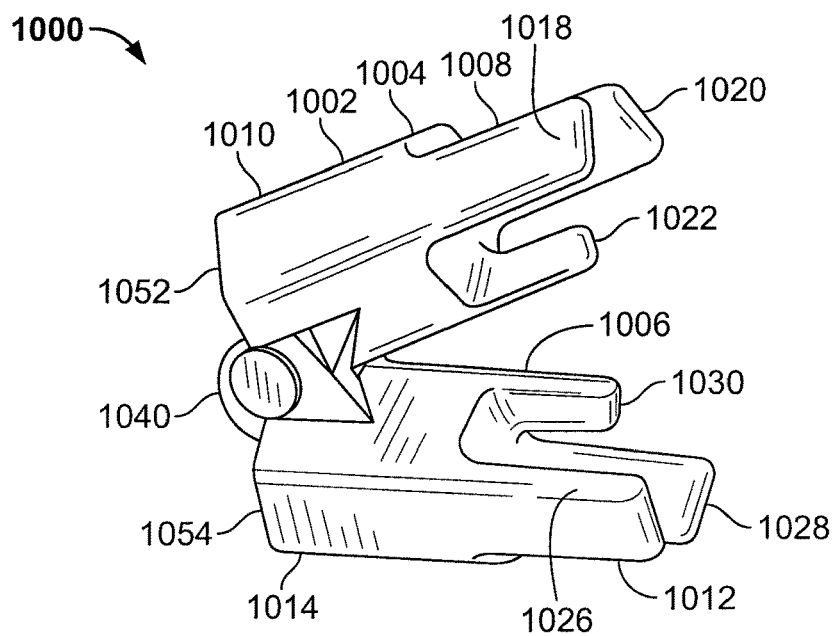
FIG. 37A is perspective view of the implant device of FIG. 36 shown in a compact orientation.

As illustrated in FIG. 37A, in one form, the first and second arms 1018, 1020 are longer than the third arm 1022. Similarly, the fourth and fifth arms 1026, 1028 are longer than the sixth arm 1030. In another form, as shown in FIG. 37B, the first seat portion 1016 includes first and second chamfers 1032, 1034, with the first chamfer 1032 extending between the first arm 1018 and the third arm 1022 and the second chamfer 1034 extending between the second arm 1020 and the third arm 1022. Similarly, the second seat portion 1024 includes third and fourth chamfers 1036, 1038 with the third chamfer 1036 extending between the fourth arm 1026 and the sixth arm 1030 and the fourth chamfer 1038 extending between the fifth arm 1028 and the sixth arm 1030.

As shown, for example, in FIGS. 37A-B and 38, in one form, the first member 1004 and the second member 1006 are pivotably coupled at an adjustable connection 1040 such that the first and second members 1004, 1006 can freely pivot between the compact orientation (FIG. 37A) and the extended orientation (FIG. 37B). In one form, the adjustable connection 1040 is similar to a door hinge, with the first member 1004 including first and second bosses 1042a-b and the second member 1006 including third and fourth bosses 1042c-d, with each of the bosses 1042a-d including an opening 1044a-d therethrough for receiving a pin 1046.

Figure 39:
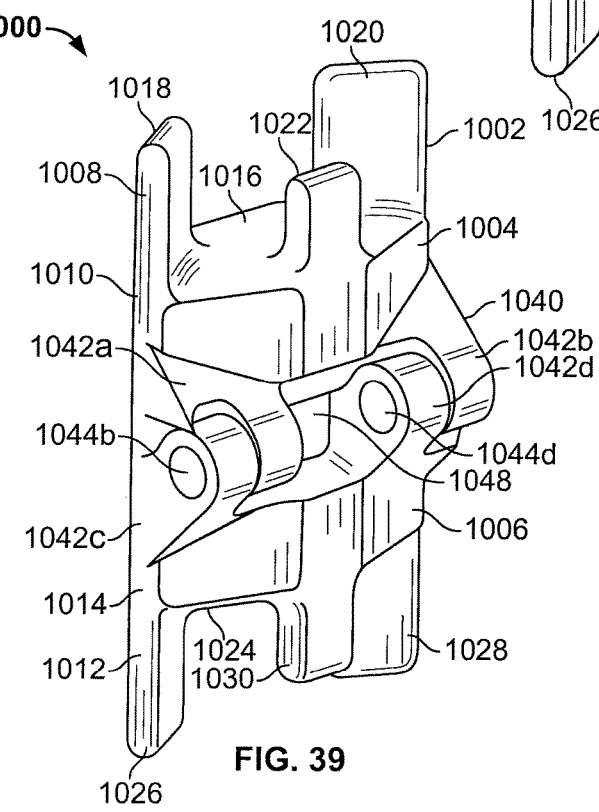
FIG. 39 is a perspective view of an implant device in accordance with another aspect of the invention.
Figure 40:
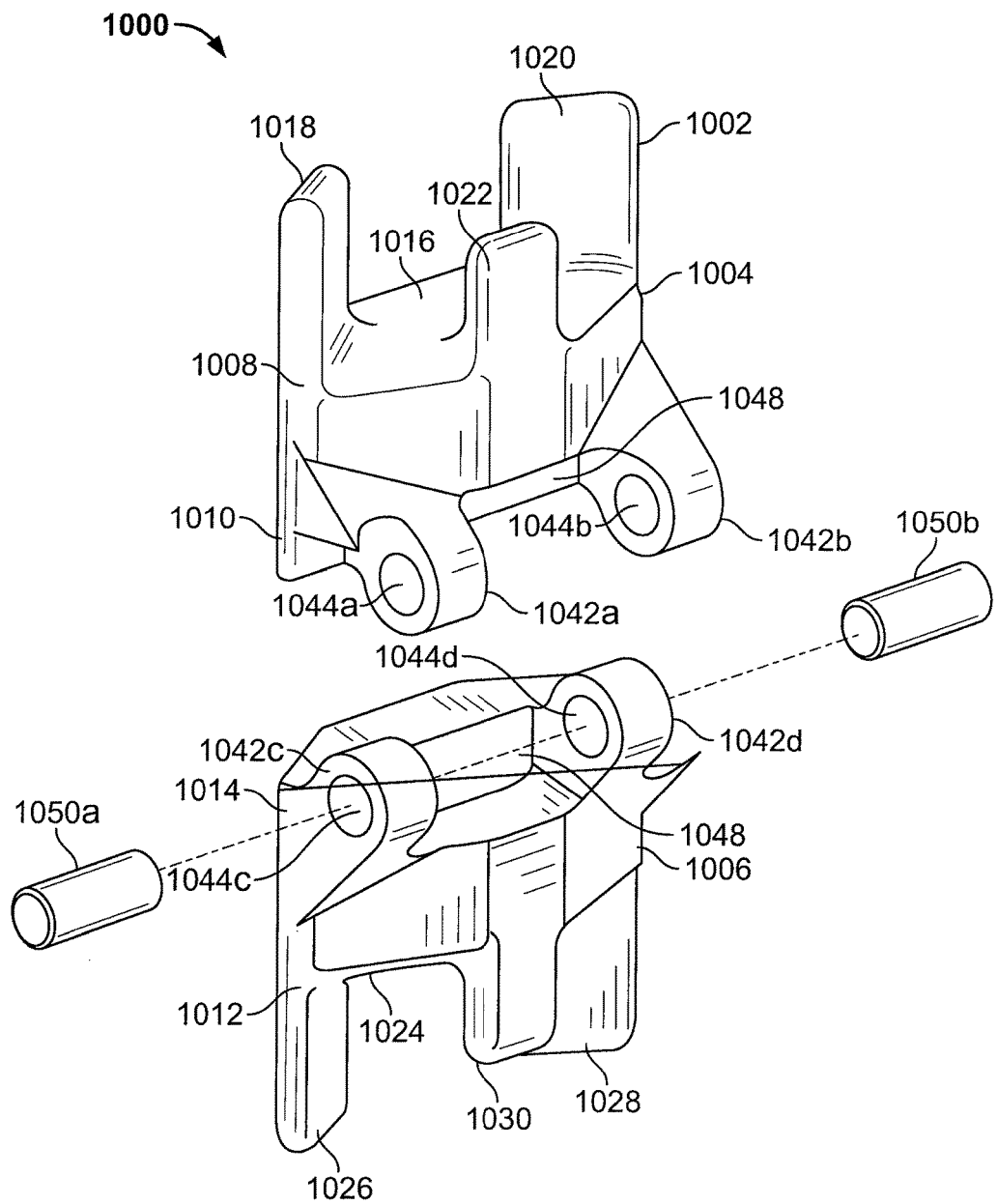
FIG. 40 is an exploded view of the implant device of FIG. 39.

In another form, shown in FIGS. 39 and 40, the bosses 1042a and c are spaced apart from the bosses 1042b and d by a space 1048. A first pin 1050a is received in the openings 1044a and c and a second pin 1050b is received in the openings 1044b and d. In this form, the space 1048 can be aligned with the spinal canal with the implant body 1002 positioned between adjacent spinous processes 12 to advantageously minimize any undesirable impingement of the spinal canal.

Figure 36:
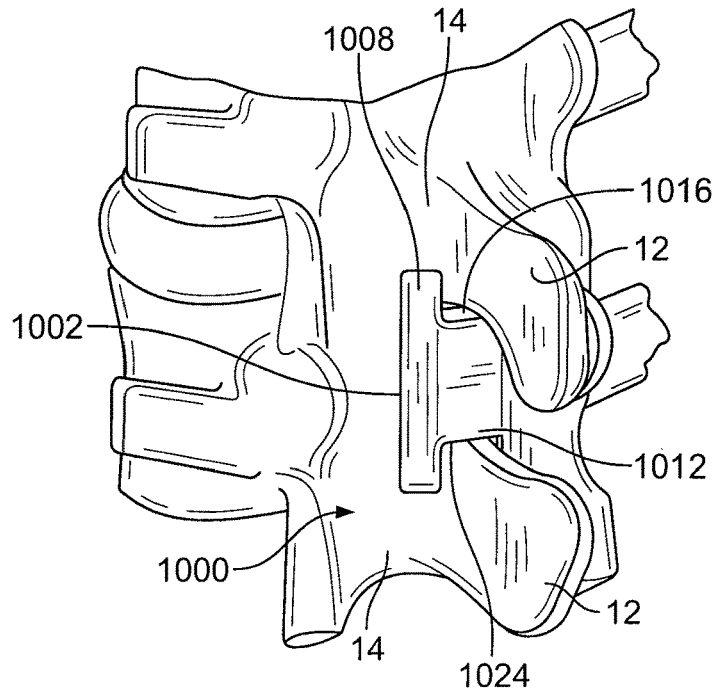
FIG. 36 is a perspective view of a portion of a human spine showing an implant device in accordance with another aspect of the invention positioned between laminar regions of adjacent vertebrae.

Referring to FIG. 38, in the extended orientation of the implant body 1002, a first surface 1052 of the first member 1004 extending generally parallel to the first seat portion 1016 abuttingly engages a second surface 1054 of the second member 1006 extending generally parallel to the second seat portion 1024. As illustrated in FIGS. 36 and 38, for example, when the implant body 1002 is in the extended orientation, the first and second spacer portions 1010, 1014 align to space apart the first vertebral engaging portion 1008 and the second vertebral engaging portion 1012.

With reference to FIGS. 37A-B and 38, the implant body 1002 is configured to be inserted between the laminar regions 14 of adjacent vertebrae 10 in the compact orientation and then pivoted to the extended orientation to engage the laminar regions 14. As shown in FIG. 36, when the implant body 1002 is positioned between the laminar regions 14 in the extended orientation, the first seat portion 1016 provides a clearance for one of the adjacent spinous processes 12, the second seat portion 1024 provides a clearance for the other spinous process 12, and the first and second spacer portions 1010, 1014 extend therebetween. Thus, the implant body 1002 is preferably configured to space the adjacent vertebrae 10 apart to the desired spatial relationship. In one form, the implant body 1002 is sized to distract the adjacent vertebrae 10. In another form, at least one of the first and second seat portions 1016, 1024 is configured to cam against one of the spinous processes 12 to distract the adjacent vertebrae 10 as the implant body 1002 is pivoted to the extended orientation. This distraction advantageously promotes stability of the implant body 1002 in the extended orientation between the laminar regions 14.

In another form, a number of differently sized implant bodies 1002 are provided. In yet another form, a number of differently sized first members 1004 and second members 1006 may be interchangeably coupled to provide a variety of differently sized and configured implant bodies 1002.

Figure 41:
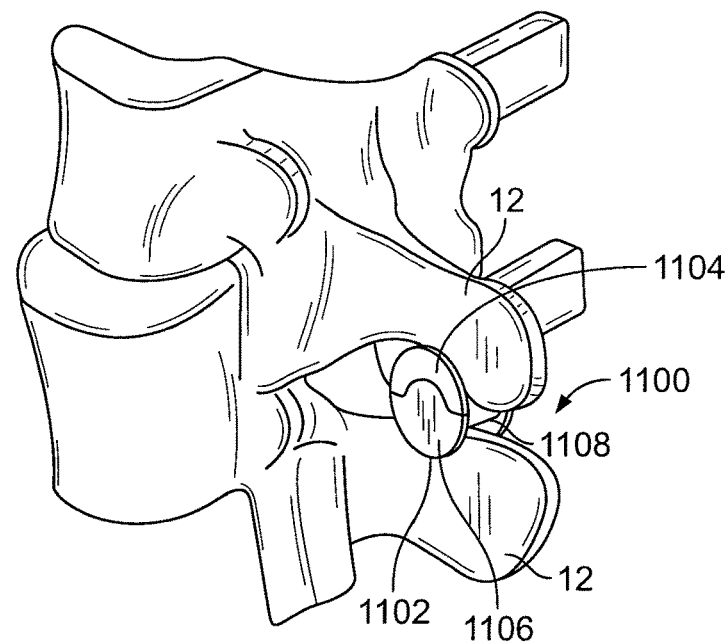
FIG. 41 is a perspective view of a portion of a human spine showing an implant device in accordance with another aspect of the invention positioned between spinous processes of adjacent vertebrae.
Figure 42:
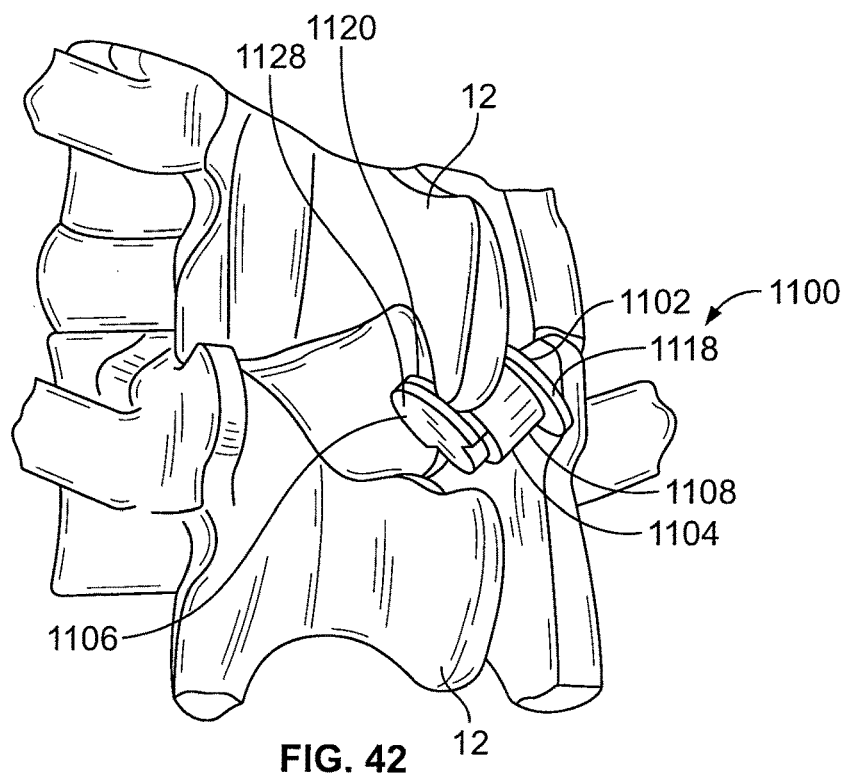
FIG. 42 is a perspective view of a portion of a human spine showing insertion of the implant device of FIG. 41 in a compact orientation between spinous processes of adjacent vertebrae.
Figure 43:
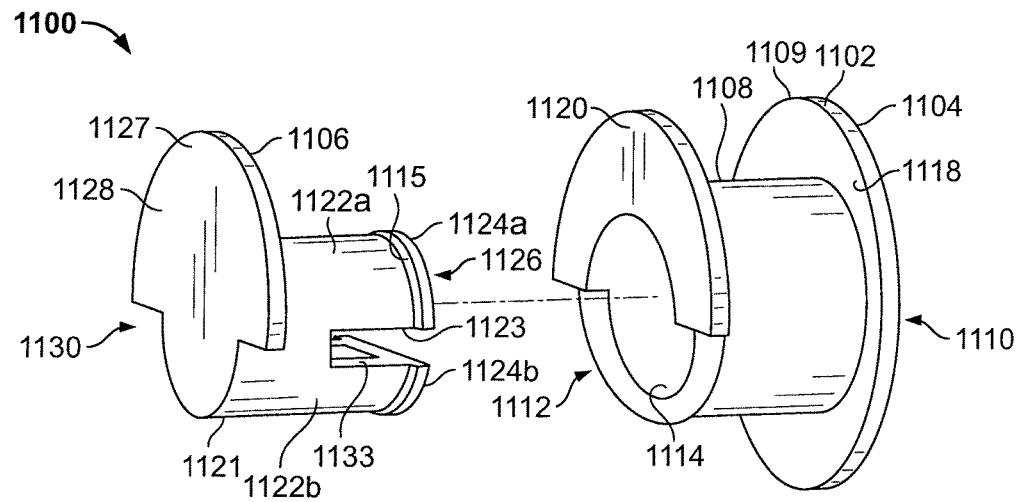
FIG. 43 is an exploded view of the implant device of FIG. 41 shown in a compact orientation.
Figure 44:
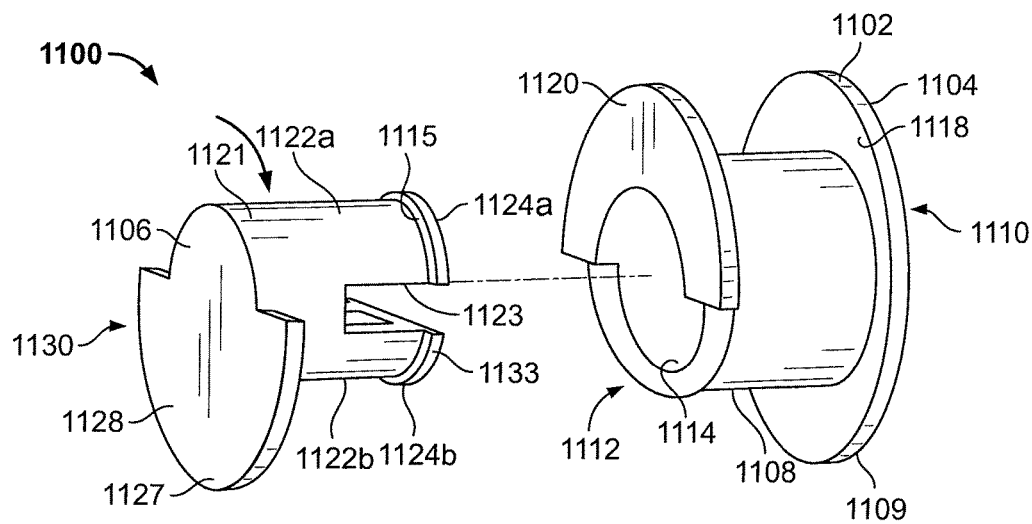
FIG. 44 is an exploded view of the implant device of FIG. 41 shown in an extended orientation.
Figure 45:
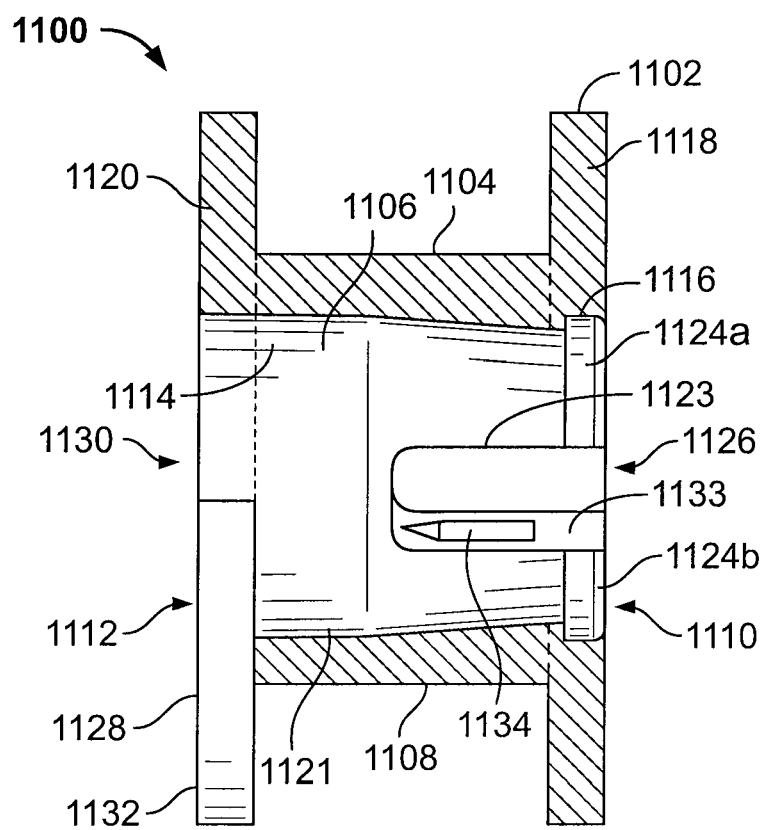
FIG. 45 is cross-section view of the implant device of FIG. 41 shown in an extended orientation.

Referring to FIGS. 41-45, an implant device 1100 is shown in accordance with yet another aspect of the invention. Implant device 1100 includes an implant body 1102 configured for being positioned between spinous processes 12 of adjacent vertebrae 10. The implant body 1102 includes a first member 1104 and a second member 1106 adjustably interconnected such that the implant body 1102 can be arranged in a compact orientation (as shown in FIGS. 42 and 43, for example) for being inserted between the spinous processes 12, and an extended orientation (as shown in FIGS. 41, 43, and 45, for example), for resisting expulsion of the implant body 1102 therefrom.

As shown in FIGS. 43-45, in one form, the first member 1104 includes a generally cylindrical spacer portion 1108 with a first end 1110 and a second end 1112 and a longitudinal throughbore 1114 extending between the ends 1110, 1112. The spacer portion 1108 includes a first retention member 1109 configured to resist expulsion of the implant body 1102 from between the spinous processes 12. In the illustrated form, an annular flange 1118 is provided at the first end 1110 of the spacer portion 1108 and a first semi-annular flange 1120 is provided at the second end 1112.

As shown, the second member 1106 preferably includes another generally cylindrical portion 1121 having a first end 1126 and a second end 1130. The cylindrical portion 1121 is configured to be slideably received in the longitudinal throughbore 1114 of the first member 1104. A second retention member 1127, such as a second semiannular flange 1128, is provided at the second end 1130 of the cylindrical portion 1121.

As illustrated in FIGS. 43 and 44, in one form, the cylindrical portion 1121 is rotatable within the longitudinal bore 1114 to move the implant body 1102 between the compact orientation and the extended orientation. More specifically, the implant body 1102 can be arranged in the compact orientation (as shown in FIGS. 42 and 43, for example), in which the cylindrical portion 1121 is partially received in the longitudinal throughbore 1114 of the spacer portion 1108 and the second semiannular flange 1128 is arranged in an overlapping orientation with the first semiannular flange 1120. The cylindrical portion 1121 can be rotated approximately 180° (as illustrated in FIG. 44) and retracted further into the first member 1104 to be arranged in the extended orientation (shown in FIGS. 41 and 45), in which the first and second semiannular flanges 1120, 1128 form a substantially flush, complete annular flange 1132 at the second end 1112 of the spacer portion 1108.

According to another form, the implant body 1102 includes a securing mechanism 1115 configured to secure the implant body 1102 in the extended orientation. As illustrated in FIGS. 43-45, in one form, the cylindrical portion 1121 includes a slot 1123 at the first end 1126 defining a pair of deflectable arms 1122a,b. Each of the arms 1122a,b preferably has a ridge 1124a,b at the first end 1126 configured to mate with an interior groove 1116 at the first end 1110 of the spacer portion 1108 with the arms 1122a,b received in the longitudinal throughbore 1114. In the compact orientation, with the second semiannular flange 1128 arranged in an overlapping orientation with the first semiannular flange 1120 and the cylindrical portion 1121 only partially received in the longitudinal throughbore 1114, the ridges 1124a,b are disengaged from the interior groove 1116. In the extended orientation (as shown in FIGS. 41 and 44, for example), the cylindrical portion 1121 is rotated approximately 180° and retracted further into the longitudinal throughbore 1114 such that the ridges 1124a,b snap into the interior groove 1116 to secure the implant body 1102 in the orientation (as shown in FIG. 45).

The implant body 1102 is configured to be inserted between adjacent spinous processes 12 in the compact orientation and then adjusted to the extended orientation. Thus, the implant body 1102 can be inserted through a minimally invasive procedure requiring only a single incision on one side of the spine. The implant body 1102 is preferably inserted through an aperture formed in the interspinous ligament. In one form, the aperture is sized and/or shaped to correspond to the size and/or generally cylindrical shape of the implant body 1102. For example, in one form, a specialized cutting instrument (not shown) may be used to cut an aperture in the interspinous ligament of a predetermined size and/or shape, such as an oval or a circle.

In another form, the first semiannular flange 1120 and, optionally, the second semiannular flange 1128, is configured to assist insertion of the implant body 1102 through such an aperture. For example, the semiannular flange 1120 may have greater height relative to the annular flange 1118. Additionally, a portion of the annular flange 1120 may be canted outward and/or beveled for aiding insertion.

In another form, a number of differently sized implant bodies 1102 are provided. The spacer portion 1108 is preferably sized and positioned to space the adjacent spinous processes 12 apart to the desired spatial relationship. The annular flanges 1118, 1132 are preferably sized to limit movement of the implant body 1102 in either the direction of insertion or the opposite direction with the spacer portion 1108 positioned between the spinous processes 12. In yet another form, the distance between the annular flanges 1118, 1132 may be varied. In one form, for example, the spacer portion 1108 may include one or more additional interior grooves 1116 configured to mate with the ridges 1124a,b of the arms 1122a,b. Accordingly, the annular flanges 1118, 1132 can be secured at a number of different positions by snapping the ridges 1124a,b of the arms 1122a,b into the desired interior groove 1116.

In another form, the spacer portion 1108 has a non-circular shape, preferably generally oval, or oblong. So configured, the spacer portion 1108 advantageously will not be able to freely rotate between the adjacent spinous processes 12 thereby potentially escaping from the desired position between the spinous processes 12.

As shown in FIG. 45, in another embodiment the second member 1106 includes an engagement portion 1133 configured to engage a tool (not shown) for rotating and retracting the second member 1106 relative to the first member 1104. Any suitable engagement arrangement may be used. As illustrated, in one form, the arms 1122a,b include notches 1134 which are in communication with the slot 1123. The notches 1134 are configured to receive complementary projections of a tool (not shown) for rotating and retracting the second member 1106 relative to the first member 1104 to arrange and secure the implant body 1102 in the extended orientation. In another form, the cylindrical portion 1121 may include a threaded bore at the first end 1126 for threadably receiving a complementary threaded portion of the tool.

With reference to FIGS. 53-56, an implant device 1200 is shown in accordance with another aspect of the invention. Implant device 1200 includes an implant body 1202 including the features of implant body 102 described above. Accordingly, only the differences will be set forth in detail herein. Implant body 1202 may optionally be configured for being implanted at multiple different locations between adjacent vertebrae 10 including, between the spinous processes 12, between laminar regions 14, in an opening in the annulus 16, and or in the intervertebral space 18 between adjacent vertebral bodies 10. In the illustrated form, the implant body 1202 is configured for being positioned between spinous processes 12 of adjacent vertebrae 10.

The implant body 1202 includes a first member 1204 and a second member 1206 adjustably interconnected such that the implant body 1202 can be arranged in a compact orientation, an extended orientation (as shown in FIGS. 53-56), or an intermediate orientation.

The first member 1204 includes a first vertebral engaging portion 1208, and the second member 1206 includes a second vertebral engaging portion 1210. The first and second vertebral engaging portions 1208, 1210 are configured to receive a portion of the spinous processes 12 of the adjacent vertebrae 10. As illustrated, the first vertebral engaging portion 1208 includes a first seat portion 1212 extending between proximal ends of a first arm 1214 and a second arm 1216, and the second vertebral engaging portion 1210 includes a second seat portion 1218 extending between proximal ends of a third arm 1220 and a fourth arm 1222.

Figure 56:
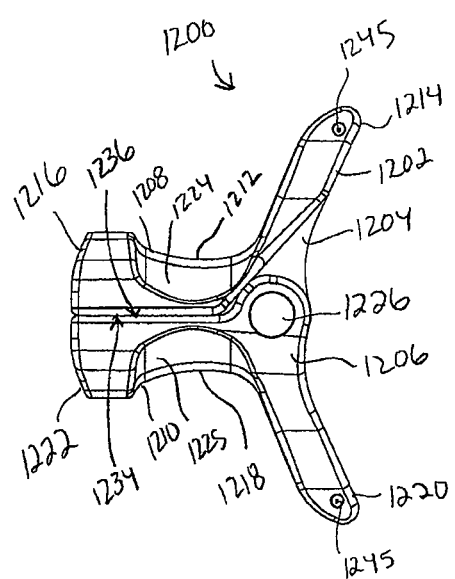
FIG. 56 is a side elevation view of the implant device of FIG. 53.

The first member 1204 additionally includes a first spacer portion 1224 generally extending from the first vertebral engaging portion 1208, and the second member 1206 includes a second spacer portion 1225 extending from the second vertebral engaging portion 1210. As shown in FIG. 56, for example, the first and second spacer portions 1224, 1225 are configured to space apart the first vertebral engaging portion 1208 and the second vertebral engaging portion 1210 when the implant body 1202 is in the extended orientation.

Figure 54:
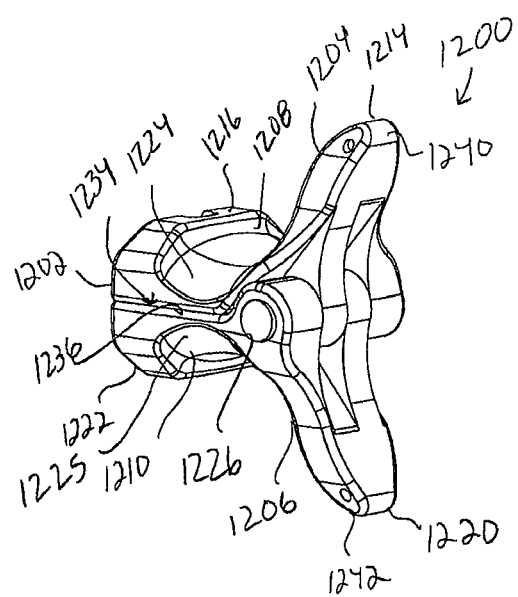
FIG. 54 is another perspective view of the implant device of FIG. 53.
Figure 55:
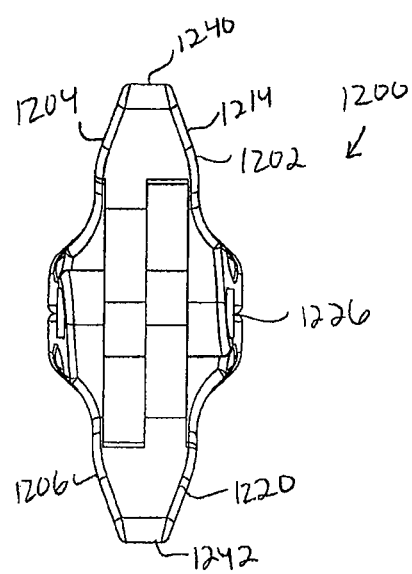
FIG. 55 is a front elevation view of the implant device of FIG. 53.

As shown, for example, in FIGS. 54-55, the first member 1204 and the second member 1206 are pivotably coupled at an adjustable connection 1226 such that the first and second members 1204, 1206 can freely pivot between the compact orientation and extended orientation.

The compact orientation and the extended orientation are defined by the interfering engagement between the first member 1204 and the second member 1206. More specifically, in the compact orientation, a stop arrangement is formed on the first and third arms 1214, 1220 via substantially flat surfaces 1215, 1221 that can be pivoted into substantially flush engagement with each other so that the first arm 1214 of the first member 1204 abuttingly engages the third arm 1220 of the second member 1206. Similarly, in the extended orientation, a stop arrangement is provided via a stop surface 1234 of the first spacer portion 1224 and a stop surface 1236 of the second spacer portion 1225 that can be pivoted into substantially flush engagement with each other so that the stop surface 1234 abuttingly engages the stop surface 1236.

The implant body 1202 is configured such that the first and third arms 1214, 1220 are inserted between the spinous processes 12 of the adjacent vertebrae 10 in the compact orientation and then pivoted to the extended orientation with the first vertebral engaging portion 1208 engaging one of the adjacent spinous processes 12 and the second vertebral engaging portion 1210 engaging the other spinous process 12. In one form, the implant body 1202 is configured to distract the spinous processes 12 to the desired spatial relationship.

The implant body 1202 has a number of features to assist insertion of the implant body 1202 between the adjacent spinous processes 12. In the illustrated form, the first and third arms 1214, 1220 are substantially longer than the second and fourth arms 1216, 1222 to provide a narrow profile for insertion between the spinous processes 12. The first and third arms 1214, 1220 may also have rounded and/or tapered ends 1240, 1242 to ease insertion. As illustrated, implant body 1202 preferably includes radio-opaque markers 1245 embedded therein. Markers 1245 are preferably configured and arranged to allow a surgeon to use radiographic equipment, such as x-ray, to determine the relative size and orientation of the implant body 1202 with respect to the spinous processes 12.

The implant body 1202 is advantageously configured to allow for multiple implant bodies 1202 to be stacked in series between three or more spinous processes 12. As illustrated in FIG. 54-55, arms 1214 and 1220 are arranged in a staggered configuration with arms 1214 and 1220 positioned on opposite sides of a spinous process 12. So configured, the implant bodies 1202 may be inserted in series from one side of the spinous processes 12, the staggered positioning of the implant bodies 1202 preventing undesirable contact between the implant bodies 1202.

With reference to FIGS. 57-62 and 111-127, an implant device 1300 is shown in accordance with another aspect of the invention. Implant device 1300 includes an implant body 1302 including the features of implant body 102 described above. Accordingly, only the differences will be set forth in detail herein. In the illustrated form, the implant body 1302 is configured for being positioned between spinous processes 12 of adjacent vertebrae 10.

The first member 1304 includes a first vertebral engaging portion 1308, and the second member 1306 includes a second vertebral engaging portion 1310. The first and second vertebral engaging portions 1308, 1310 are configured to receive a portion of the spinous processes 12 of the adjacent vertebrae 10. As illustrated, the first vertebral engaging portion 1308 includes a first seat portion 1312 extending between proximal ends of a first arm 1314 and a second arm 1316 and the second vertebral engaging portion 1310 includes a second seat portion 1318 extending between proximal ends of a third arm 1320 and a fourth arm 1322.

Figure 59:
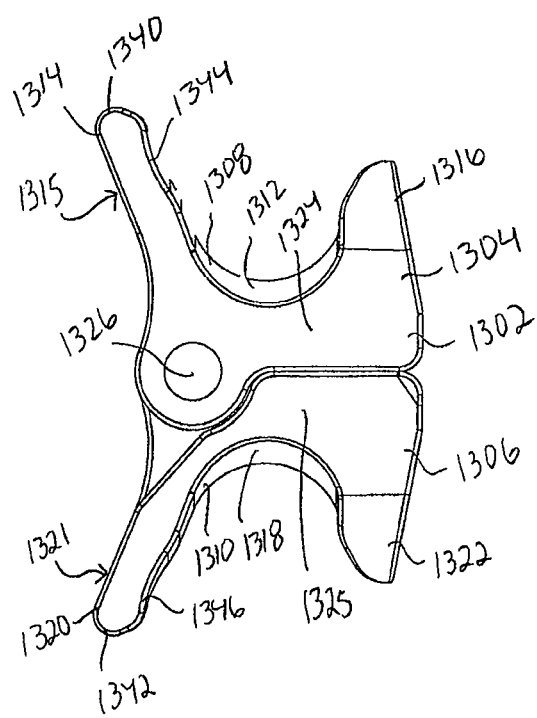
FIG. 59 is a side elevation view of the implant device of FIG. 57 with the implant device shown in an extended orientation.

The first member 1304 additionally includes a first spacer portion 1324 generally extending from the first vertebral engaging portion 1308, and the second member 1306 includes a second spacer portion 1325 extending from the second vertebral engaging portion 1310. As shown in FIG. 59, for example, the first and second spacer portions 1324, 1325 are configured to space apart the first vertebral engaging portion 1308 and the second vertebral engaging portion 1310 when the implant body 1302 is in the extended orientation.

Figure 57A:
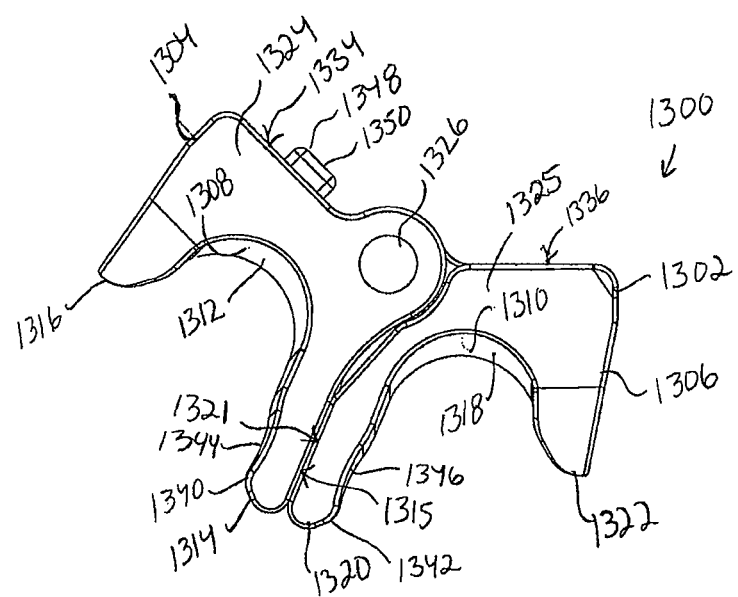
FIG. 57a is a side elevation view of an implant device in accordance with another aspect of the invention with the implant device shown in a compact orientation.
Figure 57B:
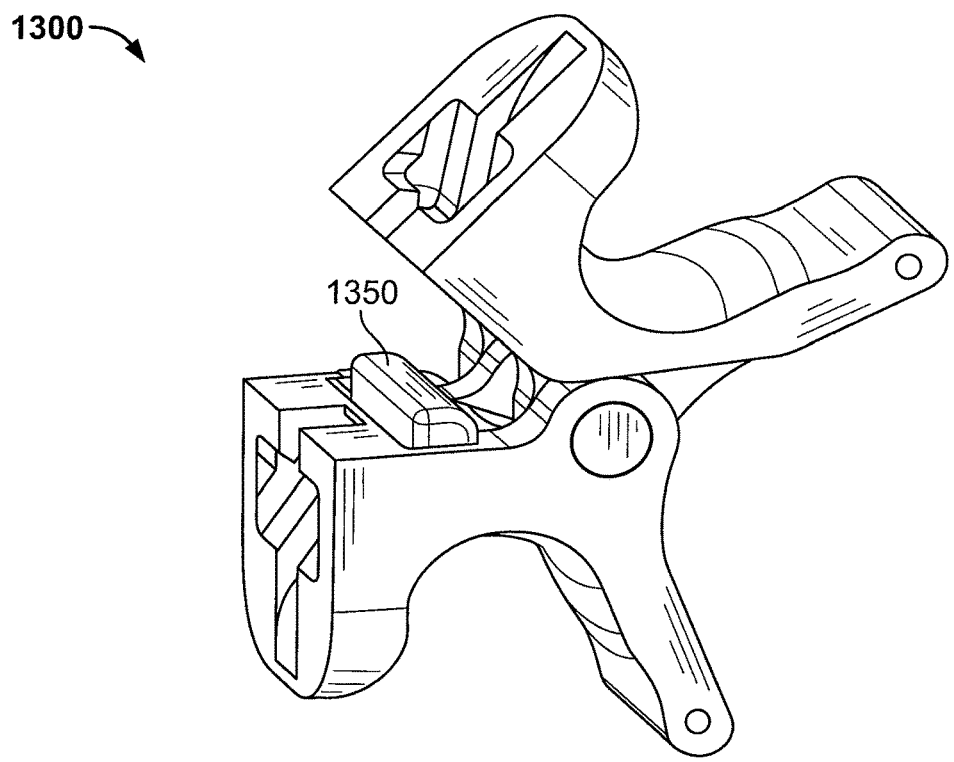
FIG. 57b is a perspective view of the implant device of FIG. 57a with the implant device shown in an intermediate orientation.
Figure 57C:
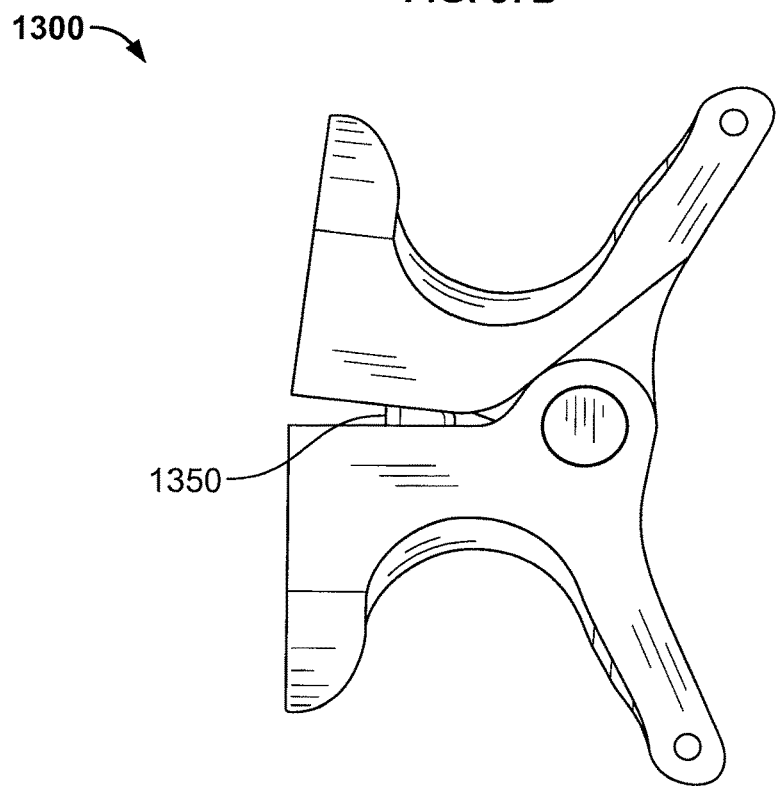
FIG. 57c is a side elevation view of the implant device of FIG. 57a with the implant device shown in the extended orientation.
Figure 58:
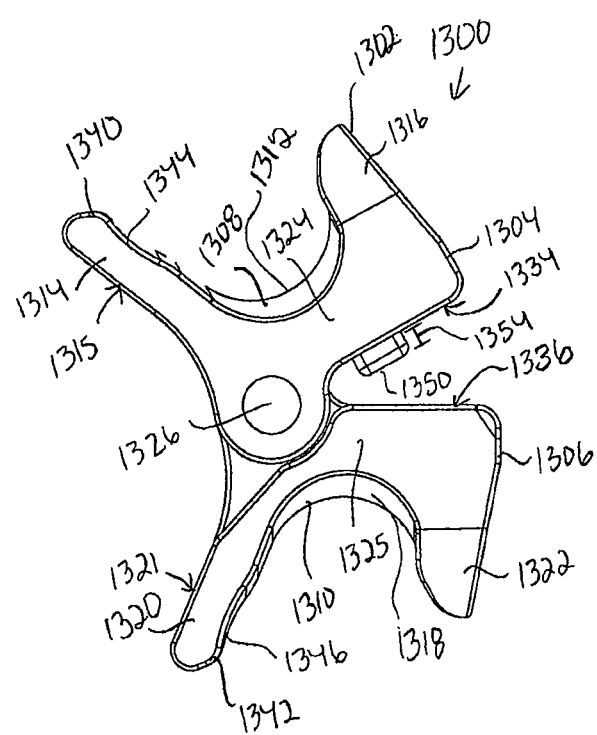
FIG. 58 is a side elevation view of the implant device of FIG. 57 with the implant device shown in an intermediate orientation.
Figure 60:
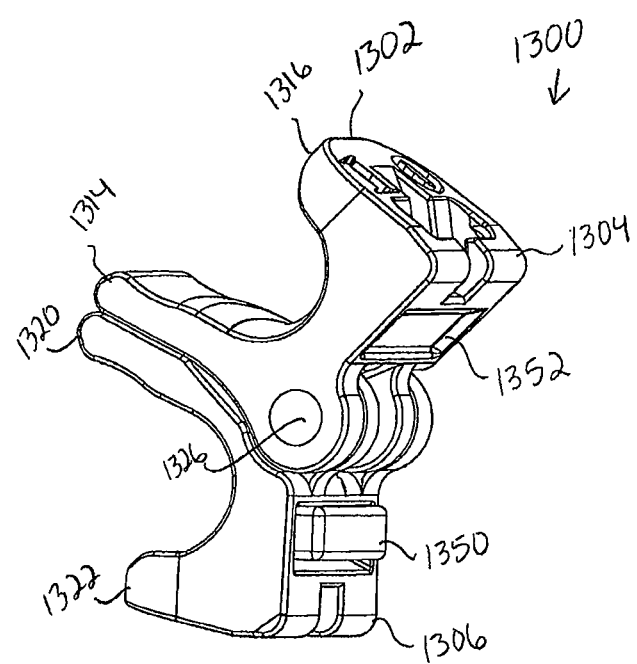
FIG. 60 is a perspective view of the implant device of FIG. 57 with the implant device shown in a compact orientation.
Figure 61:
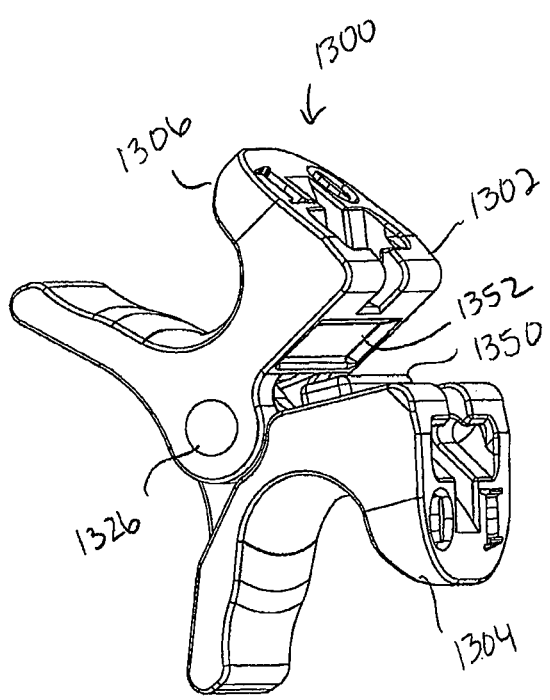
FIG. 61 is a perspective view of the implant device of FIG. 57 with the implant device shown in an intermediate orientation.

As shown, for example, in FIGS. 57-60, the first member 1304 and the second member 1306 are pivotably coupled at an adjustable connection 1326 such that the first and second members 1304, 1306 can freely pivot between a predetermined compact orientation (see FIGS. 57 and 60) and a predetermined extended orientation (see FIGS. 59 and 62), with various intermediate orientations therebetween (such as shown in FIGS. 58 and 61).

The compact orientation and the extended orientation are defined by the interfering engagement between the first member 1304 and the second member 1306. More specifically, as shown in FIG. 57, in the compact orientation, a stop arrangement is formed on the first and third arms 1314, 1320 via substantially flat surfaces 1315, 1321 that can be pivoted into substantially flush engagement with each other so that the first arm 1314 of the first member 1304 abuttingly engages the third arm 1320 of the second member 1306. Similarly, as shown by FIGS. 58 and 59, in the extended orientation, a stop arrangement is provided via a stop surface 1334 of the first spacer portion 1324 and a stop surface 1336 of the second spacer portion 1325 that can be pivoted into substantially flush engagement with each other so that the stop surface 1334 abuttingly engages the stop surface 1336.

As shown, the implant body 1302 is configured to be inserted between the spinous processes 12 of the adjacent vertebrae 10 in the compact orientation and then pivoted to the extended orientation with the first vertebral engaging portion 1308 engaging one of the adjacent spinous processes 12 and the second vertebral engaging portion 1310 engaging the other spinous process 12. In one form, the implant body 1302 is configured to distract the spinous processes 12 to the desired spatial relationship.

The implant body 1302 has a number of features to assist insertion of the implant body 1302 between the adjacent spinous processes 12. As shown, the first and third arms 1314, 1320 are substantially longer than the second and fourth arms 1316, 1322 to provide a narrow profile for insertion between the spinous processes 12. The first and third arms 1314, 1320 may have rounded and/or tapered ends 1340, 1342 to ease insertion. As illustrated in FIGS. 57 and 58, for example, arms 1314, 1320 may also have concave portions 1344, 1346. The concave portions 1344, 1346 assist in properly positioning the implant body 1302 between the spinous processes 12 when the leading arms 1314, 1320 are inserted between the adjacent spinous processes 12. In one embodiment, when the implant body 1302 is inserted, the arms 1314, 1320 are positioned between the adjacent spinous processes 12 such that the spinous processes are seated in the concave portions 1344, 1346. The concave portions 1344, 1346 include ends 1340, 1342, the ends 1340, 1342 being raised portions at the distal ends of the arms 1314, 1320, the ends 1340, 1342 being configured to inhibit the movement of the implant body 1302 so as reduce the potential for undesirable back-out.

As illustrated in FIGS. 57a-c through 62 and 111-127, for example, the implant body 1302 preferably comprises features, such as a bumper 1348, for providing compliance to the implant body 1302 to accommodate natural motion that may take place at the site of implantation.

As illustrated in FIGS. 57*a-c* through 62, the bumper 1348 preferably comprises a projection 1350 extending from one of the stop surfaces 1334, 1336. As illustrated in FIG. 57*a*, the projection 1350 is generally rectangle-shaped, however, as will be understood by those of skill in the art, other configurations may be used including those which accommodate maximum surface contact with the spinous process. Preferably, the projection 1350 is formed of a resilient material, such as polycarbonate urethane, other resilient biocompatible materials, or other suitable material having a low modulus of elasticity. So configured, when the first and second members 1302, 1304 are pivoted to the extended orientation, the projection 1350 extending from one stop surface 1334, 1336 contacts the other stop surface 1334, 1336 to provide a cushioned or soft pivot.

As illustrated in FIGS. 60 and 61, the projection 1350 extending from one of the stop surfaces 1334, 1336 may communicate with a complementary-shaped recess 1352 formed in the other of the stop surfaces 1334, 1336. In one form, as shown in FIGS. 57*c* and 58, the projection 1350 has a height 1354 that is slightly greater than a depth 1356 of the recess 1352. Therefore, when the first and second members 1302, 1304 are pivoted to the extended orientation the communication of the projection 1350 and the recess 1352 provides a soft pivot in which the last 5-10 degrees of rotation are cushioned.

Figure 111:
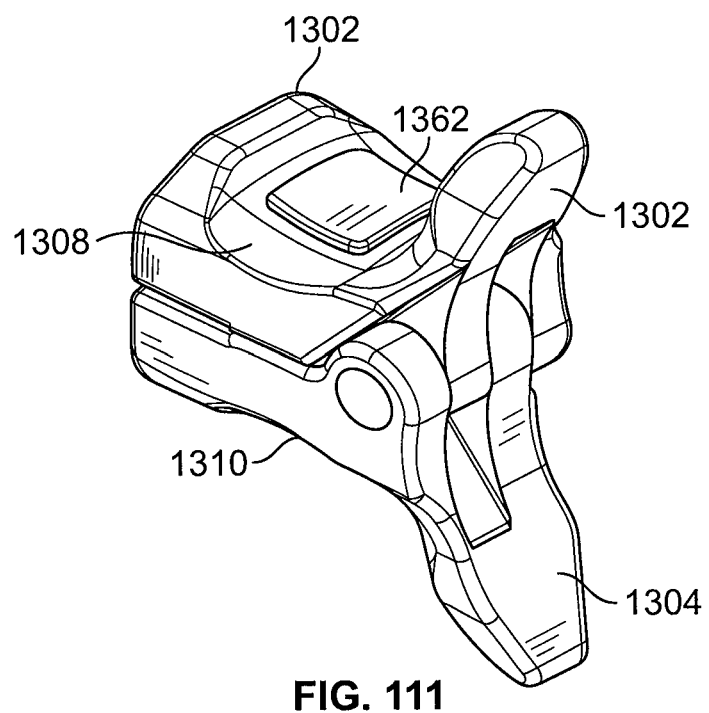
FIG. 111 is a perspective view of an implant device in accordance with another aspect of the invention.
Figure 112:
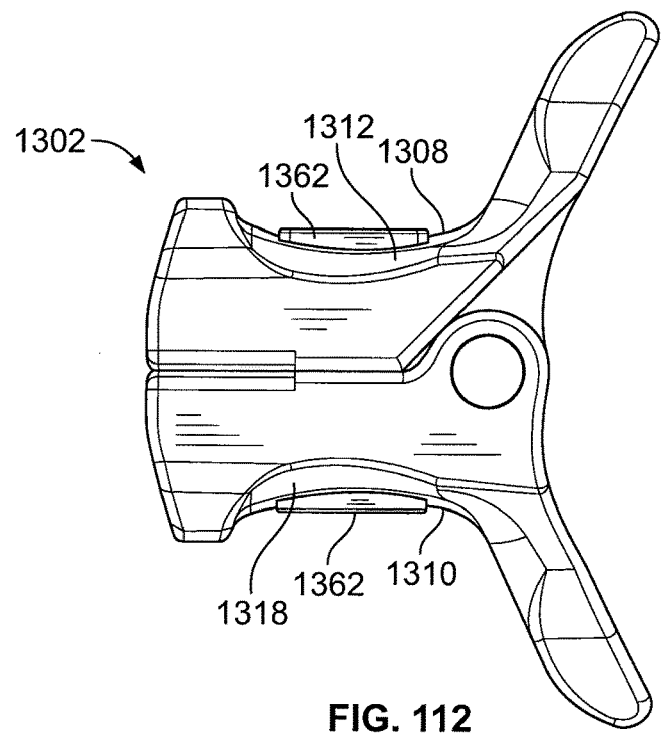
FIG. 112 is a side elevation view of the implant device of FIG. 111 in the extended orientation.
Figure 113:
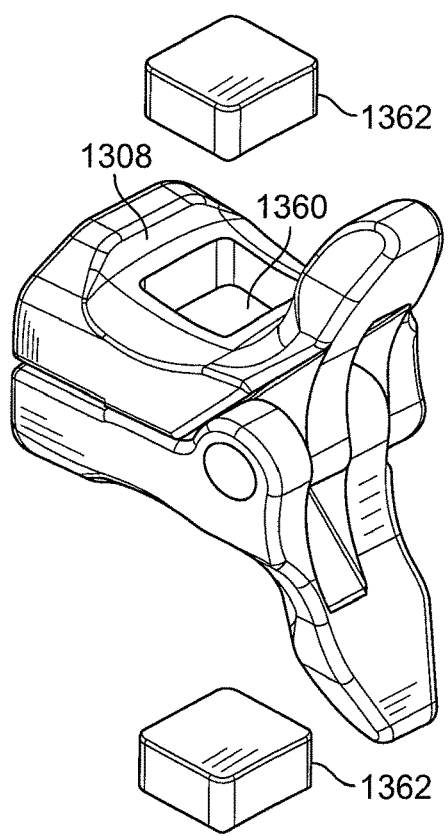
FIG. 113 is a perspective view of the implant device of FIG. 111 with the bumpers removed from the implant body.

As illustrated in FIGS. 111-113, in another embodiment the bumper 1348 comprises a pad 1362 extending from the vertebral engagement portions 1308, 1310. As illustrated in FIG. 113, the pad 1362 is generally square-shaped, however, as will be understood by those of skill in the art, other configurations may be used including those which accommodate maximum surface contact with the spinous process 12. Preferably, the projection 1350 is formed of a resilient material, such as polycarbonate urethane, other resilient biocompatible materials, or other suitable material having a low modulus of elasticity. The pad 1362 is configured to communicate with a complementary shaped recess 1360 formed in the vertebral engagement portion 1308, 1310. Preferably, the depth of the recess 1360 is less than the height of the pad 1362. More preferably, the height of the pad 1362 and depth of the recess 1360 are such that the spinous process 12 does not engage the seats 1312, 1318 of the implant body 1302. So configured, when the first and second members 1302, 1304 are pivoted to the extended orientation, the projection 1350 is oriented to engage a spinous process 12, providing a cushion for the communication of the spinous process 12 with the implant body 1302. Preferably, the depth of the recess 1360 and the height of the pad 1362 are configured such that upon high impact loading on the implant body 1302 the spinous process 12 engages the seat 1312, 1318 of the implant body 1302 before over compression of the pad 1362 occurs.

Figure 114:
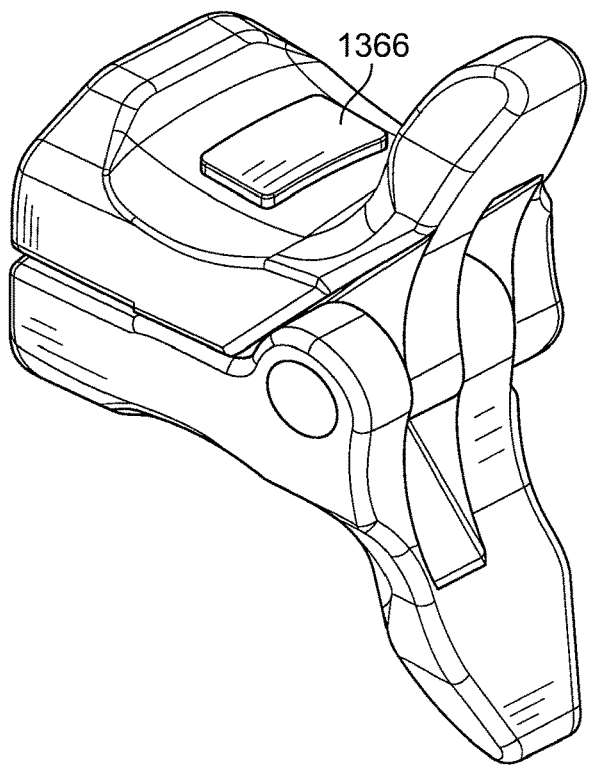
FIG. 114 is a perspective view of an implant device in accordance with another aspect of the invention.
Figure 115:
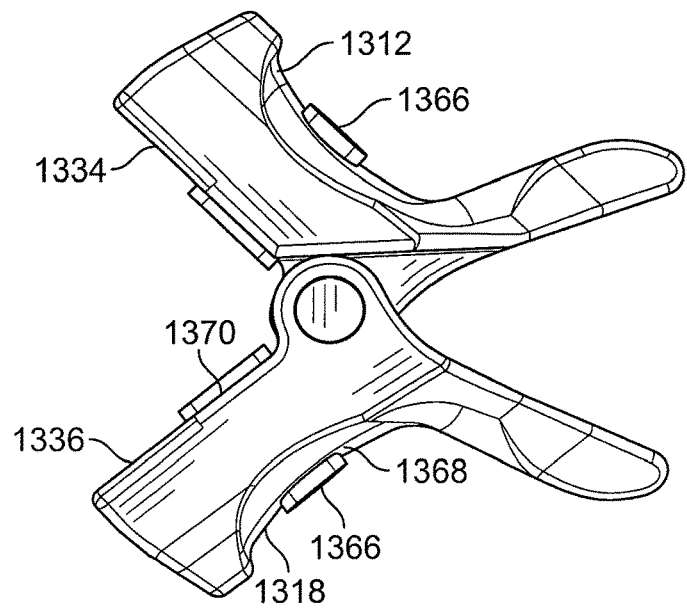
FIG. 115 is a side elevation view of the implant device of FIG. 115 in an intermediate orientation.
Figure 116:
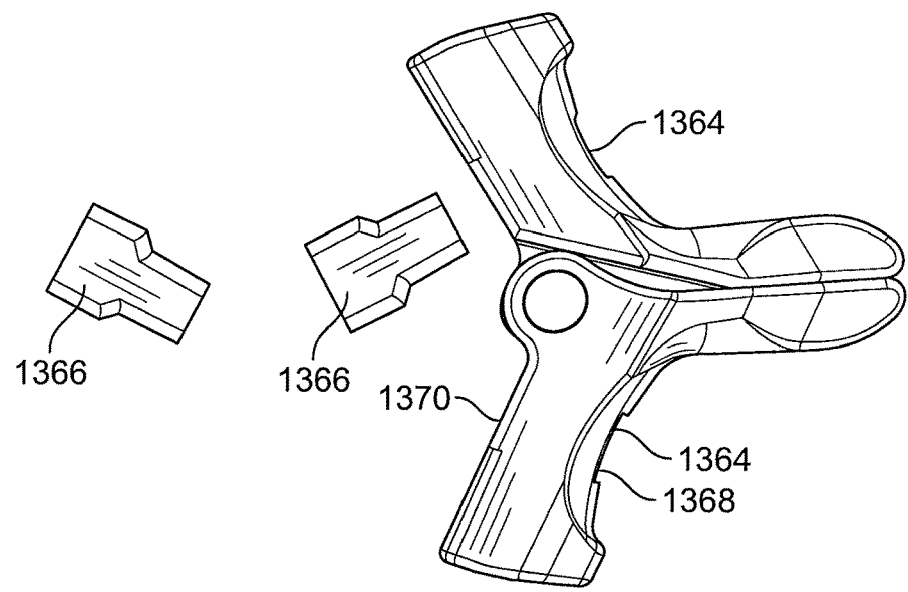
FIG. 116 is a side elevation view of the implant device of FIG. 115 in an intermediate orientation with the bumpers removed from the implant body.
Figure 117:
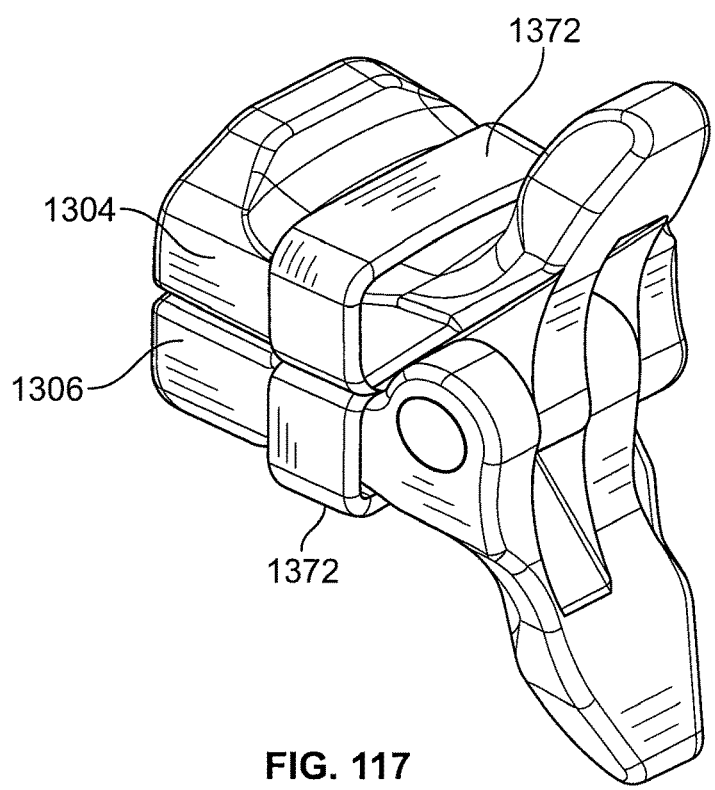
FIG. 117 is a perspective view of an implant device in accordance with another aspect of the invention.
Figure 118:
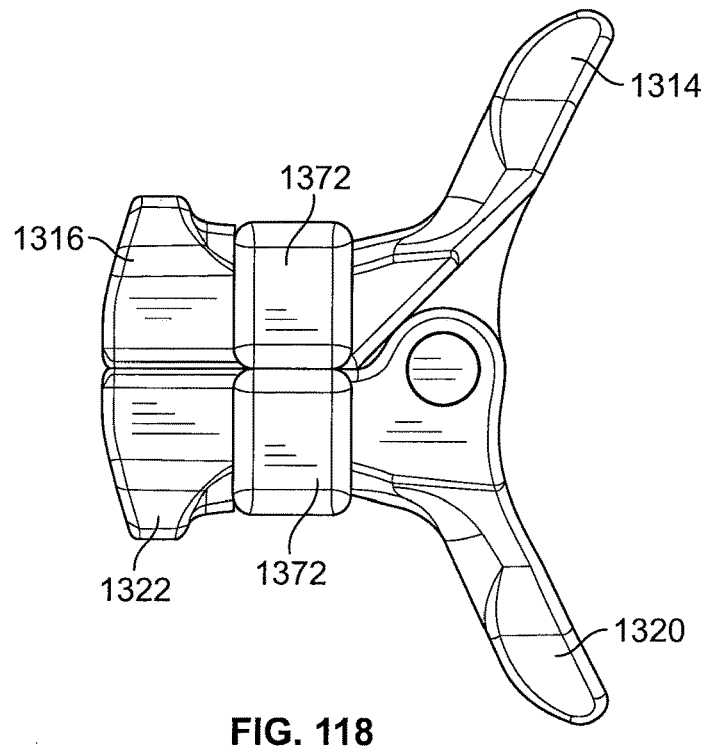
FIG. 118 is a side elevation view of the implant device of FIG. 117 in the extended orientation.
Figure 120:
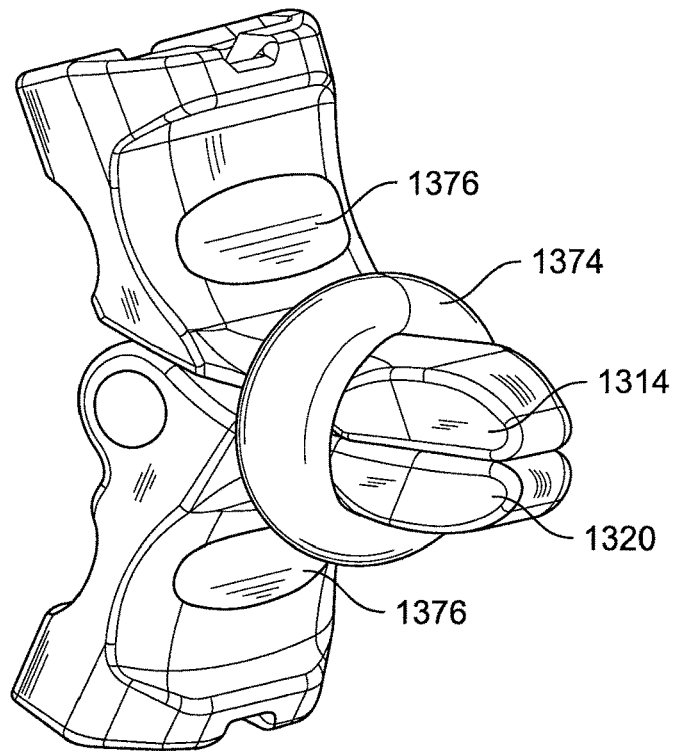
FIG. 120 is a perspective view of an implant device in accordance with another aspect of the invention.
Figure 119:
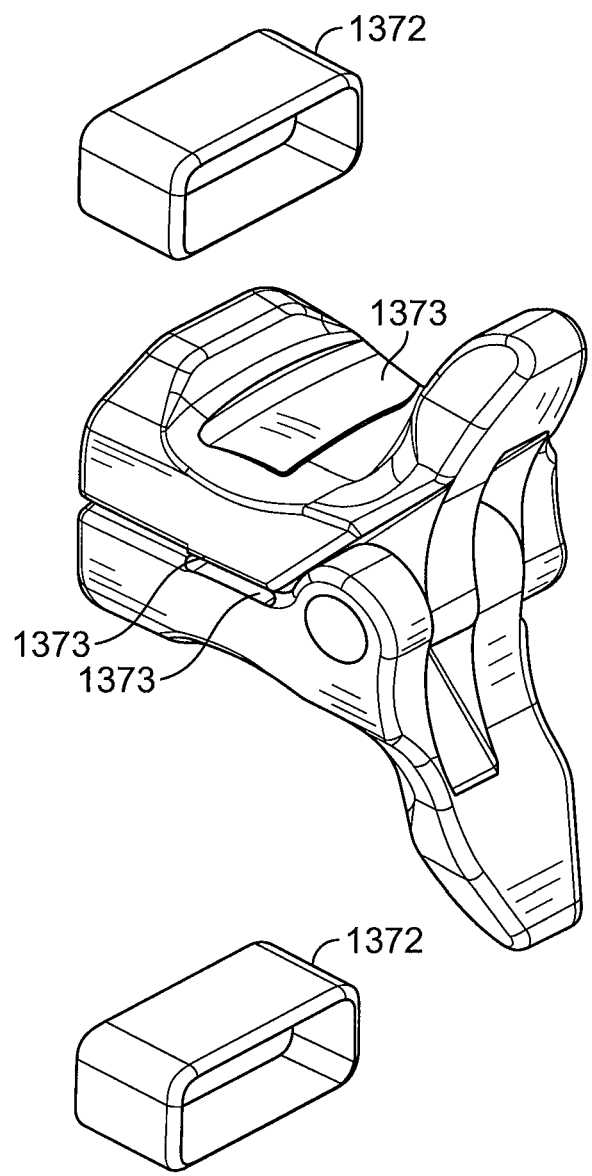
FIG. 119 is a perspective view of the implant device of FIG. 117 in the extended orientation showing the bumper bands removed from the implant body.
Figure 121:
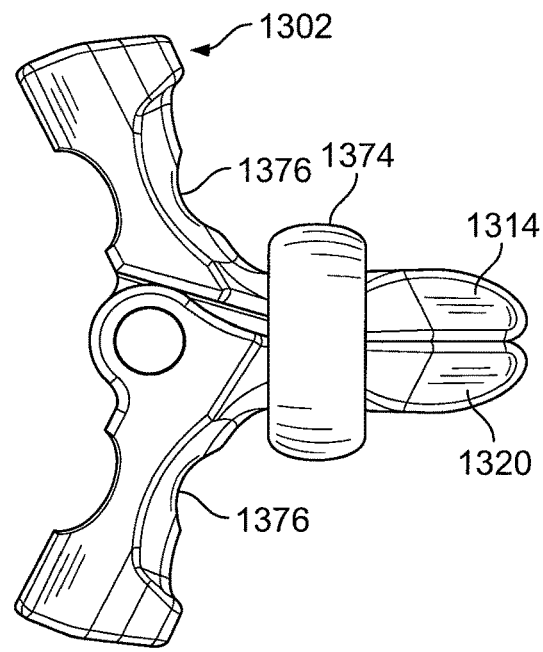
FIG. 121 is a side elevation view of the implant device of FIG. 120 in the compact orientation.
Figure 122:
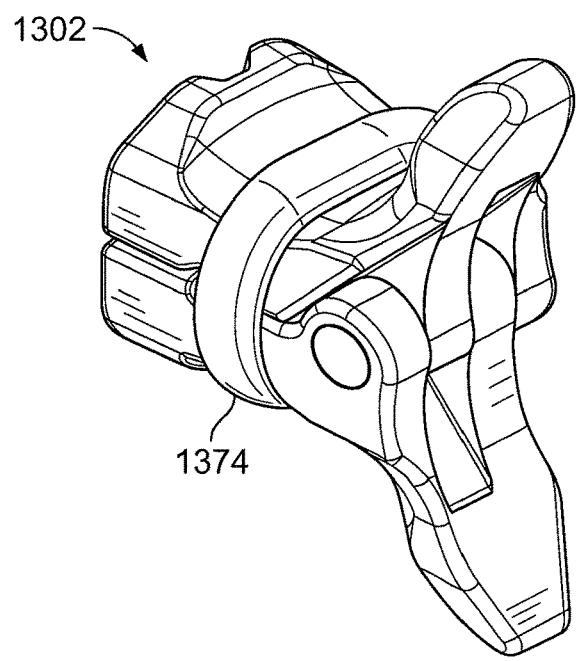
FIG. 122 is a perspective view of the implant device of FIG. 120 in the extended orientation.
Figure 123:
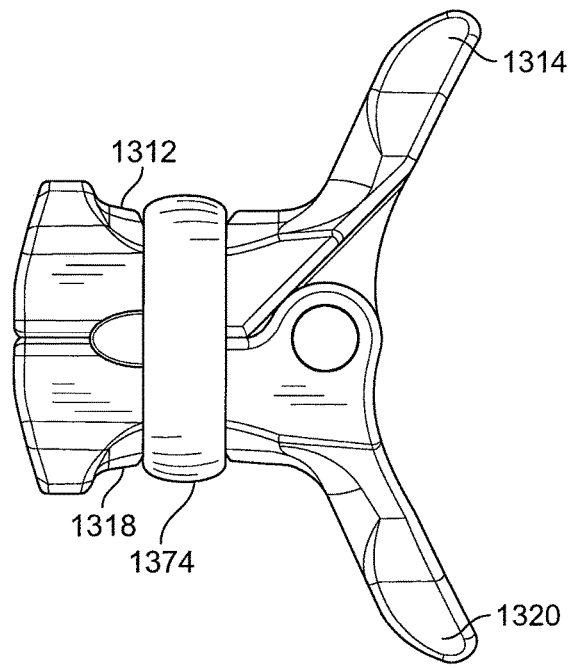
FIG. 123 is a side elevation view of the implant device of FIG. 120 in the extended orientation.
Figure 124:
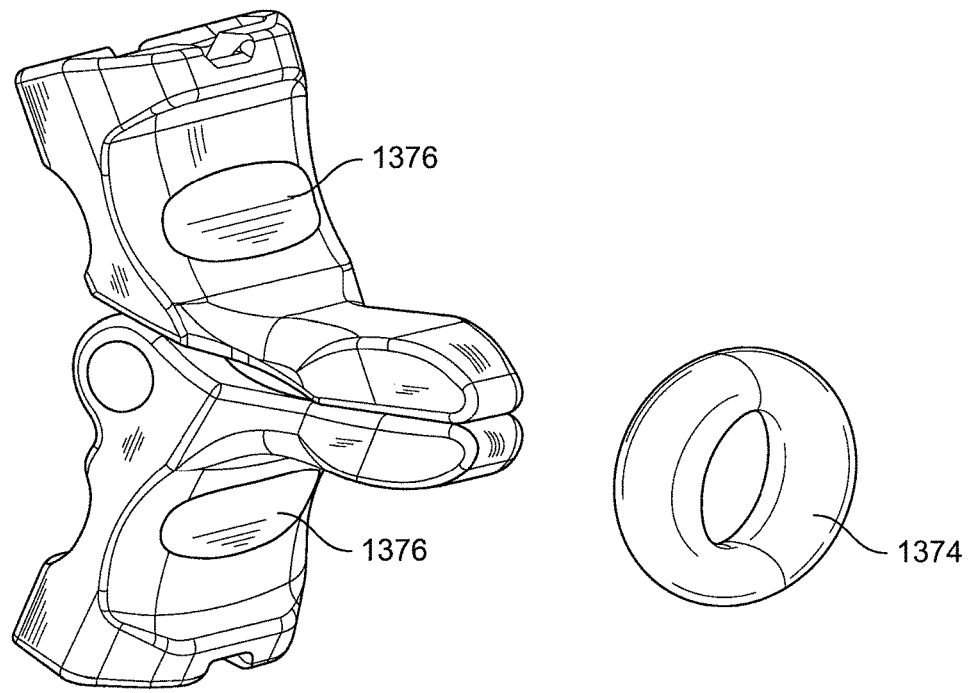
FIG. 124 is a perspective view of the implant device of FIG. 120 in the compact orientation showing the bumper band removed from the implant body.

In another embodiment, as shown in FIGS. 114-116, the first and second members 1304, 1306 comprise pad apertures 1364 and pads 1366. The pad apertures 1364 preferably extend through seats 1312, 1318 to stop surfaces 1334, 1336 such that they include both seat portion apertures 1368 and stop surface apertures 1370 configured to receive the pads 1366 therein. The pads 1366 are configured to extend through the pad apertures 1364. Preferably, the pads 1366 are configured to extend beyond both the seats 1312, 1318 and stop surfaces 1334, 1336. Preferably, the pad aperture is configured such that the seat portion aperture 1368 is not the same size and shape as the stop surface aperture 1370. Preferably, the size of the seat portion aperture 1368 is less than the size of the stop surface aperture 1370. It will be understood by those of skill in the art that configurations of the pad aperture 1364 and pad 1366 other than those illustrated in FIGS. 114-116 may be used, including those which accommodate maximum surface contact with the spinous process. Preferably, the pad 1366 is formed of a resilient material, such as polycarbonate urethane, other resilient biocompatible materials, or other suitable material having a low modulus of elasticity. So configured, when the first and second members 1302, 1304 are pivoted to the extended orientation, the pad 1366 extending from one stop surface 1334, 1336 contacts the pad 1366 extending from the other stop surface 1334, 1336 to provide a cushioned or soft pivot in which the last 5-10 degrees of rotation are cushioned. The pads 1366 also provide a cushion for the communication of the spinous process 12 with the implant body 1302. Preferably, the pads 1366 and the pad apertures 1364 are configured such that upon high impact loading on the implant body 1302 the spinous process 12 engages the seat 1312, 1318 of the implant body 1302 before over compression of the pad 1366 occurs.

An alternative compliance feature is shown in FIGS. 117-124. In FIGS. 117-120, a pair of bands 1372 are positioned around the first and second members 1304, 1306. Preferably, the bands 1372 are disposed around the first member 1304 between the first and second arms 1314, 1316 and around the second member 1306 between the third and fourth arms 1320, 1322. Preferably, the first and second member 1304, 1306 have grooves 1373 formed therein to accept the bands 1372. As illustrated, the bands 1372 have flat surfaces, but it will be understood by those of skill in the art that other configurations may be used including those which accommodate maximum surface contact with the spinous process. Preferably, the band 1372 is formed of a resilient material, such as polycarbonate urethane, other resilient biocompatible materials, or other biocompatible material having a suitably low modulus of elasticity. In one embodiment, the bands 1372 and grooves 1373 are configured such that when the first and second members 1304, 1306 are pivoted to the extended orientation, band 1372 positioned around the first member 1304 and band 1372 positioned around the second member 1306 engage one another to provide a cushioned or soft pivot, while also providing a cushion for the communication of the spinous process 12 with the implant body 1302. In an alternative embodiment, the bands 1372 and grooves 1373 are configured such that when the first and second members 1303, 1306 are pivoted to the extended orientation the stop surfaces 1334, 1336 are engaged. Preferably, the bands 1372 and grooves 1373 are configured such that upon high impact loading on the implant body 1302 the spinous process 12 engages the seat 1312, 1318 before over compression of the bands 1372 occurs.

In another embodiment, only one band 1374 is positioned on the implant body 1302. Preferably, the band 1374 is configured to be disposed around the first and third arms 1314, 1320 with the implant body 1302 in the compact orientation and prior to insertion. When the implant body 1302 is pivoted to the extended orientation, the band 1374 is repositioned (e.g., by sliding or rolling) from being disposed around the first and third arms 1314, 1320 to being disposed around the seat portions 1312, 1318 of the implant body 1302. Preferably, the seat portions 1312, 1318 comprise a groove 1376, the groove 1376 being configured to accept the band 1374 and inhibit further movement of the band 1374 upon repositioning of the implant body 1302 to the extended orientation. As illustrated, the band 1374 has rounded surfaces, but it will be understood by those of skill in the art that other configurations may be used other configurations may be used including those which accommodate maximum surface contact with the spinous process. Preferably, the band 1374 is formed of a resilient material, such as polycarbonate urethane or other resilient biocompatible materials having a low modulus of elasticity. So configured, when inserted between adjacent spinous processes 12, the band 1374 engages the spinous process 12 to provide a cushioned engagement between the implant body 1302 and the spinous process 12. Preferably, the bands 1374 and grooves 1376 are configured such that upon high impact loading on the implant body 1302 the spinous process engages the seat 1312, 1318 before over compression of the bands 1374 occurs.

Figure 125:
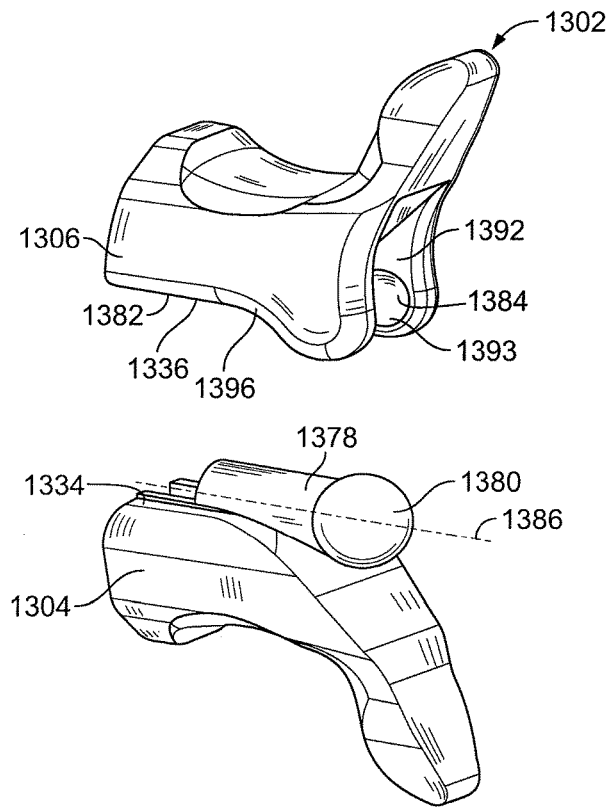
FIG. 125 is a perspective view of an implant device in accordance with another aspect of the invention, the implant body members separated showing the cylindrical and spherical portions.
Figure 126:
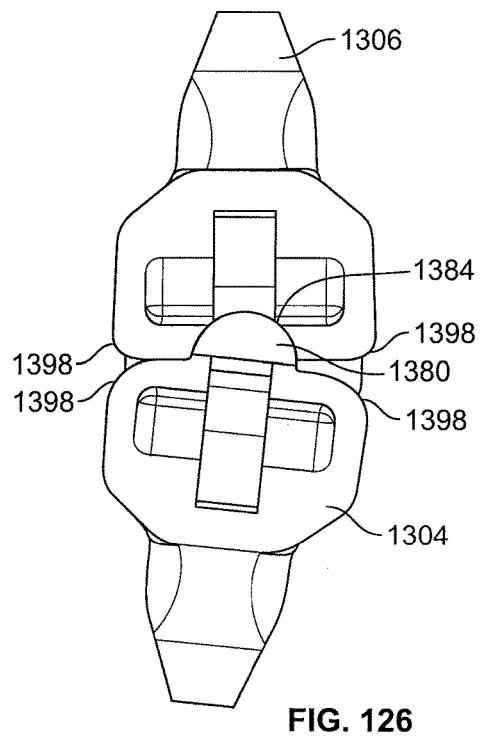
FIG. 126 is a end elevation view of the implant device of FIG. 125 in the extended orientation showing the implant body adjusted to one side.
Figure 127:
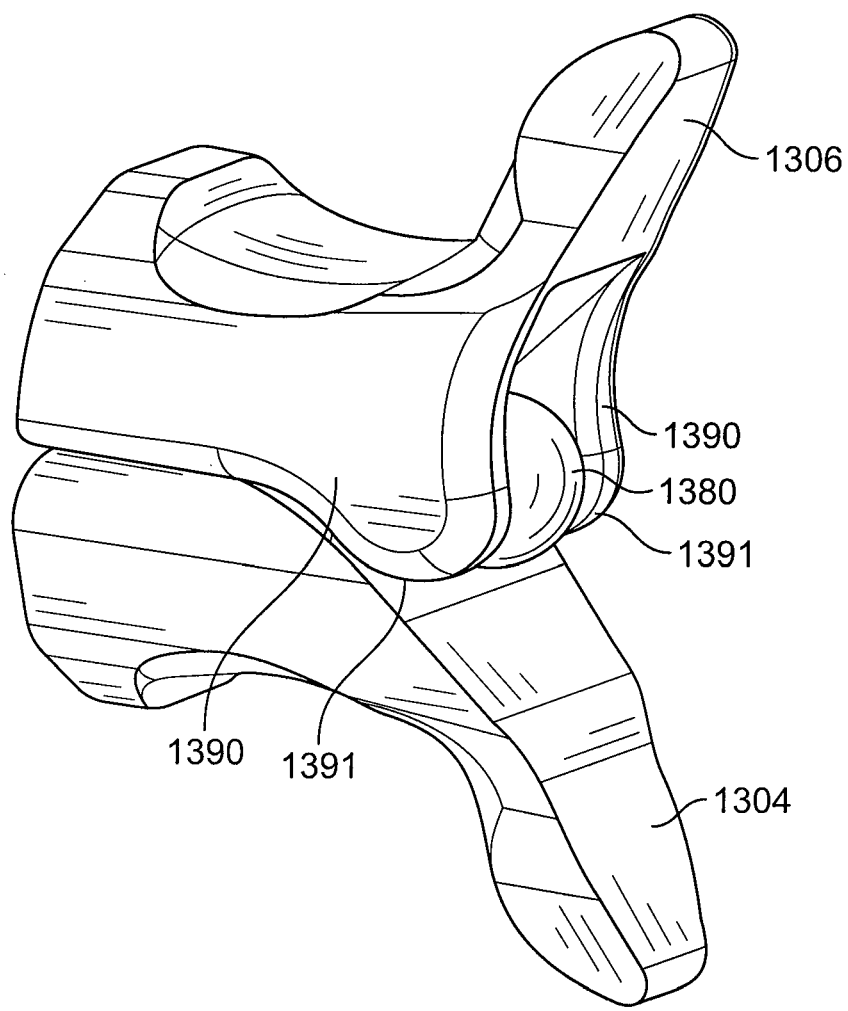
FIG. 127 is a perspective view of the implant device of FIG. 125 in the extended orientation.

Another compliance feature is illustrated in FIGS. 125-127 provides the implant body 1302 with additional degrees of freedom of movement. In one embodiment, the implant body comprises a first member 1304, a second member 1306 and a spherical portion 1380. The first and second members receive the spherical portion at the adjustable connection 1326. The implant body 1302 is configured to permit rotation around two axes, the axes being generally orthogonal. Rotation around the first axis permits the implant body to be shifted from the compact orientation to the extended orientation, and rotation around the second axis permits the implant body to shift when in the extended orientation to accommodate natural movement.

Preferably, the first member 1304 comprises a cylindrical portion 1378 and a spherical portion 1380. The cylindrical portion 1378 is connected to the first member 1340 and extends along the first axis 1386. In one embodiment, the cylindrical portion 1378 is integral with the first member. Preferably, the cylindrical portion 1378 connects to a recess (not shown) in the stop surface 1334. The spherical portion 1380 is connected to one end of the cylindrical portion 1380, the spherical portion 1380 being positioned where the adjustable connection 1326 is found in other embodiments. The spherical portion 1380 is preferably positioned where the adjustable connection 1326 would normally be located. In a preferable embodiment, the cylindrical portion includes a first end with a concave surface configured to engage the spherical portion (not shown). Preferably, the spherical portion 1380 has a larger diameter than the cylindrical portion 1378. The stop surface 1334 is configured to extend along the cylindrical portion toward the spherical portion. At a point along the cylindrical portion, the first spacer portion 1324 chamfers toward the first arm 1314 such that the spherical portion 1380 minimally engages the first member 1304.

The second member 1306 comprises a cylindrical accepting portion 1382 and a spherical accepting portion 1384. The spherical accepting portion 1384 is located on the second member 1306 where the adjustable connection 1326 would normally be found and is configured to securely receive the spherical portion 1380 of the first member 1304 therein. The spherical accepting portion comprises a pair of depending spaced boss portions 1390 extending from the stop surface 1336. Each boss 1390 includes a distal end 1391 and an inner surface 1392, the inner surface including a concave portion 1393 configured to accept the spherical portion 1380 therein. The distal end 1391 is configured to engage the chamfered portion of the first spacer portion 1324 of the first member 1304 when shifting the implant body 1302 from the compact to extended orientation. Preferably, the depending spaced boss portions 1390 of the spherical accepting portion 1384 and the spherical portion 1380 are configured so as to act as a multi-axial bearing or pivot connection, permitting the spherical portion 1380 to freely rotate within the spherical accepting portion 1384 while resisting the expulsion of the spherical portion 1380 from the spherical accepting portion 1384.

The cylindrical accepting portion 1382 extends from the spherical accepting portion 1384 along the stop surface 1336 of the fourth arm 1322 and is configured to receive the cylindrical portion 1378 of the first member 1304 therein. Preferably, the cylindrical accepting portion 1382 comprises a recess 1396 configured to accept the cylindrical portion 1378 while maintaining a distance between the stop surfaces 1334, 1336 of the first and second members 1304, 1306. The distance between the stop surfaces 1334, 1336 permits the first and second member 1304, 1306 to rotate a distance limited by the distance between the stop surfaces 1334, 1336 about the second axis 1388 when in the extended orientation. In addition, the stop surfaces 1334, 1336 of the first and second members 1304, 1306 have rounded corners 1398 on opposite sides of the cylinder portion 1378 and cylinder accepting portion 1382 respectively. The rounded corners 1398 permit the implant body 1302 further freedom of movement along the second axis 1388 in the extended orientation. Additionally, the cylindrical portion 1378 and cylindrical accepting portion 1382 act to limit the freedom of movement of the implant body, specifically limiting the available rotation to two orthogonal axes.

Therefore, the spherical portion 1380, the cylindrical portion 1378, the spherical accepting portion 1384 and the cylindrical accepting portion 1382 are configured to permit the spherical accepting portion 1384 and cylindrical accepting portion 1382 to securely rotate a limited distance around the cylindrical portion 1378 and the spherical portion 1380 around axis 1386, thereby providing additional compliance to the implant body 1302 to accommodate natural motion that may take place at the site of implantation.

In one embodiment, the first member comprises one unitary member comprising the cylindrical portion 1378 and the spherical portion 1380. In a preferred embodiment, the first member 1302 comprises several distinct pieces connected to each other. In one preferred form, the cylindrical portion 1378 and spherical portion 1380 are comprised of titanium, titanium coated with PEEK, PEEK, or any other materials suitable for forming the implant bodies. In another preferred form, the cylindrical portion 1378 is formed of a resilient material, such as polycarbonate urethane or other resilient biocompatible materials having a low modulus of elasticity.

In a preferred embodiment, the cylindrical portion 1378 is coated with a resilient material, such as polycarbonate urethane or other resilient biocompatible materials having a low modulus of elasticity. In a preferred embodiment, the cylindrical accepting portion 1382 is lined with a resilient material, such as polycarbonate urethane, other resilient biocompatible materials, or any material having a low modulus of elasticity. So configured, the engagement of the cylindrical portion 1378 and cylindrical accepting portion 1382 provides additional compliance to the implant body 1302 by providing a soft pivot for the last 5-10 degrees toward the extended orientation.

In another embodiment, combinations of the bands, pads, etc. described above may be used. As herein described, the soft pivot created by the various embodiments of the implant body including pads, bumpers, bands, etc provides the additional advantage of diminishing wear on the pin 1326 of the adjustable connection.

Figure 63:
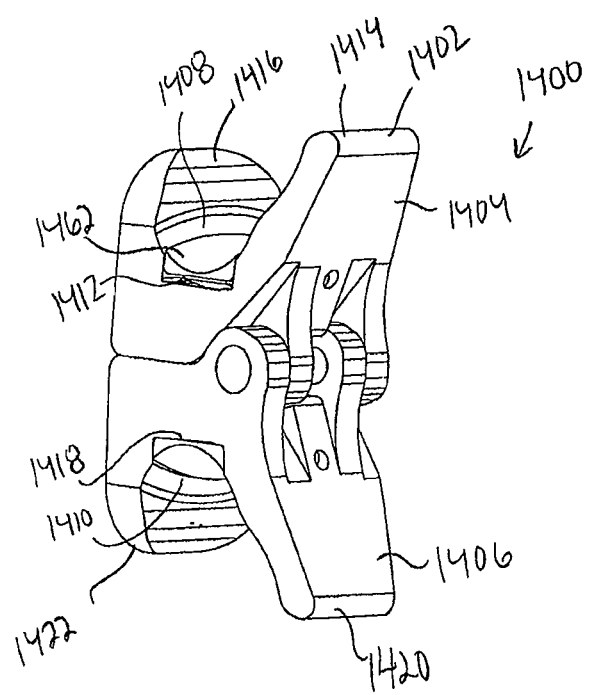
FIG. 63 is a perspective view of an implant device in accordance with another aspect of the invention with the implant device shown in an extended orientation.
Figure 64:
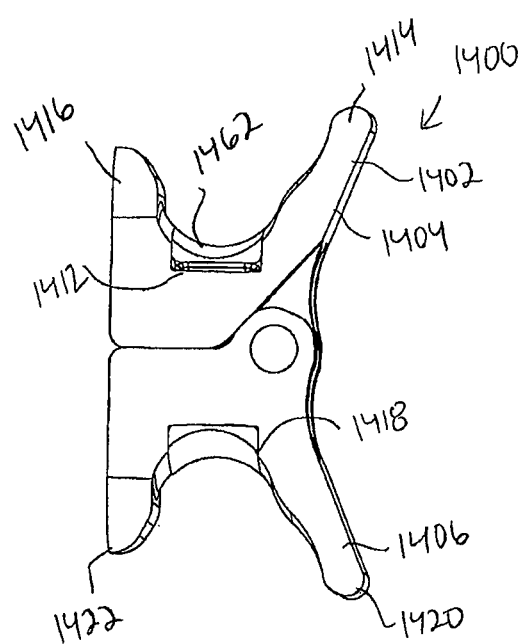
FIG. 64 is a side elevation view of the implant device of FIG. 63 with the implant device shown in an extended orientation.
Figure 65:
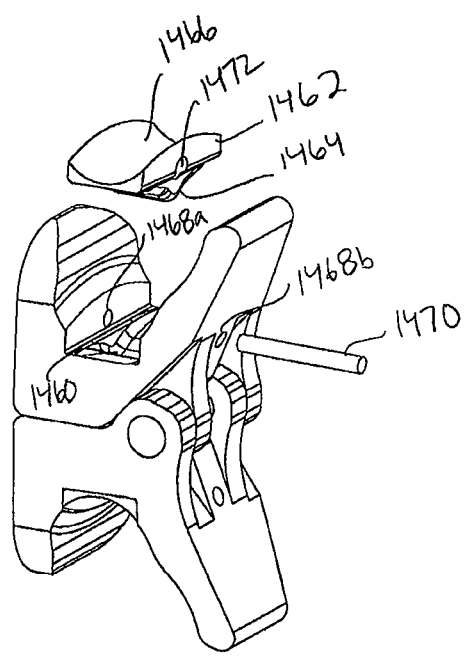
FIG. 65 is an exploded view of the implant device of FIG. 63.

Referring now to FIGS. 63-65, an implant device 1400 is shown in accordance with another aspect of the invention. Implant device 1400 includes an implant body 1402 including the features of implant bodies 102 and 1402 described above. Accordingly, only the differences will be set forth in detail herein.

The implant body 1402 includes a first member 1404 and a second member 1406 adjustably interconnected such that the implant body 1402 can be arranged in a compact orientation or an extended orientation. The first member 1404 includes a first vertebral engaging portion 1408, and the second member 1406 includes a second vertebral engaging portion 1410, each of which is configured to receive a portion of the spinous process 12 of the adjacent vertebrae 10.

As illustrated, the first vertebral engaging portion 1408 includes a first seat portion 1412 extending between proximal ends of a first arm 1414 and a second arm 1416, and the second vertebral engaging portion 1410 includes a second seat portion 1418 extending between proximal ends of a third arm 1420 and a fourth arm 1422.

As illustrated, in one form, the implant body 1402 comprises an alternative compliance feature to accommodate natural motion that may take place at the site of implantation. As shown in FIG. 65, at least one of the first and second seat portions 1412, 1418 comprises a socket 1460 defined therein configured to receive a moveable saddle 1462. The moveable saddle 1462 comprises an elongated ball portion 1464 configured to be received by the socket 1460. An interface portion 1466 extends therefrom and is configured to interface with a portion of the spinous process 12.

As shown in FIG. 65, the seat portions 1412, 1418 include bores 1468a,b therein for receiving a pin 1470 defined therethrough. The moveable saddle 1462 likewise has a bore 1472 therethrough that aligns with bores 1468a, b with the ball portion 1464 of the moveable saddle 1462 received in the socket 1460. Pin 1470 is received through bores 1468a, b and bore 1472 to secure the moveable saddle 1462 in the socket 1460. As illustrated, in one form, the bore 1472 is somewhat larger in diameter than the diameter of the pin 1470. Therefore, the moveable saddle 1462 has room to move slightly upward, downward, forward, and/or backward relative to the pin 1470 depending on the forces applied to the implant body 1402.

In one form, the moveable saddle 1462 may be formed of the same material as the implant body 1402 or of another suitable biocompatible material. The pin 1470 is preferably formed of titanium or other suitable biocompatible material.

Figure 66:
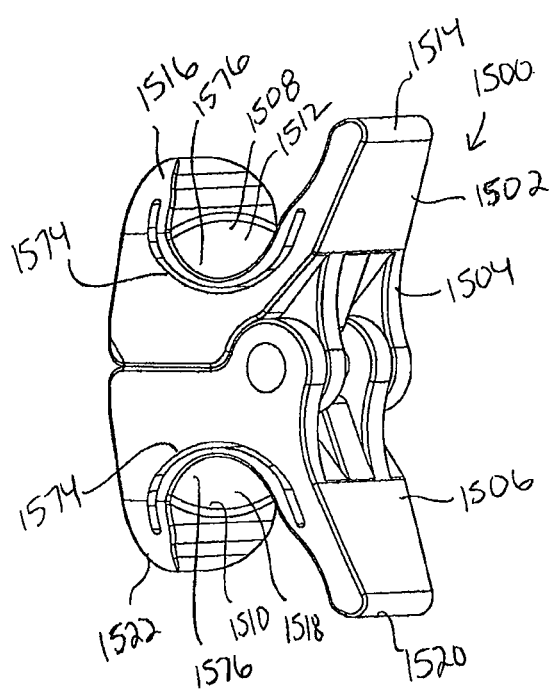
FIG. 66 is a perspective view of an implant device in accordance with another aspect of the invention with the implant device shown in an extended orientation.
Figure 67:
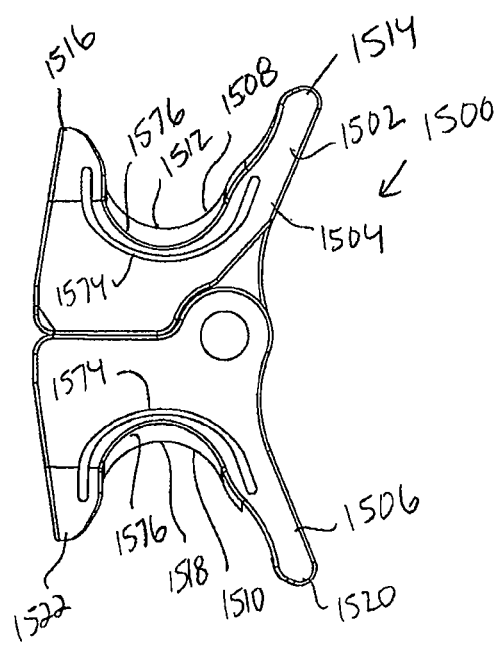
FIG. 67 is a side elevation view of the implant device of FIG. 66 with the implant device shown in an extended orientation.

Referring now to FIGS. 66 and 67, an implant device 1500 is shown in accordance with another aspect of the invention. Implant device 1500 includes an implant body 1502 including the features of implant bodies 102, 1202, 1302 and 1402 described above. Accordingly, only the differences will be set forth in detail herein.

The implant body 1502 includes a first member 1504 and a second member 1506 adjustably interconnected such that the implant body 1502 can be arranged in a compact orientation or an extended orientation. The first member 1504 includes a first vertebral engaging portion 1508, and the second member 1506 includes a second vertebral engaging portion 1510, each of which is configured to receive a portion of the spinous process 12 of the adjacent vertebrae 10.

As illustrated, the first vertebral engaging portion 1508 includes a first seat portion 1512 extending between proximal ends of a first arm 1514 and a second arm 1516 and the second vertebral engaging portion 1510 includes a second seat portion 1518 extending between proximal ends of a third arm 1520 and a fourth arm 1522. As illustrated, the first and second seat portions 1512, 1518 are preferably generally U-shaped.

As shown in FIGS. 66 and 67, the implant body 1502 comprises yet another alternative compliance feature to accommodate natural motion that may take place at the site of implantation. In implant body 1502, at least one of the generally U-shaped first and second seat portions 1512, 1518 comprises a generally U-shaped groove 1574 formed therethrough. The groove 1574 defines a resiliently deflectable saddle 1576 thereabove that can move slightly downward and/or upward depending on the forces applied to the implant body 1502.

Figure 53:
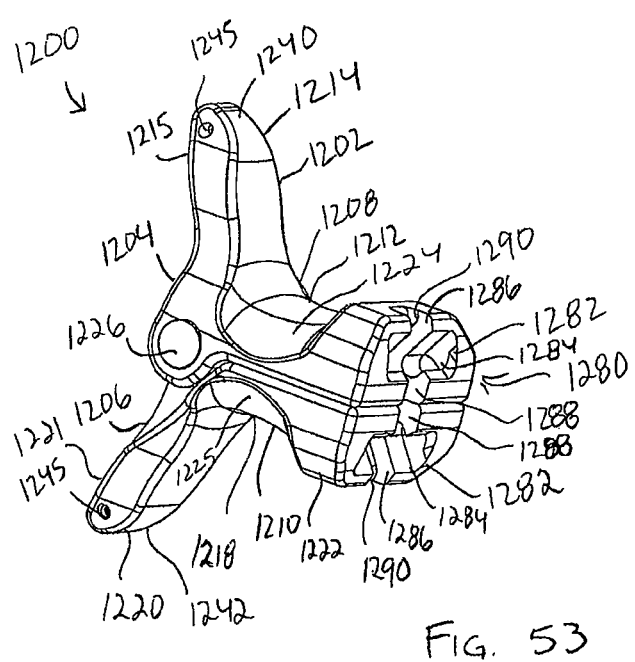
FIG. 53 is a perspective view of an implant device in accordance with another aspect of the invention.
Figure 62:
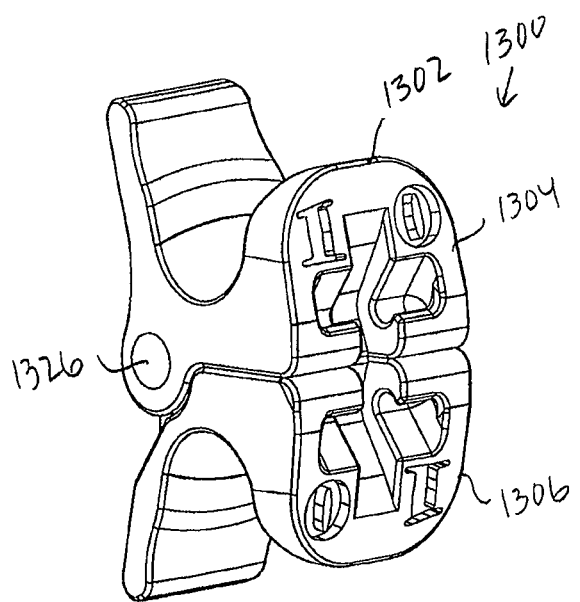
FIG. 62 is a perspective view of the implant device of FIG. 57 with the implant device shown in an extended orientation.
Figure 77:
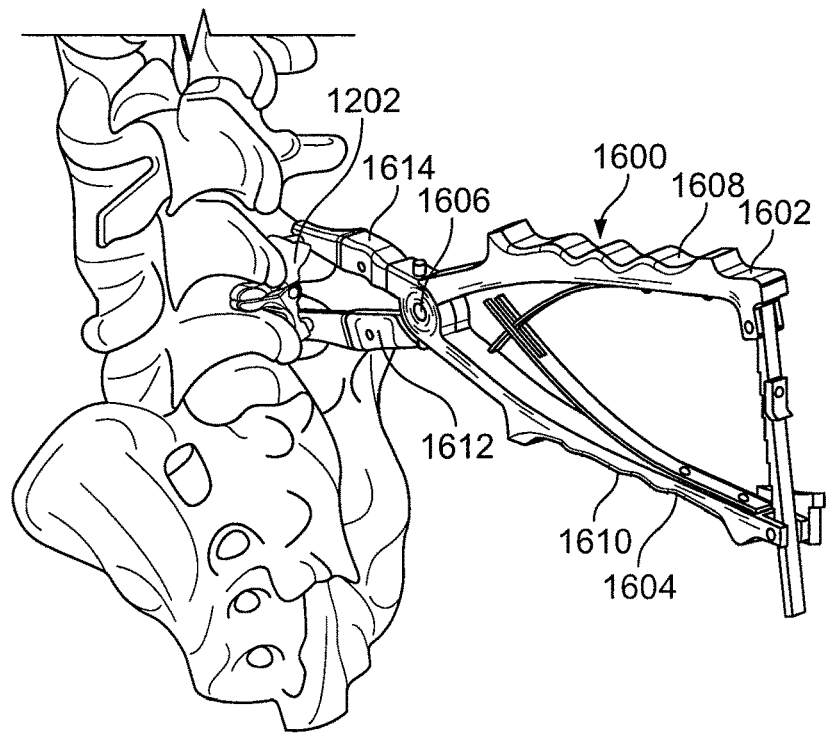
Figure 75:
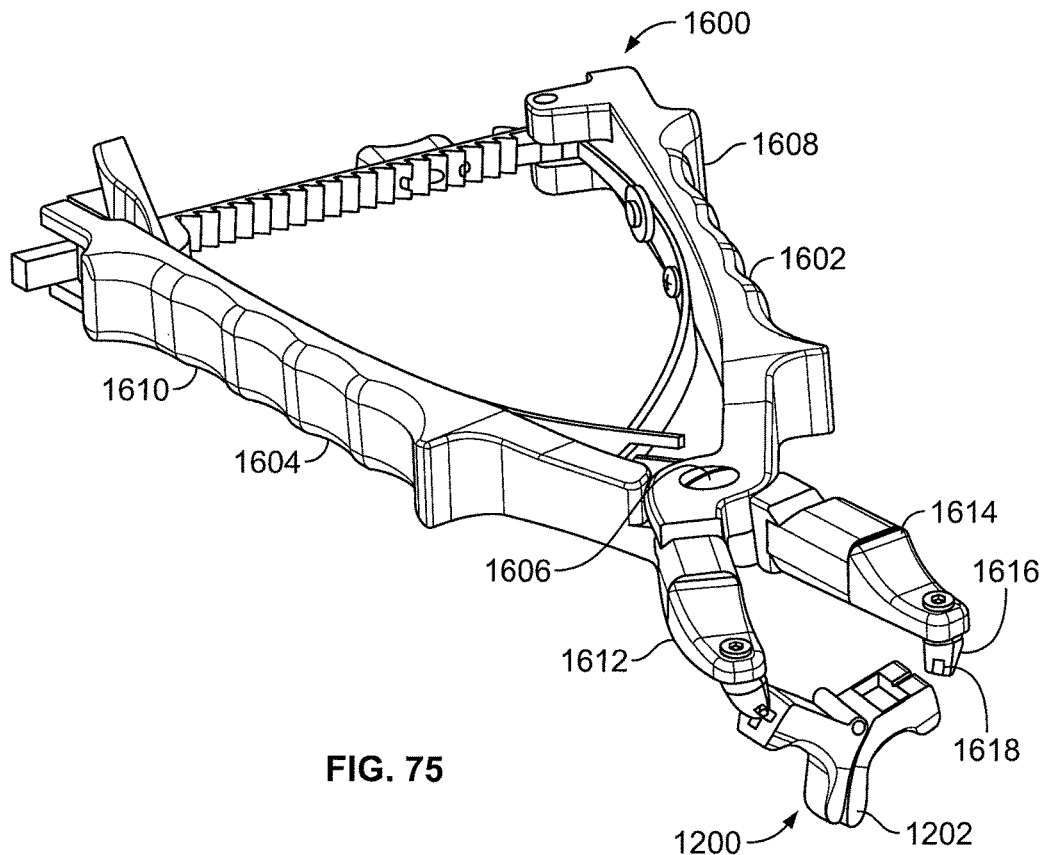
Figure 76:
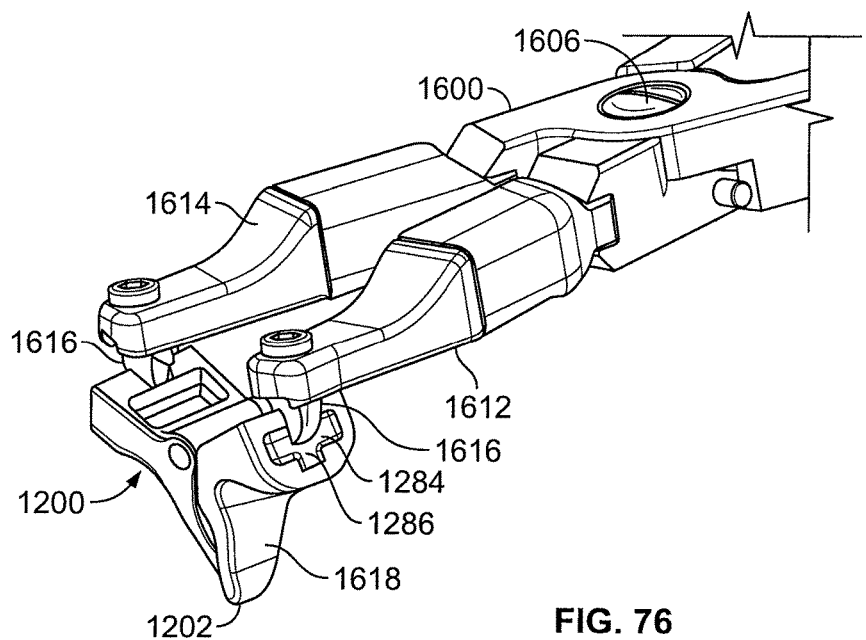
Figure 78:
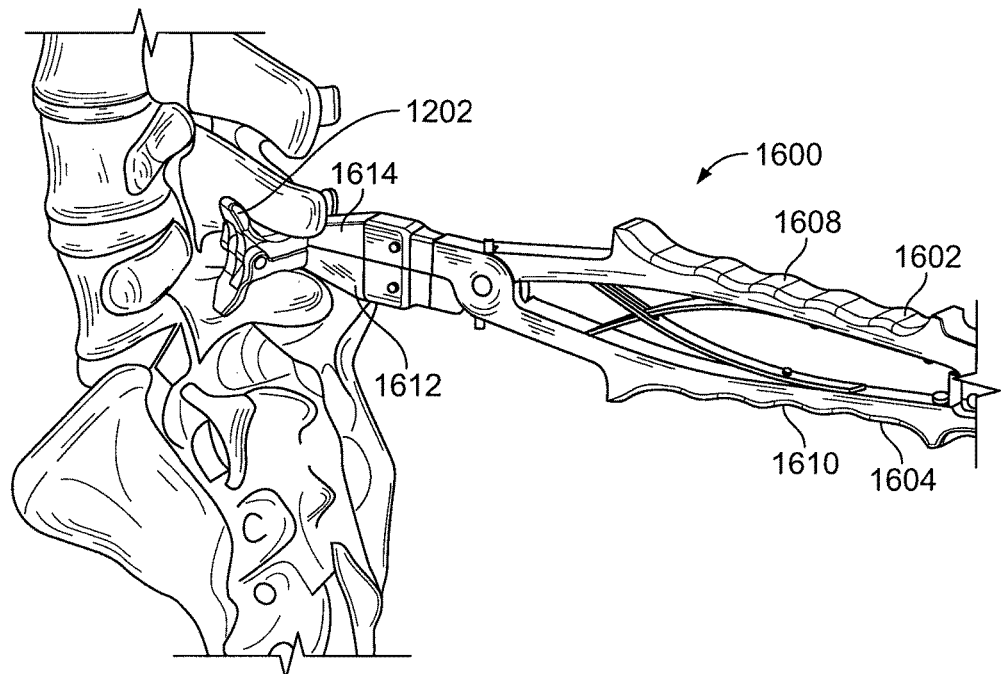
Figure 79:
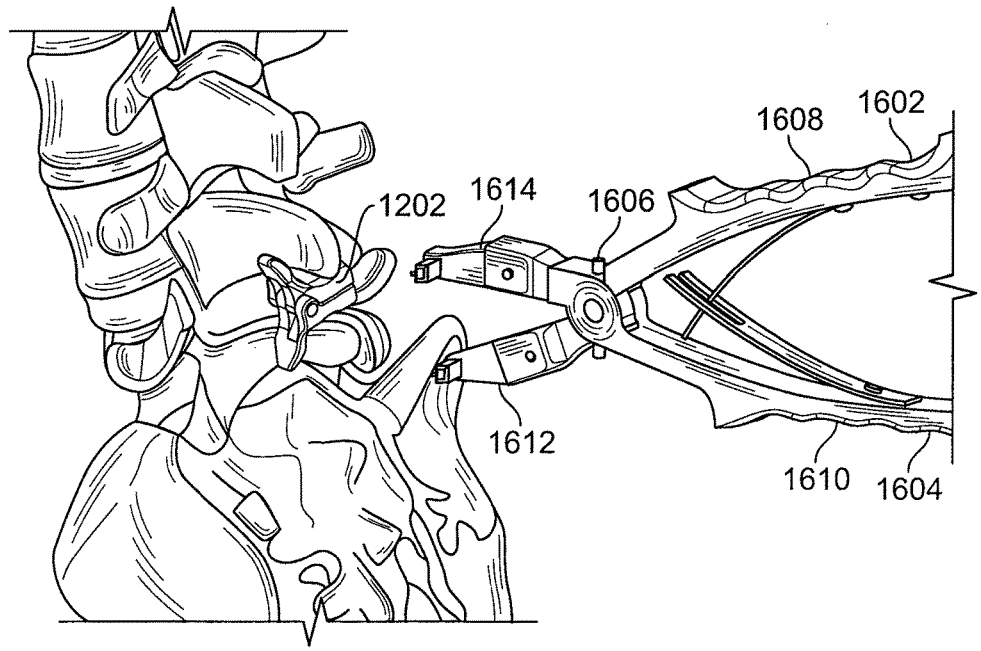

As illustrated in FIGS. 53 and 62, for example, the implant bodies described herein may include a tool engaging portion, for engaging a complementary portion of an insertion tool (insertion tool 1600 for example). Although applicable to any of the implant bodies described herein, the tool engaging portion 1280, as shown in FIG. 53, will be described with respect to the implant body 1202 for the sake of clarity. As shown in FIGS. 75-79, the insertion tool 1600 is preferably configured to engage the implant body 1202 arranged in the compact orientation (as shown in FIGS. 75 and 76), to insert the implant body 1202 between the spinous processes 12 (as shown in FIG. 77), and to pivot the implant body 1202 to the extended orientation (as shown in FIG. 78), with the vertebral engaging portions 1208, 1210 engaging the adjacent spinous processes 12.

With reference to FIG. 53, in one form, the engagement portion 1280 comprises an aperture 1282 defined in each of the first and second members 1204, 1206. Apertures 1282 may be formed, for example, on the outer surfaces of the third and fourth arms 1216, 1222 of the implant body 1202. As illustrated, each of apertures 1282 are generally cross-shaped with a horizontally-disposed slot 1284 and a vertically-disposed slot 1286. As shown, each of the vertically-disposed slots 1286 includes a first portion 1288 and a second portion 1290 in communication with the horizontally-disposed slot 1284.

Figure 68:
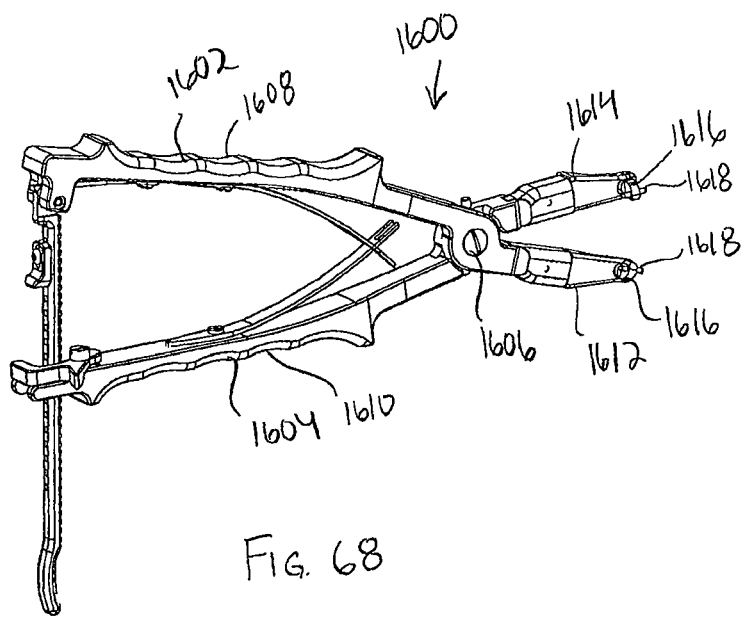
FIG. 68 is a perspective view of an insertion tool in accordance with another aspect of the invention.
Figure 69:
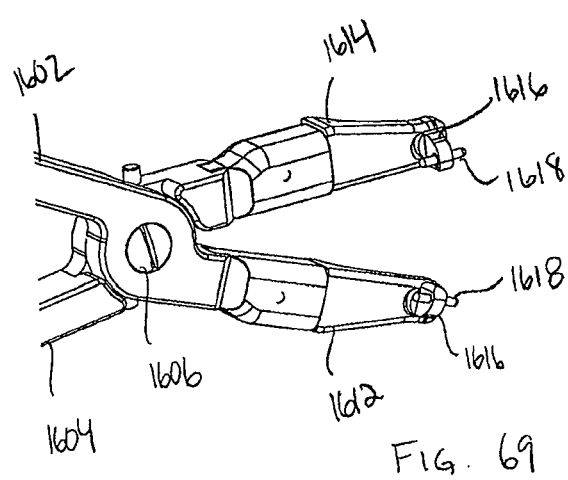
FIG. 69 is an enlarged perspective view of a portion on the insertion tool of FIG. 68.

As illustrated, the apertures 1282 are configured to receive a complementary portion of the insertion tool 1600. As shown in FIGS. 68 and 69, in one form, insertion tool 1600 is generally scissor-like with first and second lever arms 1602, 1604 connected at an adjustable connection 1606. The first and second lever arms 1602, 1604 include gripping portions 1608, 1610 and implant engaging portions 1612, 1614. As shown, the lever arms 1602, 1604 are configured such that squeezing the gripping portions 1608, 1610 towards one another causes the implant engaging portions 1612, 1614 to likewise move together.

Each of the implant engaging portions 1612, 1614 comprises an arm 1616, coupled with a pin 1618. Each arm 1616 and pin 1618 combination is configured to be received in an aperture 1282, with the pin 1618 received in the horizontally-disposed slot 1284 and the arm 1616 received in first portion 1288 of the vertically-disposed slot 1286. As shown in FIGS. 77 and 78, once the implant body 1202 is inserted between the spinous processes 12 of adjacent vertebrae 10, the gripping portions 1608, 1610 of the first and second arms 1602, 1604 can be squeezed together, causing the implant engaging portions 1612, 1614 to move together and the arms 1616 to be received in the second portions 1290 of the vertically-disposed slot 1286, thereby pivoting the implant body into the extended orientation.

Figure 70:
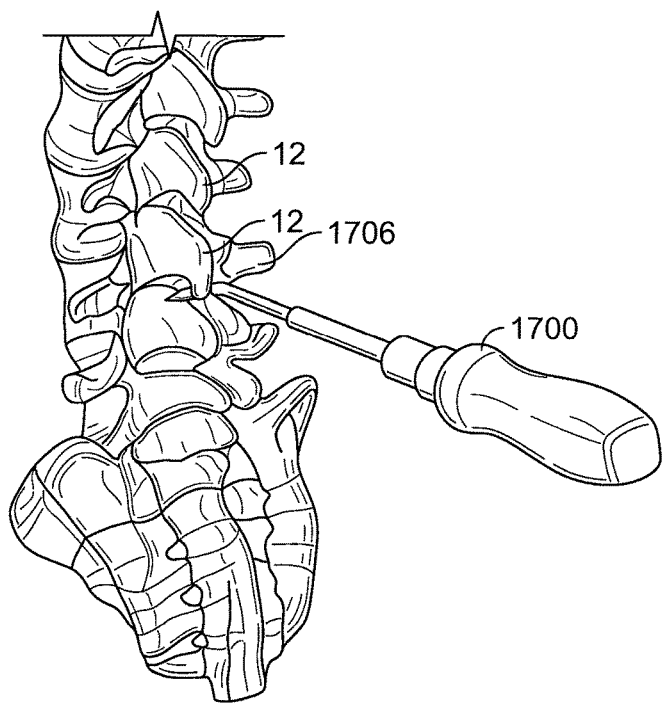
FIGS. 70-79 are perspective views of the steps of a method of insertion an implant device in accordance with another aspect of the invention.
Figure 71:
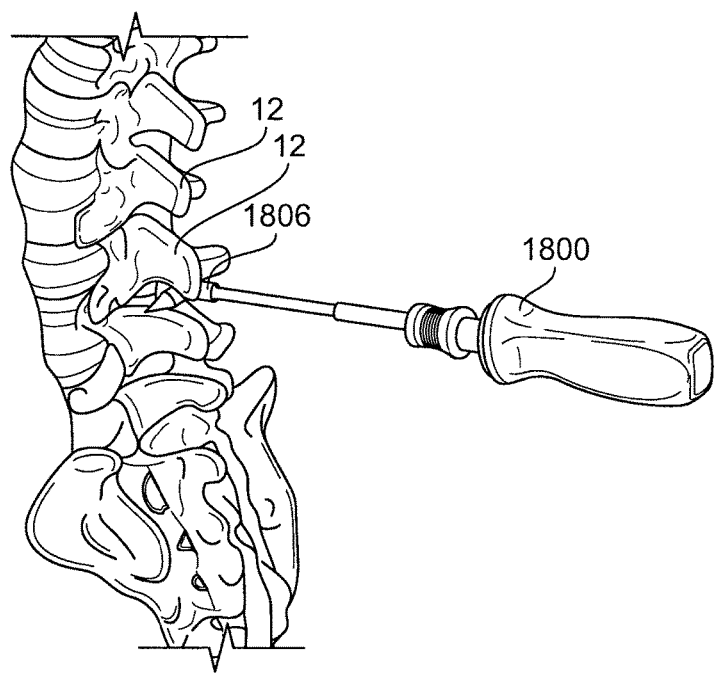
Figure 80:
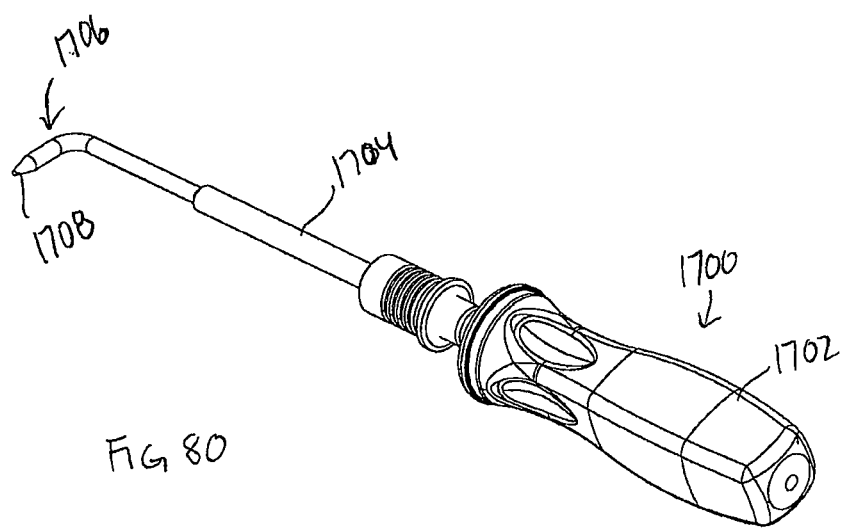
FIG. 80 is a perspective view of a tissue dilator in accordance with another aspect of the invention.
Figure 81:
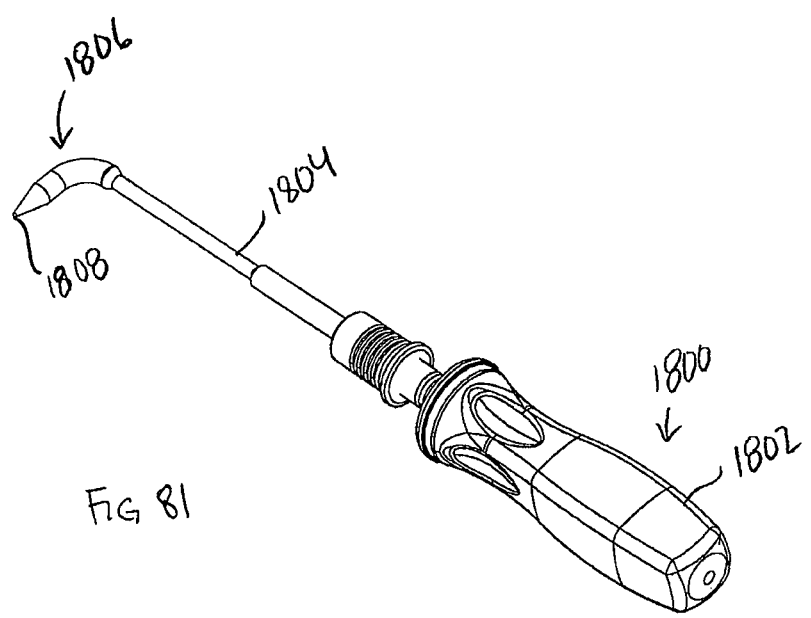
FIG. 81 is a perspective view of another tissue dilator in accordance with another aspect of the invention.

With reference to FIGS. 70-87, a method for insertion of any one of implant bodies 102, 1202, 1302, 1402, or 1502 between the spinous processes 12 is now described. As noted above, the implant bodies described herein are capable of being inserted through a minimally-invasive incision on one side of the spinous process 12. After making such an incision, a tissue dilator, such as tissue dilator 1700, is inserted through the incision and used to puncture and extend through the tissues between the spinous processes 12. As illustrated in FIG. 80, tissue dilator 1700 includes a handle 1702 and an elongate shaft 1704 having a dilator portion 1706 at the distal end. The dilator portion 1706 includes a tapered tip 1708 and is generally perpendicular to the elongate shaft 1704. So configured, the dilator portion may be easily inserted through the tissue between the spinous processes 12 (as shown in FIG. 70). Optionally, a second tissue dilator, such as tissue dilator 1800, may be inserted after removing the first tissue dilator 1700 (as shown in FIG. 71). As shown in FIG. 81, tissue dilator 1800 includes a larger-diameter dilator portion 1806 configured to further expand the opening formed in the tissues between the spinous processes 12.

Figure 72:
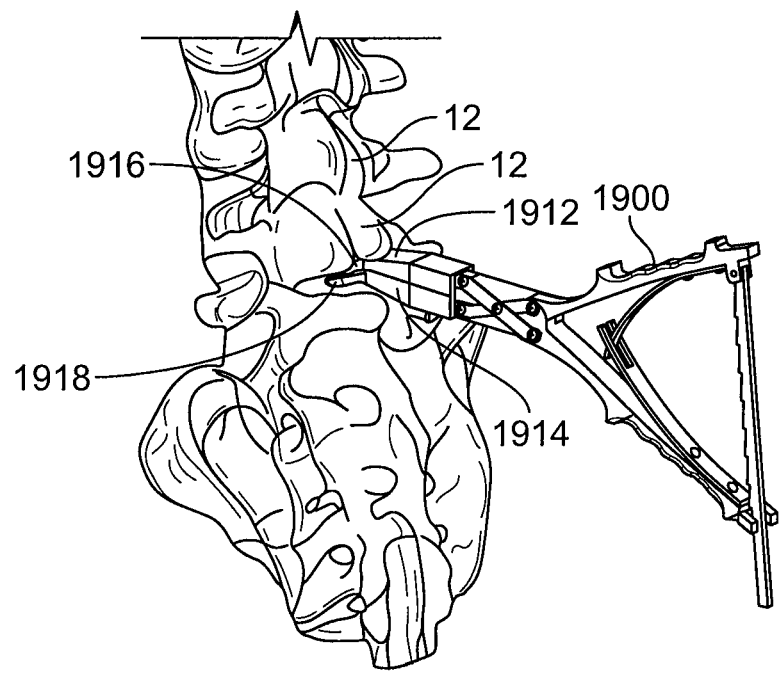
Figure 73:
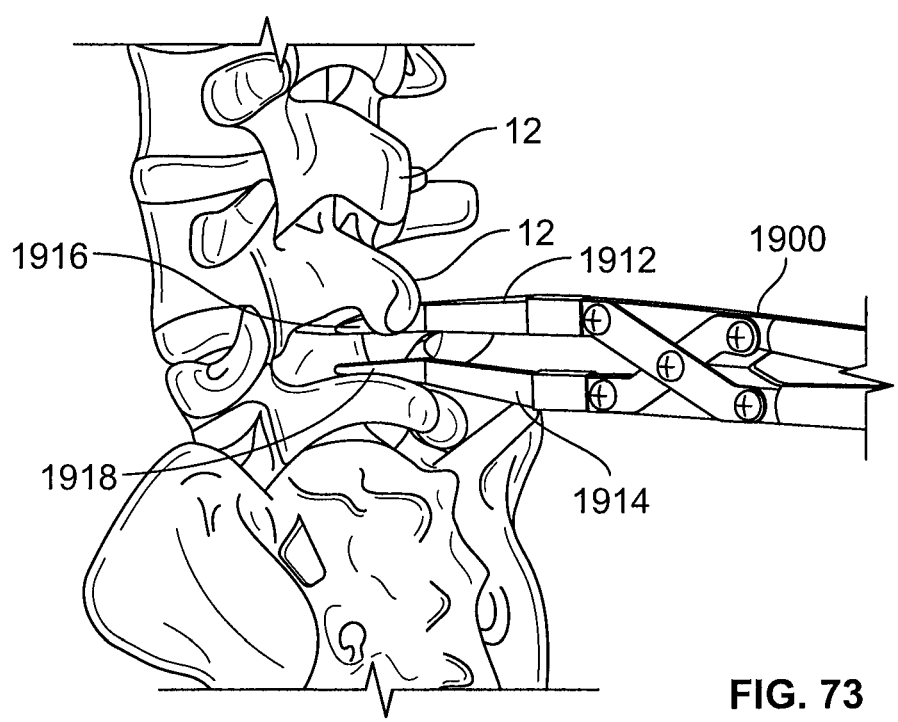

Next, as illustrated in FIGS. 72 and 73, a distractor tool, such as distractor tool 1900 for example, is inserted between spinous processes 12 and used to distract the adjacent vertebrae 10 apart to the desired distance. As shown, in FIGS. 82 and 83, distractor tool 1900 has first and second lever arms 1902, 1904 connected at an adjustable connection 1906. The first and second lever arms 1902, 1904 include gripping portions 1908, 1910 and distractor portions 1912, 1914. As shown, the lever arms 1902, 1904 are configured such that squeezing the gripping portions 1908, 1910 together causes the distractor portions 1912, 1914 to move apart.

Figure 82:
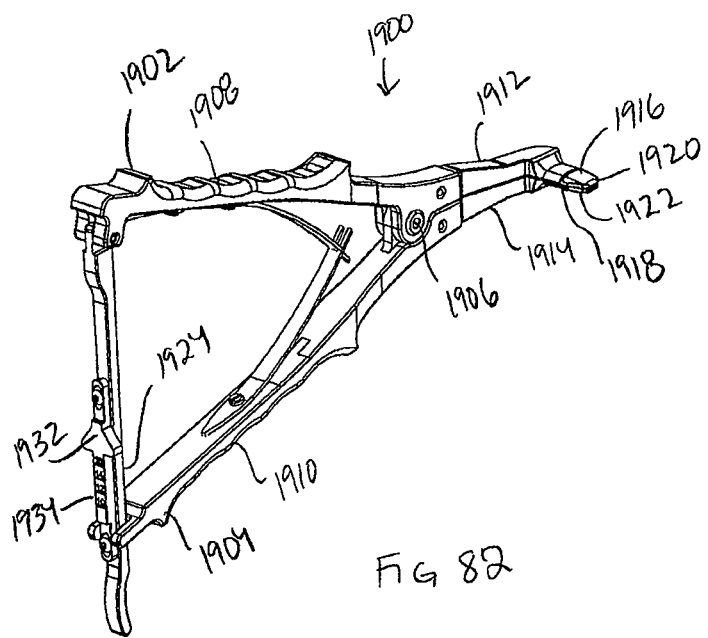
FIG. 82 is a perspective view of a distractor tool in accordance with another aspect of the invention.
Figure 83:
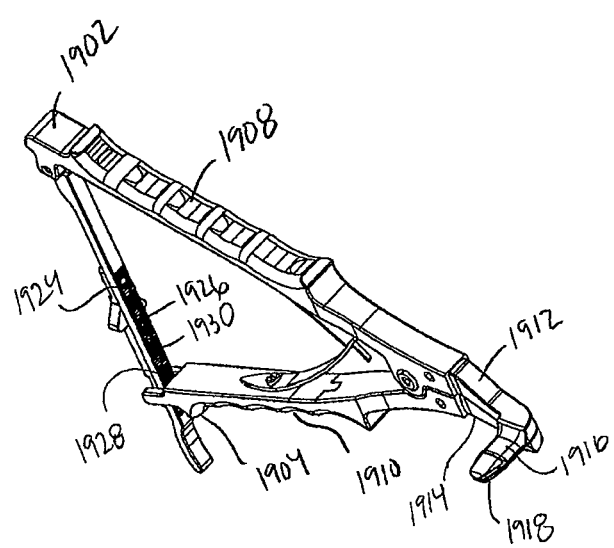
FIG. 83 is another perspective view of the distractor tool of FIG. 82.

Each of the distractor portions 1912, 1914 comprises a paddle 1916, 1918 projecting generally perpendicularly therefrom. As illustrated in FIG. 72, the paddles 1916, 1918 are inserted between the spinous processes 12 in a closed position, with the paddles 1916, 1918 in contact with each other. As shown in FIG. 73, the gripping portions 1908 and 1910 are then squeezed together to cause the distractor portions 1912, 1914 to separate, which causes the paddles 1916, 1918 to bear against the adjacent spinous processes 12 to move them apart to the desired spatial relationship. In a preferred embodiment, as illustrated in FIGS. 82 and 83, the paddles 1916, 1918 are configured to ease insertion through the opening in the interspinous tissues, and include tapered and/or rounded ends 1920, 1922.

A securing mechanism 1924 is optionally coupled to the gripping portions 1908, 1910 and secures the gripping portions 1908, 1910 in place. In one form, securing mechanism 1924 comprises a rack portion 1926 coupled to gripping portion 1908 and a pawl portion 1928 coupled to gripping portion 1910. The rack portion 1926 has a plurality of uni-directional teeth 1930 that engage the pawl portion 1928 such that the pawl portion 1928 is permitted to travel along the rack portion 1926 in one direction as the gripping portions 1908, 1910 are squeezed together, but is inhibited from moving back along the rack portion 1926 in the opposite direction when the gripping portions 1908, 1910 are released. In another form, the rack portion 1926 is pivotably coupled to gripping portion 1908 such that the rack portion 1926 can be pivoted away from gripping portion 1910 to disengage the pawl portion 1926 from the uni-directional teeth 1930 and thereby release gripping portions 1908, 1910. In yet another form, as shown in FIG. 82, the rack portion 1926 may include a size indicator 1932 including markings 1934 to indicated to distance that the distractor portions 1912, 1914 have been separated. The size indicator 1932 thereby advantageously allows for determination of an appropriately-size implant device.

Figure 74:
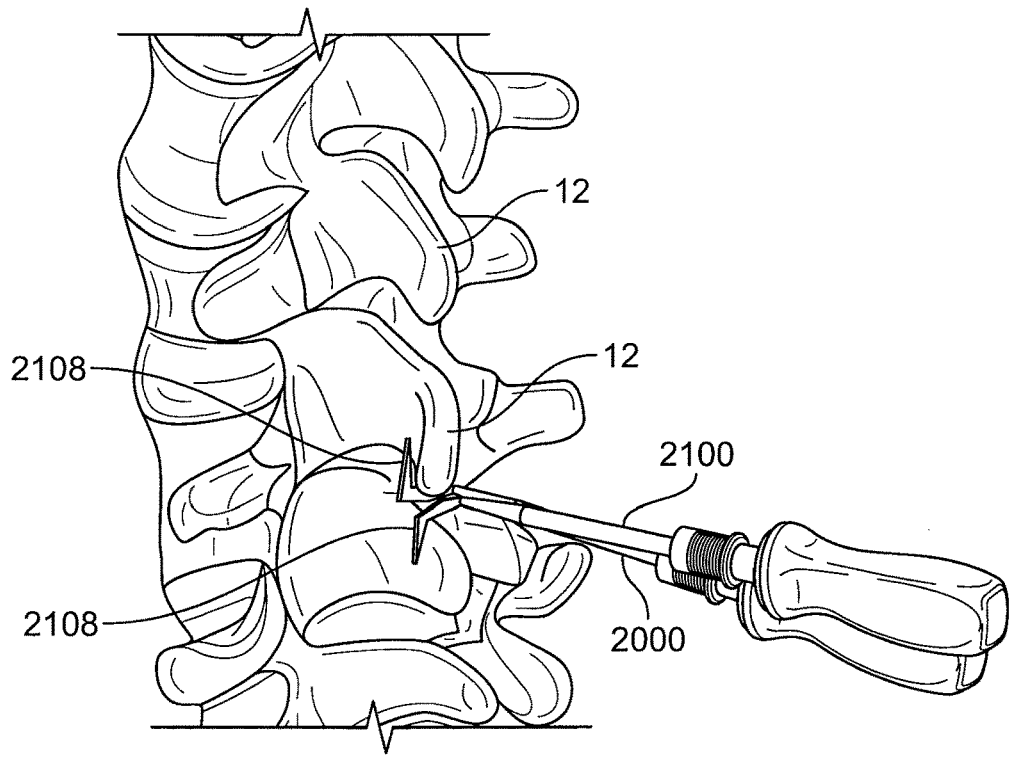
Figure 84:
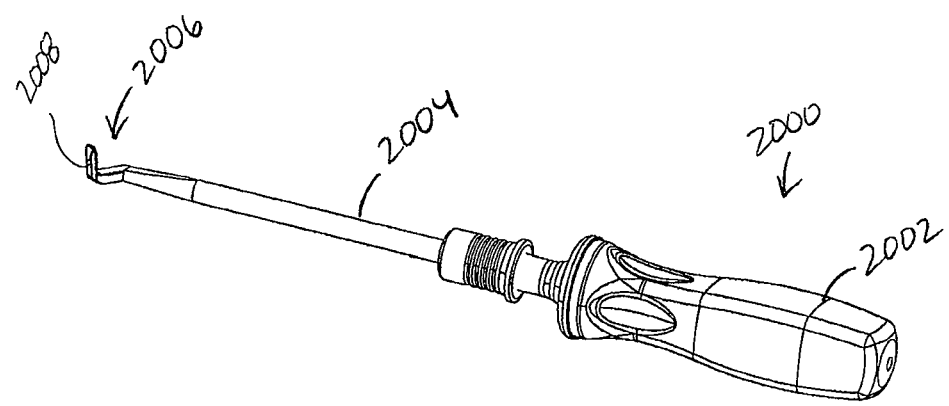
FIG. 84 is a perspective view of an upper tissue separator in accordance with another aspect of the invention.
Figure 85:
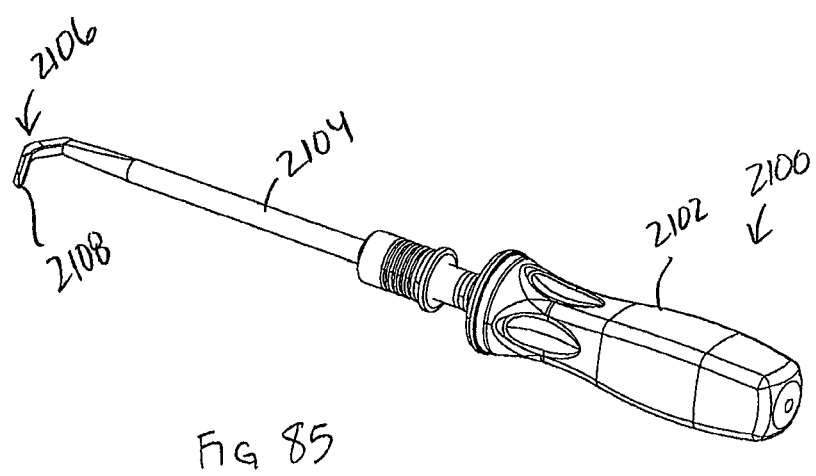
FIG. 85 is a perspective view of lower tissue separator in accordance with another aspect of the invention.

Once any necessary distraction is complete, a tissue separator is used to separate tissues from the contralateral side of the spinous processes 12. In one form, shown in FIG. 74, an upper tissue separator 2000 and a lower tissue separator 2100 are used to separate the tissues. As illustrated in FIG. 84, the upper tissue separator includes a handle 2002, an elongate shaft 2004, and a tissue separator portion 2006 at the distal end of the elongate shaft 2004. The tissue separator portion 2006 preferably comprises an L-shaped projection 2008 extending generally perpendicular to the elongate shaft 2004. As shown in FIG. 74, with the tissue separator portion 2006 inserted between the spinous processes 12, the L-shaped projection 2008 bends upward around the superior spinous process 12, and may be moved back and forth to separate the tissue on the contralateral side thereof. As shown in FIG. 85, the lower tissue separator 2100 likewise includes a handle 2102, an elongate shaft 2104, and a tissue separator portion 2106 at the distal end of the elongate shaft 2104. The tissue separator portion 2106 also preferably comprises an L-shaped projection 2108 extending generally perpendicular to the elongate shaft 2104. However, as illustrated in FIG. 74, the lower tissue separator 2100 is configured such that, with the tissue separator portion 2106 inserted between the spinous processes 12, the L-shaped projection 2108 bends downward around the inferior spinous process 12 and may, therefore, be moved back and forth to separate the tissue on the contralateral side thereof.

Figure 86:
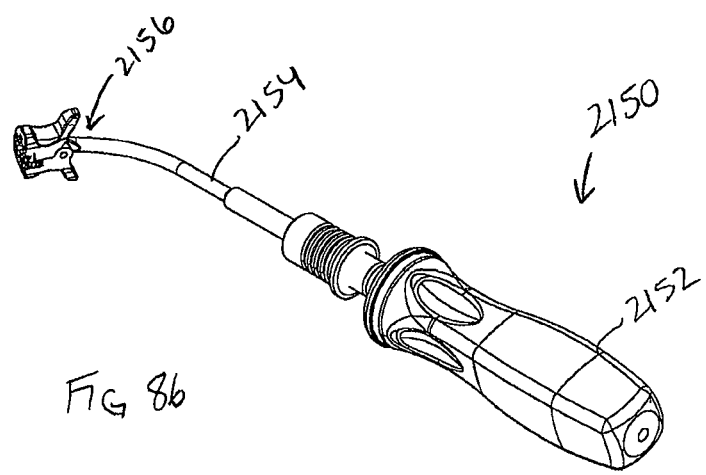
FIG. 86 is a perspective view of a removal probe in accordance with another aspect of the invention.
Figure 87:
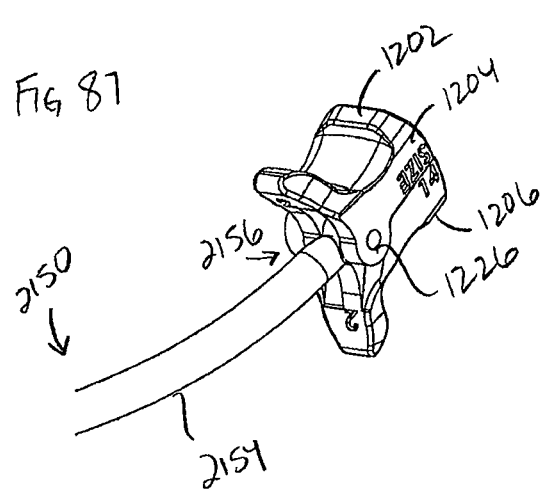
FIG. 87 is an enlarged perspective view of a portion of the removal probe of FIG. 86.

Finally, as illustrated in FIGS. 75-79, the implant body is coupled to the insertion tool 1600 and inserted between the spinous processes 12 as described above. If necessary, a removal probe, such as removal probe 2150, may be used to remove the implant body from its implanted position between the spinous processes 12. As illustrated in FIGS. 86 and 87, removal probe 2150 includes a handle 2152, an elongate shaft 2154, and a probe portion 2156 at the distal end of the elongate shaft 2154. The probe portion 2156 is configured to couple with the implant body at the adjustable connection between the first and second members. Thus, in one form, the removal probe 2150 may be inserted through an incision to the opposite side of the spinous process 12 from which the implant body was inserted, coupled with the implant body at the adjustable connection between the first and second members, and used to push the implant body from between the spinous processes 12. The implant body will pivot back toward the compact orientation as it pushed back to aid in the removal.

Figure 88:
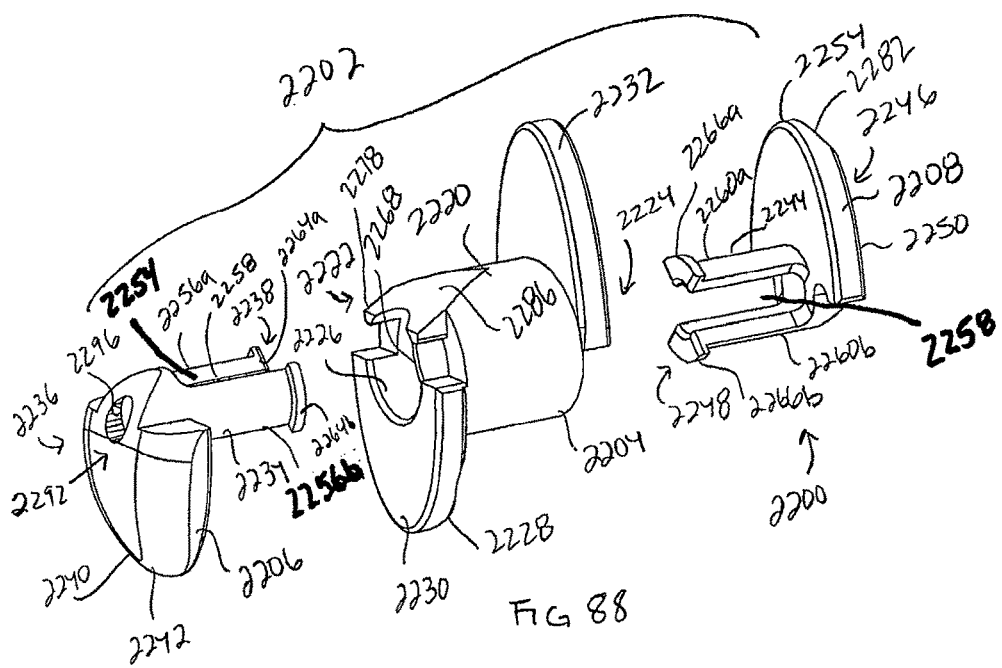
FIG. 88 is an exploded view of an implant device in accordance with another aspect of the invention.
Figure 89:
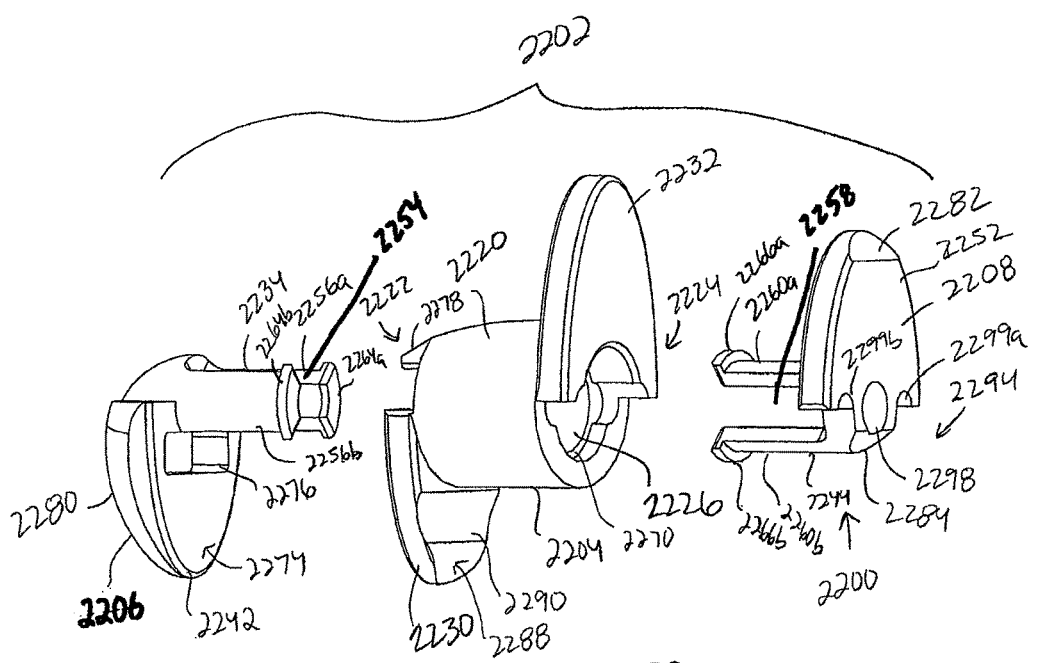
FIG. 89 is another exploded view of the implant device of FIG. 88.
Figure 90:
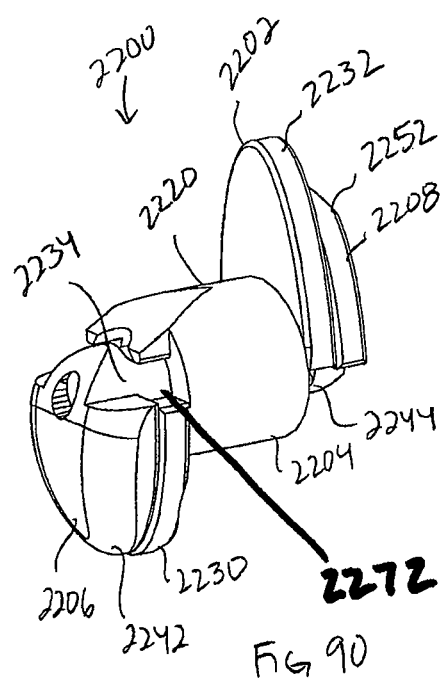
FIG. 90 is a perspective view of the implant device of FIG. 88 with the implant device shown in a compact orientation.
Figure 91:
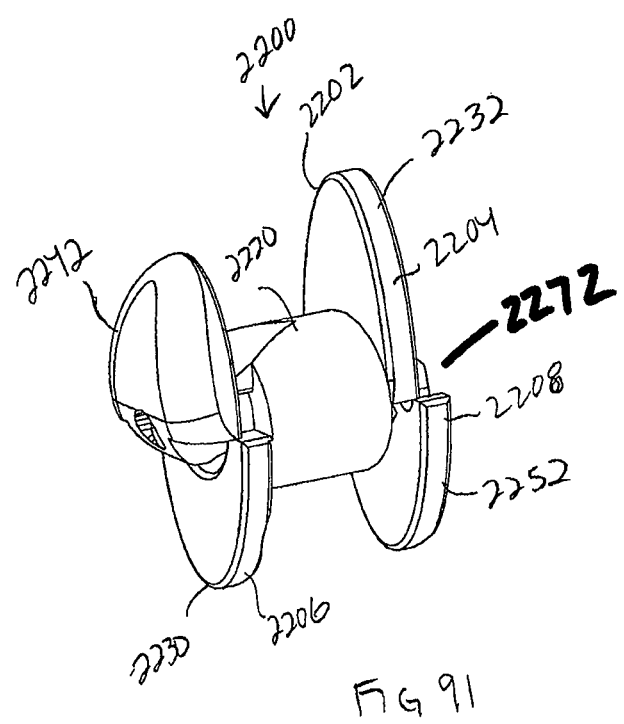
FIG. 91 is a perspective view of the implant device of FIG. 88 with the first and second members shifted toward an extended orientation but not retracted.
Figure 92:
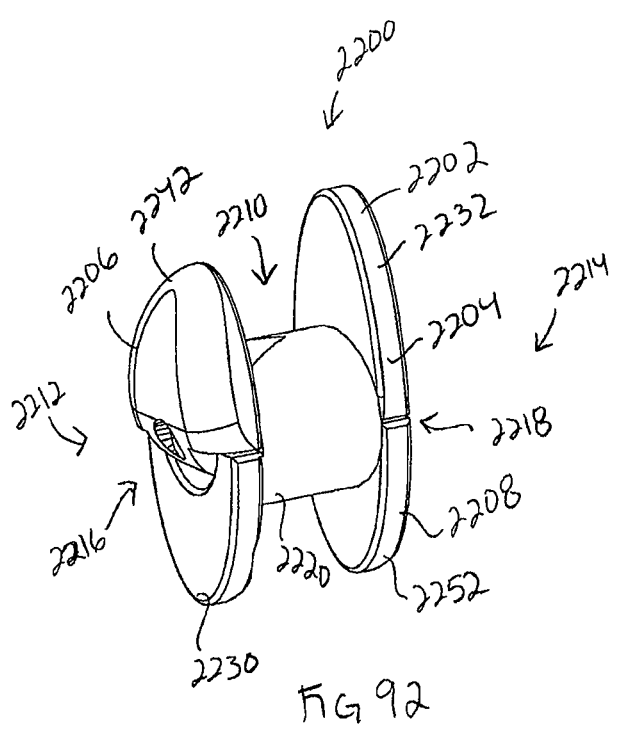
FIG. 92 is a perspective view of the implant device of FIG. 88 with the implant device shown in an extended orientation.
Figure 93:
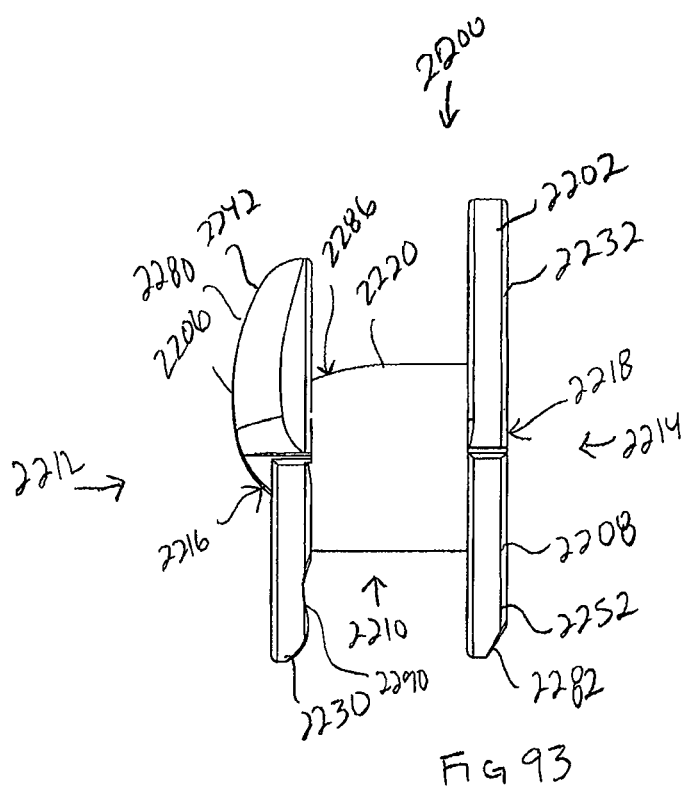
FIG. 93 is a side elevation view of the implant device of FIG. 88 with the implant device shown in an extended orientation.

With reference to FIGS. 88-95, an implant device 2200 is shown in accordance with another aspect of the invention. Implant device 2200 includes an implant body 2202 including a number of the features of implant body 1102 described above. Accordingly, only the differences will be set forth in detail herein. The implant body 2202 includes a first member 2204, a second member 2206 and a third member 2208 adjustably interconnected such that the implant body 2202 can be arranged in a compact orientation (as shown in FIG. 90, for example) for being inserted between the spinous processes 12, and an extended orientation (as shown in FIGS. 92-95), for resisting expulsion of the implant body 2202 therefrom. As illustrated in FIG. 92, for example, in the extended orientation, the implant body 2202 has a generally spool-shaped configuration with a generally cylindrical portion 2210 having a first end 2212, a second end 2214, and first and second generally annular flanges 2216, 2218 at the first and second ends 2212, 2214.

As shown in FIGS. 88 and 89, for example, in one form, the first member 2204 includes a generally cylindrical spacer portion 2220 with a first end 2222 and a second end 2224 and a longitudinal throughbore 2226 extending therebetween. The spacer portion 2220 includes a first retention member 2228 configured to resist expulsion of the implant body 2202 from between the spinous processes 12. In the illustrated form, a first semiannular flange 2230 is provided at the first end 2222 of the spacer portion 2220 and a second semiannular flange 2232 is provided at the second end 2224.

As shown, the second member 2206 preferably includes another generally cylindrical portion 2234 having a first end 2236 and a second end 2238. The cylindrical portion 2234 is configured to be slideably received in the longitudinal throughbore 2226 of the first member 2204. A second retention member 2240, such as a third semiannular flange 2242, is provided at the first end 2236 of the cylindrical portion 2234. Similarly, the third member 2208 preferably includes another generally cylindrical portion 2244 having a first end 2246 and a second end 2248. The cylindrical portion 2244 is configured to be slideably received in the longitudinal throughbore 2226 of the first member 2204. A third retention member 2250, such as a fourth semiannular flange 2252, is provided at the first end 2246 of the cylindrical portion 2244.

As illustrated in FIGS. 90-92, the cylindrical portions 2234, 2244 are rotatable within the longitudinal throughbore 2226 to reconfigure the implant body 2202 between the compact orientation and the extended orientation. More specifically, the implant body 2202 can be arranged in the compact orientation (as shown in FIG. 90, for example), in which the cylindrical portions 2234, 2244 are partially received in the longitudinal throughbore 2226 of the spacer portion 2220 and the third and fourth semiannular flanges 2242, 2252 are arranged in overlapping orientation with the first and second semiannular flanges 2230, 2232 respectively. To orient the implant body 2202 in the extended orientation (as shown in FIGS. 92-95), the cylindrical portions 2234, 2244 can be rotated approximately 180° (as illustrated in FIG. 91) and retracted further into the first member 2204, in which the first and third semiannular flanges 2230, 2232 and the second and fourth semiannular flanges 2234, 2244 align to form substantially flush, annular flanges 2216, 2218.

As illustrated in FIGS. 88 and 89, in one form, the cylindrical portion 2234 includes a slot 2254 at the second end 2238 defining a first pair of deflectable arms 2256*a,b*. Likewise, the cylindrical portion 2244 includes a slot 2258 at the second end 2248 defining a second pair of deflectable arms 2260*a,b*. As illustrated, the deflectable arms 2256*a,b* and arms 2260*a,b* are arranged in an alternating configuration. Thus, as one of the cylindrical portions 2234, 2244 is rotated toward the extended orientation, the other of the cylindrical portions 2234, 2244 is caused to rotate as well.

According to yet another aspect, the implant body 2202 includes a first securing mechanism 2262 configured to secure the implant body 2202 in the extended orientation. In one form, each of the arms 2256*a,b* and arms 2260*a,b* preferably has a ridge 2264*a,b*, 2266*a,b* at the second end 2238, 2248 configured to mate with interior grooves 2268, 2270 at first and second ends 2222, 2224 of the spacer portion 2220 with the arms 2256*a,b* and 2260*a,b* received in the longitudinal throughbore 2226. In the compact orientation, with the third and fourth semiannular flanges 2242, 2252 arranged in an overlapping orientation with the first and second semiannular flanges 2230, 2232 and the cylindrical portions 2234, 2244 only partially received in the longitudinal throughbore 2226, the ridges 2264*a,b* and 2266*a,b* are disengaged from the interior grooves 2268 and 2270. In the extended orientation (as shown in FIG. 94, for example), the cylindrical portions 2234, 2244 are rotated approximately 180° and retracted further into the longitudinal throughbore 2226 such that the ridges 2264*a,b* snap into the interior groove 2270 and the ridges 2266*a,b* snap into the interior groove 2268 to secure the implant body 2202 in the orientation.

Figure 94:
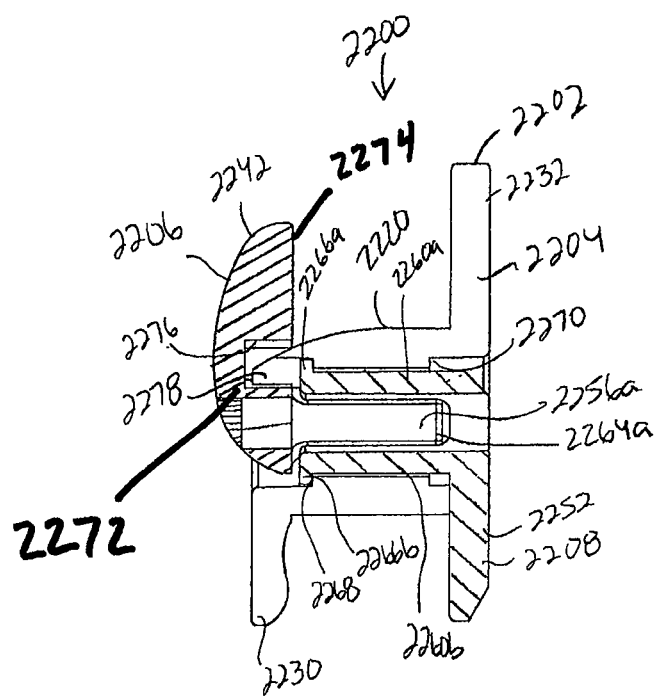
FIG. 94 is a cross-section of the implant device of FIG. 88 with the implant device shown in an extended orientation.
Figure 95:
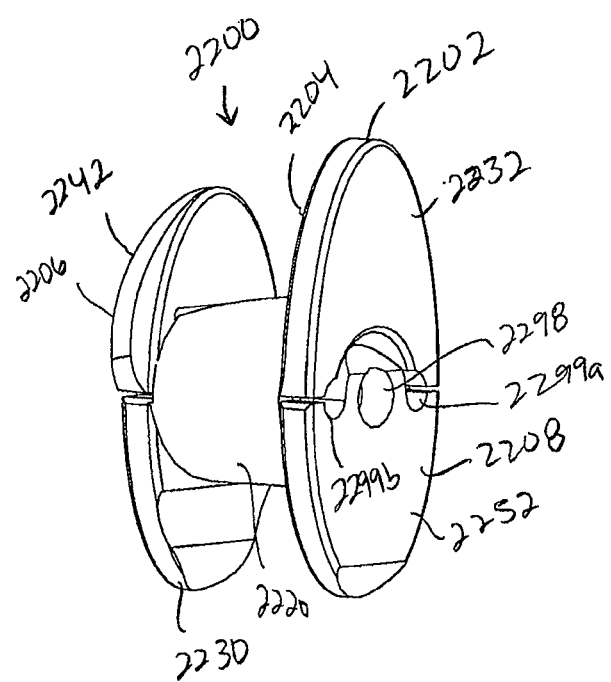
FIG. 95 is another perspective view of the implant device of FIG. 88 with the implant device shown in an extended orientation.
Figure 96:
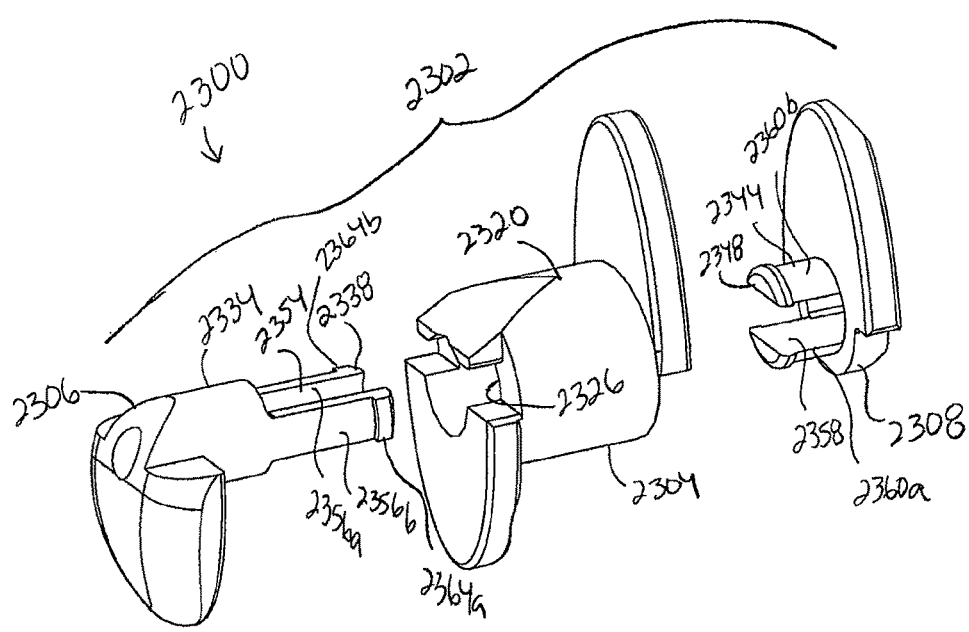
FIG. 96 is an exploded view of an implant device in accordance with another aspect of the invention.

Additionally, as shown in FIG. 94, the implant body 2202 includes a second securing mechanism 2272 configured to inhibit rotation of the cylindrical portions 2234, 2244 within the longitudinal throughbore 2226 once the implant body 2202 is secured in the extended orientation. As illustrated, the third semiannular flange 2242 has a first surface 2274 generally facing the first end 2222 of the spacer portion 2220 with an aperture 2276 defined therein. When the cylindrical portion 2234 is rotated toward the extended orientation, the aperture 2276 aligns with a projection 2278 extending from the first end 2222 of the spacer portion 2220, and when the cylindrical portion 2234 is retracted further into the longitudinal throughbore 2226 such that the ridges 2256*a,b* snap into the interior groove 2270, the projection 2278 is received in the aperture 2276, thereby inhibiting rotation of the cylindrical portions 2234, 2244 (as shown in FIG. 94, for example).

The implant body 2202 is configured to be inserted between adjacent spinous processes 12 in the compact orientation and then adjusted to the extended orientation. Thus, the implant body 2202 may be inserted through a minimally invasive procedure requiring only a single incision on one side of the spine, preferably through a small aperture formed in the interspinous ligament (not shown). Thus, the implant body 2202 has a number of features configured to assist insertion of the implant body 2202 through an aperture in the interspinous ligament and rotation of the implant body 2202 into the extended orientation. As illustrated in FIGS. 88-90 for example, the semiannular flange 2242 of the second member 2206 has a second surface 2280 having a generally rounded and/or tapered configuration to ease insertion of the flange 2242 through an aperture in the ligament and rotation of the second member 2206 towards the extended configuration. The third member 2208 has canted portions 2282, 2284 (shown in FIG. 89, for example) to assist rotation. The first member 2204 also has a canted portion 2286 that aids insertion. Additionally, the first semiannular flange 2216 has a first surface 2288 having a concave portion 2290 that assists proper positioning of the implant body 2202 between the spinous processes 12 and retaining the implant body 2202 in position once inserted therebetween. Once the semiannular flanges 2230, 2242 are inserted through an aperture in the interspinous ligament, the concave portion 2290 acts to catch the interspinous ligament on the other side, thereby retaining the implant body 2202 between the spinous processes 12 and reducing the potential for undesirable back-out.

As shown in FIGS. 88 and 89, in accordance with another aspect, the second and third members 2206, 2208 include tool engagement portions 2292, 2294 configured to engage a tool (not shown) for rotating and retracting the second and third members 2206, 2208 relative to the first member 2204. Any suitable engagement arrangement may be used. As illustrated, in one form, the second and third members 2206, 2208 include throughbores 2296, 2298 that align to receive a rod (not shown) for providing a rotating force. The third member 2208 may additionally have access apertures 2299*a,b* defined therein. Access apertures 2299*a,b* are configured to provide access to a complementary portion of a tool (not shown) into the longitudinal throughbore 2226 and to release the ridges 2264a,b of arms 2256a,b from the interior groove 2270 to disassemble the implant body 2202 if so desired.

With reference to FIGS. 96-103, an implant device 2300 is shown in accordance with another aspect of the invention. Implant device 2300 includes an implant body 2302 including the features of implant body 2202 described above. Accordingly, only the differences will be set forth in detail herein. In particular, the implant body 2302 has an alternative configuration for securing the implant body 2302 in the extended orientation and inhibiting rotation toward the compact orientation.

Figure 98:
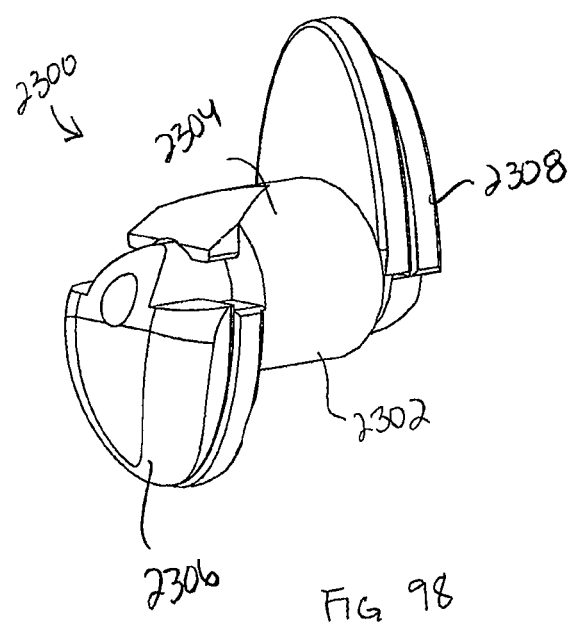
FIG. 98 is a perspective view of the implant device of FIG. 96 with the implant device shown in a compact orientation.
Figure 99:
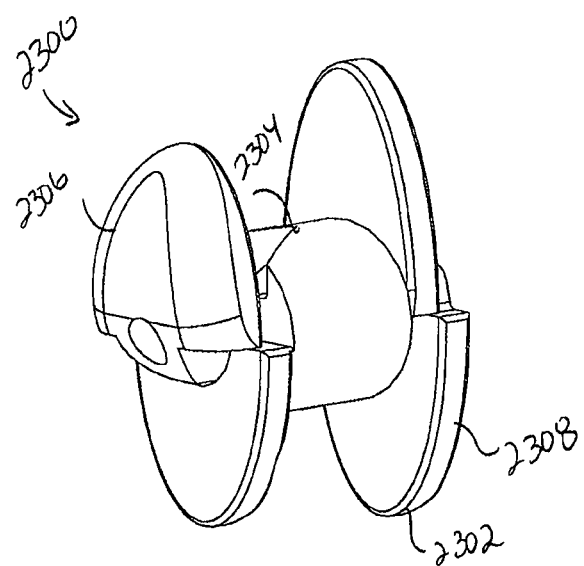
FIG. 99 is a perspective view of the implant device of FIG. 96 with the implant device shown in a rotated orientation.
Figure 100:
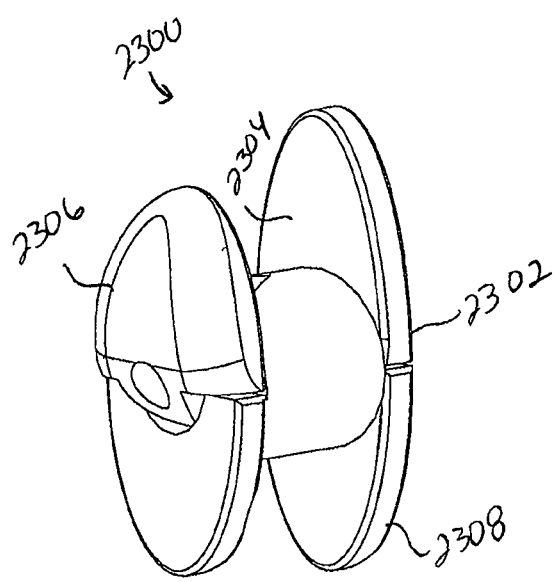
FIG. 100 is a perspective view of the implant device of FIG. 96 with the implant device shown in an extended orientation.
Figure 101:
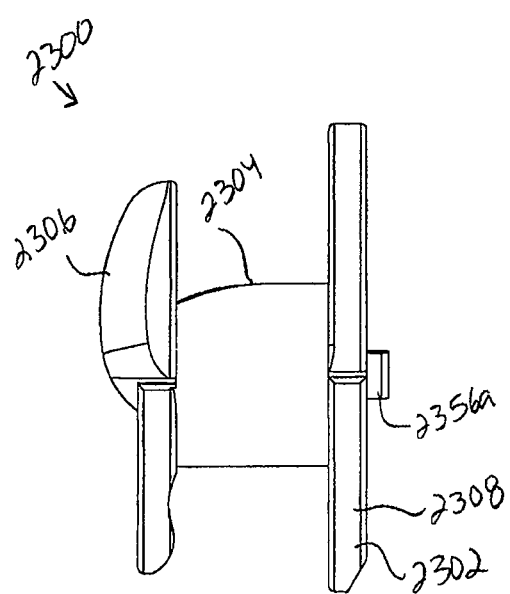
FIG. 101 is a side elevation view of the implant device of FIG. 96 with the implant device shown in an extended orientation.
Figure 102:
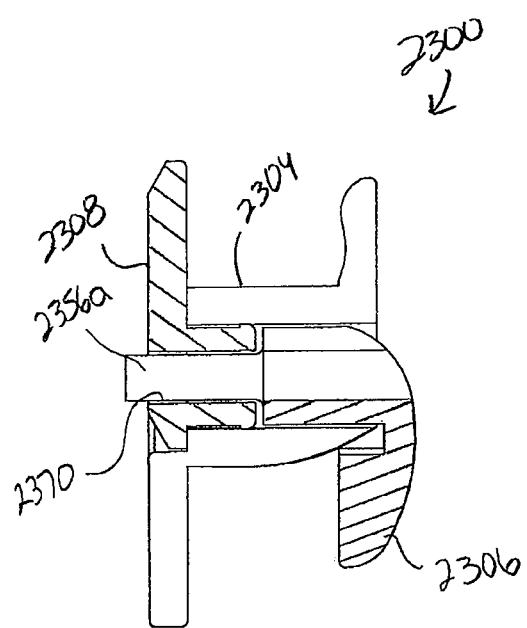
FIG. 102 is a cross-section of the implant device of FIG. 96 with the implant device shown in an extended orientation.

As in the implant body 2202, the implant body 2302 includes a first member 2304, a second member 2306 and a third member 2308 adjustably interconnected such that the implant body 2302 can be arranged in a compact orientation (as shown in FIG. 98, for example) and an extended orientation (as shown in FIGS. 100-103, for example). The first member 2304 includes a generally cylindrical spacer portion 2320 with a longitudinal throughbore 2326 extending therethrough. The second and third members 2306, 2308 include generally cylindrical portions 2334, 2344 that are rotatable within the longitudinal throughbore 2326 to move the implant body 2302 between the compact and extended orientations. The generally cylindrical portion 2334 has an end 2338 having a slot 2354 therein defining a pair of deflectable arms 2356a,b. Likewise, the cylindrical portion 2344 includes a slot 2358 at an end 2348 defining a second pair of deflectable arms 2360a,b. As illustrated, the deflectable arms 2356a,b and arms 2360a,b are arranged in an alternating configuration. Thus, as one of the cylindrical portions 2334, 2344 is rotated toward the extended orientation, the other of the cylindrical portions is caused to rotate as well.

Figure 97:
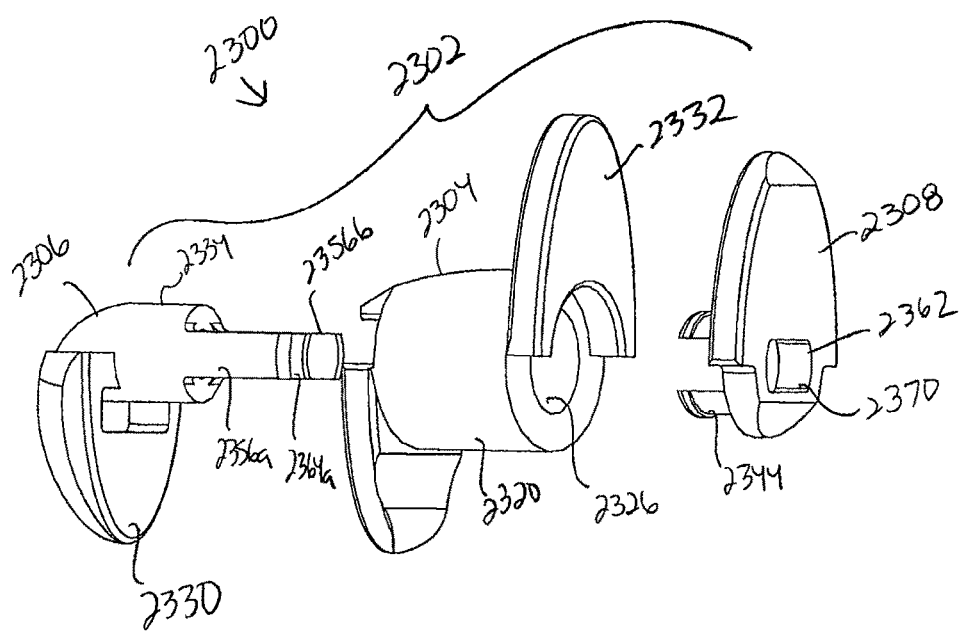
FIG. 97 is another exploded view of the implant device of FIG. 96.
Figure 103:
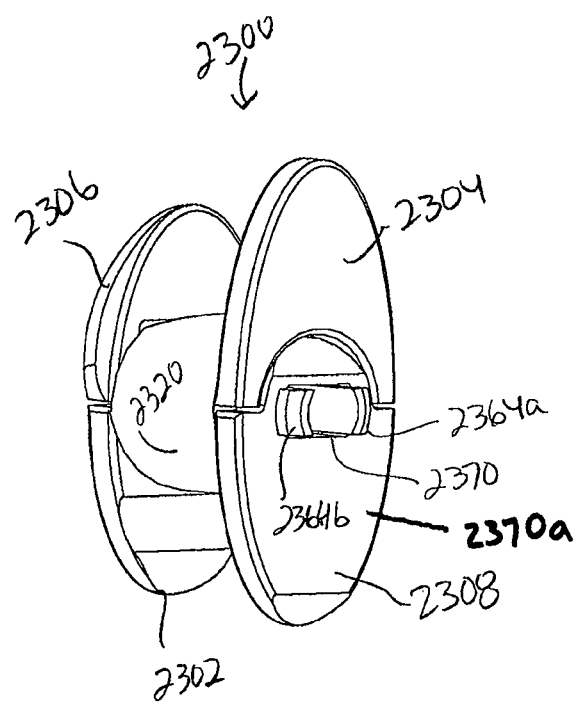
FIG. 103 is another perspective view of the implant device of FIG. 96 with the implant device shown in an extended orientation.

For securing the implant body 2302, rather than having ridges at the ends of arms 2356a,b and 2360a,b to mate with an interior groove of the spacer portion 2320, the second member 2306 and the third member 2308 are preferably configured to mate to one another in the extended orientation. As illustrated in FIGS. 97 and 103, for example, the third member 2308 preferably has an aperture 2370 configured to receive arms 2356a,b of the second member 2306. Arms 2356a,b, which include ridges 236a4a,b at the distal end, may be squeezed together for insertion through aperture 2370. The ridges 2364a,b are configured such that once the ridges 2364a,b clear the aperture 2370, the ridges 2364a,b will engage the outer surface 2370a of the third member 2308 thereby securing the second and third members 2306, 2308 together and preventing the second and third members 2306, 2308 from rotating independently from one another. Accordingly, arms 2356a, b may be simply squeezed together to release the ridges 2364a,b from the outside of the aperture 2370 to disassemble the implant body 2302.

With reference to FIGS. 104-110, an implant device 2400 is shown in accordance with another aspect of the invention. Implant device 2400 includes an implant body 2402 including the features of implant bodies 2202 and 2302 described above. Accordingly, only the differences will be set forth in detail herein.

Figure 106:
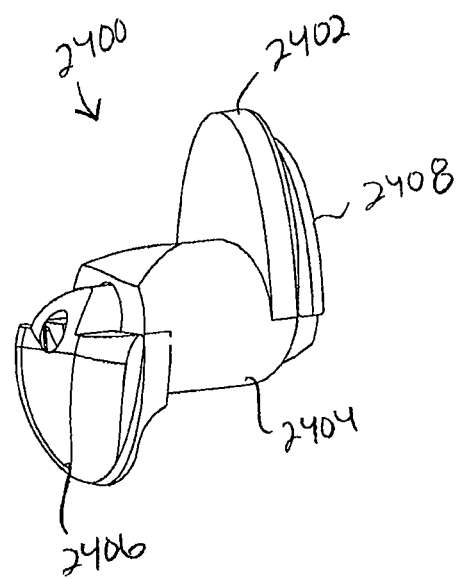
FIG. 106 is a perspective view of the implant device of FIG. 104 with the implant device shown in a compact orientation.
Figure 107:
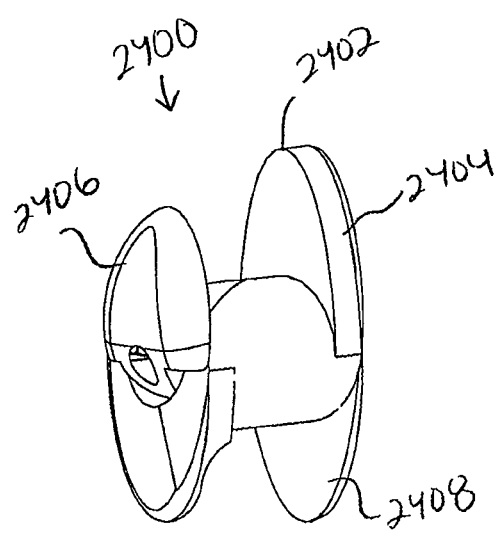
FIG. 107 is a perspective view of the implant device of FIG. 104 with the implant device shown in an extended orientation.
Figure 108:
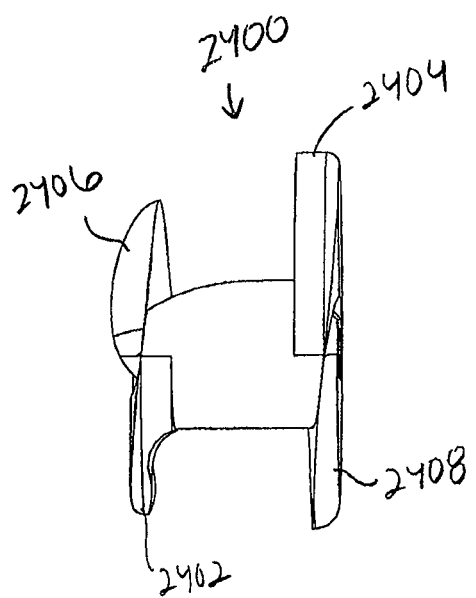
FIG. 108 is a side elevation view of the implant device of FIG. 104 with the implant device shown in an extended orientation.
Figure 109:
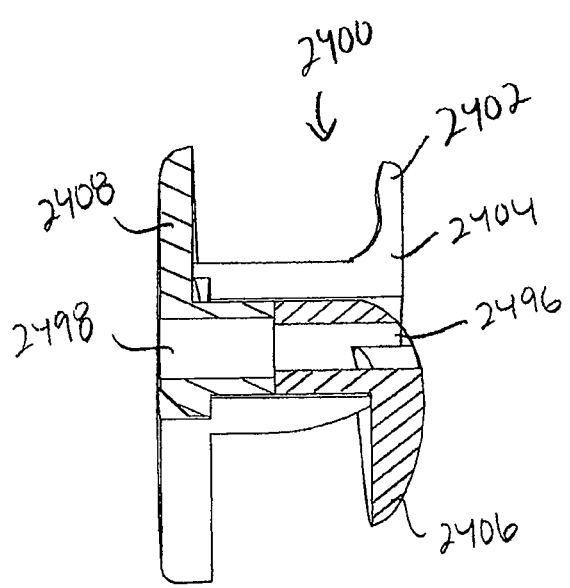
FIG. 109 is a cross-section of the implant device of FIG. 104 with the implant device shown in an extended orientation.
Figure 110:
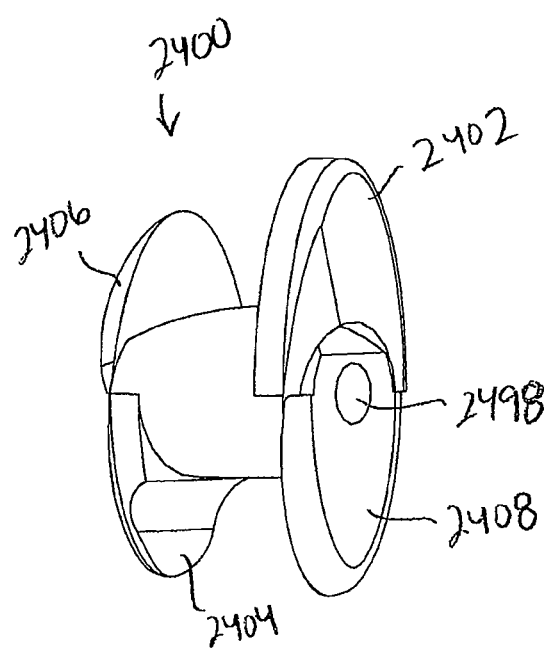
FIG. 110 is another perspective view of the implant device of FIG. 104 with the implant device shown in an extended orientation.

The implant body 2402 includes a first member 2404, a second member 2406 and a third member 2408 adjustably interconnected such that the implant body 2402 can be arranged in a compact orientation (as shown in FIG. 106, for example) and an extended orientation (as shown in FIGS. 107-110, for example). The first member 2404 includes a generally cylindrical spacer portion 2420 with a first end 2422, a second end 2424, and a longitudinal throughbore 2426 extending therethrough. The second and third members 2406, 2408 include generally cylindrical portions 2434, 2444 that are rotatable within the longitudinal bore 2426 to move the implant body 2402 between the compact and extended orientations. However, unlike the alternating arms configuration of implant bodies 2202 and 2302, which cause the second and third members to rotate together in the same direction, implant body 2402 is configured such that cylindrical portions 2434 and 2444 rotate independently of one another in opposite directions. This configuration advantageously permits both cylindrical portions 2434, 2444 (and their associated semiannular flanges 2442, 2452) to be rotated in a generally posterior direction (i.e., away from the patient's spinal column) so as to avoid any undesirable contact between the implant and the patient's vertebrae (in particular, the transverse processes).

Figure 104:
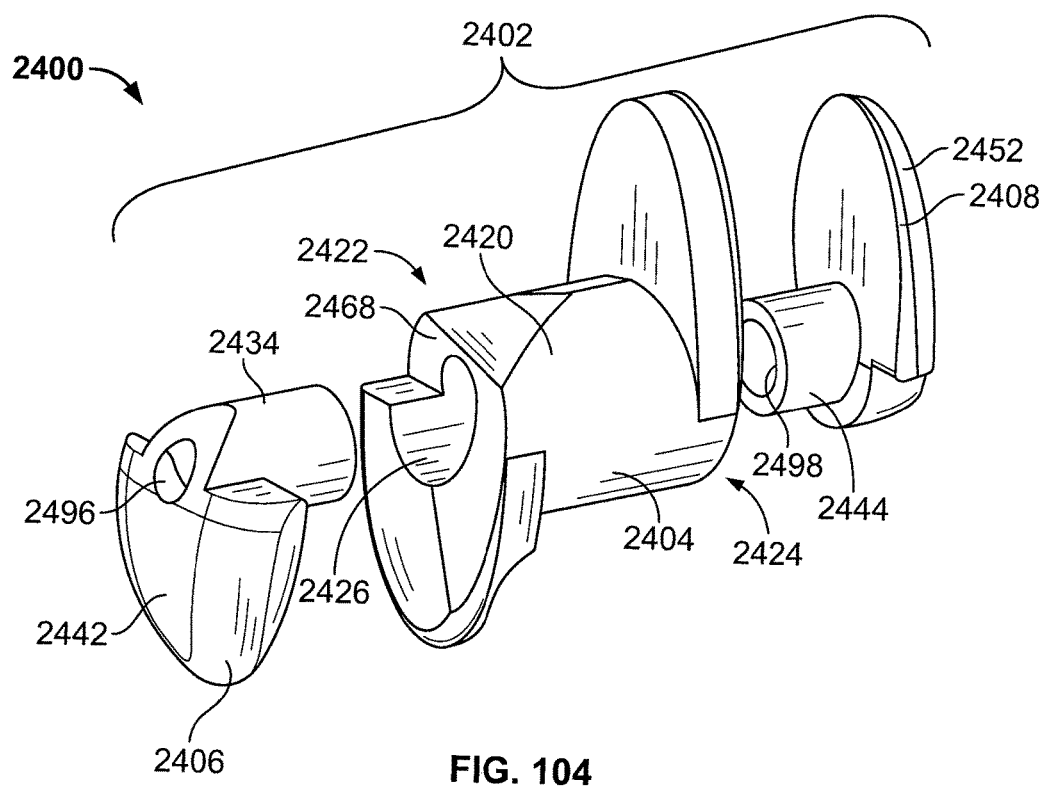
FIG. 104 is an exploded view of an implant device in accordance with another aspect of the invention.
Figure 105:
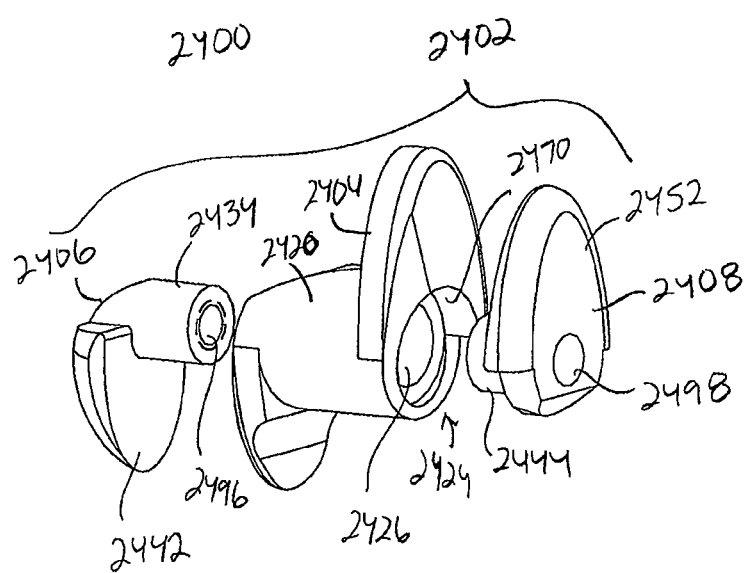
FIG. 105 is another exploded view of the implant device of FIG. 104.

Accordingly, as illustrated most clearly in FIGS. 104 and 105, the first member 2404 includes a first ramp portion 2468 at the first end 2422 and a second ramp portion 2470 at the second end 2424. In one embodiment, the application of an axial force on the second and third members 2406, 2408 causes the second and third members 2406, 2408 to cam against the first member 2404, in particular the first ramp portion 2468 and the second ramp portion 2470. As the axial force causes the second and third members 2406, 2408 to be drawn into the longitudinal throughbore 2426, the cylindrical portions 2434, 2444 cam against ramp portions 2468, 2470 thereby causing the second and third members 2406, 2408 to rotate. Further, as illustrated, ramp portions 2468, 2470 are preferably configured to move the second and third members 2406, 2408 in opposite rotational directions (i.e., one in a clockwise direction and one in a counterclockwise direction). Having the second and third members 2406, 2408 rotate in opposite rotational directions enables the implant body 2402 to avoid obstacles which may inhibit rotation in one direction, such as other portions of the spine. Thus, as the cylindrical portions 2434, 2444 ride along ramp portions 2468, 2470, the second and third members 2406, 2408 will advantageously both be rotated in a generally posterior direction toward the extended orientation.

A securing mechanism may be used to secure the implant body 2402 in the extended orientation. In one form, the securing mechanism comprises a threaded screw (not shown) that is received in throughbores 2496, 2498 defined in the second and third members 2406, 2408, respectively. The throughbores 2496, 2498 are configured to receive the threaded screw therein. One of the throughbores 2496, 2498 is configured to include a recess, the recess configured to receive the head of the threaded screw. Preferably, the throughbore 2494, 2498 which does not include the recess is threaded. The threaded screw is configured such that when the implant body 2402 is in the compact orientation, the shaft of the threaded screw extends through one of the second and third members 2406, 2408 and into the other a distance to secure both the second and third members 2406, 2408 to the first member 2404. Additionally, the threaded screw is configured such that when the implant body 2402 is in the extended orientation, the threaded screw does not extend beyond the implant body 2402. When the screw is tightened, an axial force is applied to the second and third members 2406, 2408 thereby camming the second and third members 2406, 2408 against the first member 2404 so that the implant body 2402 is shifted to the extended orientation.

The implant devices of the present invention may be fabricated from any suitable materials having desirable strength and biocompatibility. Suitable materials may include, for example, biocompatible metals and related alloys (such as titanium and stainless steel), shape memory metals (such as Nitinol), biocompatible polymers (including, for example, materials of the polyaryletherketone family such as PEEK (polyetheretherketone), PAEK (polyaryletherketone), PEK (polyetherketone), PEKK (polyetherketoneketone), PEKEKK (polyetherketoneetherketoneketone), PEEKK (polyetheretherketoneketone), and PAEEK (polyaryletheretherketone), filled materials (such as carbon or glass fiber-reinforced materials), bone substitute materials (such as hydroxyapatite and tricalcium phosphate), composite materials, and/or any combination of the above.

In one form, the implant devices are formed of a PEEK-type material. In another from, the implant device may be formed, in whole or in part, or coated with a calcium phosphate ceramic bone substitute such as hydroxyapatite, tricalcium phosphate, and/or mixtures thereof. Particularly preferred hydroxyapatite and tricalcium phosphate compositions include those disclosed in, for example, U.S. Pat. No. 6,013,591, U.S. Pat. No. RE 39,196, and U.S. Patent Application Publication No. 2005/0031704, which are hereby incorporated in their entirety herein. Coating with the calcium phosphate ceramics can be achieved by any known method, including dip coating-sintering, immersion coating, electrophoretic deposition, hot isostatic pressing, solution deposition, ion-beam sputter coating and dynamic mixing, thermal spraying techniques such as plasma spraying, flame spraying and high-velocity oxy-fuel combustion spraying. In one preferred embodiment, hydroxyapetite coating is achieved by plasma spraying.

In yet another form, the implant device may be formed of a PEEK-type material and coated with such a bone substitute material. In yet another form, the implant device may be formed, in whole or in part, coated with, injected with, incorporate, and/or retain a bone growth stimulating composition such as the bioactive hydrogel matrix described, for example, in U.S. Pat. No. 6,231,881, U.S. Pat. No. 6,730,315, U.S. Pat. No. 6,315,994, U.S. Pat. No. 6,713,079, U.S. Pat. No. 6,261,587, U.S. Pat. No. 5,824,331, U.S. Pat. No. 6,068,974, U.S. Pat. No. 6,352,707, U.S. Pat. No. 6,270,977, U.S. Pat. No. 5,614,205, U.S. Pat. No. 6,790,455, U.S. Pat. No. 5,922,339, and U.S. Patent Application Publication No. 2005/0118230, which are hereby incorporated in their entirety herein.

The modulus of elasticity of any of the implant devices of the present invention is selected so as to provide the desired amount of rigidity and/or compliance to the implant device. The geometry of the implant device and/or the materials from which the implant device is fabricated may be selected so as to provide any desirable modulus of elasticity. In one form, the modulus of elasticity of the implant device is preferably equal to or less than that of bone. In one form, the modulus of elasticity of the implant device is preferably greater than that of an intervertebral disc and less than that of cortical bone.

Those skilled in the art will recognize that a wide variety of modifications, alterations, and combinations can be made with respect to the above described embodiments without departing from the spirit and scope of the invention, and that such modifications, alterations, and combinations, are to be viewed as being within the scope of the invention.

What is claimed is:

1. An implant device for implantation between adjacent spinous processes, the implant device comprising:
an implant body;
a first member of the implant body having a unitary, one-piece construction, the unitary, one-piece first member being configured for engaging a vertebra and including a first vertebral engaging portion having a first seat portion extending between proximal ends of a first arm and a second arm, and a first spacer portion extending from the first vertebral engaging portion;
a second member of the implant body having a unitary, one-piece construction distinct from the unitary, one-piece first member so that the first and second members comprise two distinct pieces, the unitary, one-piece second member being configured for engaging a vertebra and including a second vertebral engaging portion having a second seat portion extending between proximal ends of a third arm and a fourth arm, and a second spacer portion extending from the second seat portion; and
a pivot connection at which the first and second members are pivotably coupled, with the implant body being configured to be pivoted between a compact orientation, in which a stop arrangement is formed on the first and third arms via stop surfaces that are pivoted into engagement with each other so that the first arm abuttingly engages the third arm and a spaced arrangement is formed between the second and fourth arms so that the second and fourth arms are pivoted away from each other, and an extended orientation, in which a stop arrangement is provided via a stop surface of the first spacer portion and a stop surface of the second spacer portion that are pivoted into engagement with each other so that the stop surface of the first spacer portion abuttingly engages the stop surface of the second spacer portion and in which the first and third arms are shifted to extend away from one another, with pivoting of the distinct first and second members between the compact and extended orientations causing an entirety of the first member to simultaneously pivot relative to an entirety of the second member.

2. The implant device of claim 1, wherein the second and fourth arms include tool engagement portions configured to receive an insertion tool.

3. The implant device of claim 1, wherein the stop surface of the first spacer portion and the stop surface of the second spacer portion are pivoted away to extend generally oppositely from each other with the implant body in the compact orientation.

4. The implant device of claim 1, wherein the arms have tapered distal ends to assist insertion of the implant body in the compact orientation.

5. The implant device of claim 1, wherein the spacer portions of the first and second implant body member are pivoted together with the implant body in the extended orientation and sized to distract the adjacent spinous processes to a predetermined spatial relationship when positioned therebetween.

6. A method of implanting an implant device between spinous processes of adjacent vertebrae, the method comprising:
engaging a tool with a pair of unitary, one-piece implant members that comprise two distinct pieces of the implant device at tool engaging end portions thereof, each of the implant members having a generally U-shaped configuration with a seat portion and a pair of arms that are spaced from each other and extend in the same general direction away from the seat portion, each arm having a proximate end connected to the seat portion and a distal end spaced therefrom with each of the arms having a length between the proximate and distal ends thereof;

arranging the seat portion of each implant member to face generally in an insertion direction;

arranging the arms at end portions of the implant members generally opposite to the tool engaging end portions thereof to be engaged with one another and to extend generally in the insertion direction;

arranging the arms at the tool engaging end portions of the implant members to be spaced from each other along an entirety of the length of each of the spaced arms;

advancing the tool and implant members along the insertion direction with the engaged arms and the spaced arms being advanced until the engaged arms extend through a space between the adjacent spinous processes; and pivoting the implant members with the tool to cause the seat portions to face generally opposite one another in respective upward and downward directions in the space between the adjacent spinous processes for engaging the corresponding spinous processes with the engaged arms pivoted to extend away from one another.

7. The method of claim 6, wherein pivoting the implant members with the tool to cause the seat portions to face generally opposite one another in the space between the adjacent spinous processes includes distracting the spinous processes in engagement with the seat portions.

8. The method of claim 6, wherein the tool pivots the implant members by staying in engagement with the tool engaging end portions thereof during pivoting of the implant members to an extended orientation in which the seat portions face generally opposite one another in the respective upward and downward directions.

9. The method of claim 6, wherein the tool comprises a scissor-like tool having implant engaging portions, and
pivoting the implant members with the tool to cause the seat portions to face generally opposite one another comprises pivoting the scissor-like tool thereby shifting the implant engaging portions thereof relative to each other.

10. The method of claim 9, wherein shifting the implant engaging portions of the scissor-like tool relative to each other comprises shifting the implant engaging portions toward each other to cause the seat portions to face generally opposite one another.

* * * * *